US007846466B2

(12) United States Patent
Shea et al.

(10) Patent No.: US 7,846,466 B2
(45) Date of Patent: Dec. 7, 2010

(54) BIODEGRADABLE SCAFFOLDS AND USES THEREOF

(75) Inventors: Lonnie D. Shea, Evanston, IL (US); Lonnie L. Shea, Brownstown, MI (US); Kevin Whittlesey, Washington, DC (US); Yang Yang, Chicago, IL (US); Christopher Rives, Chicago, IL (US); Laura De LaPorte, Evanston, IL (US); Jae-Hyung Jang, Richmond, CA (US)

(73) Assignee: Northwestern University, Evanston, IL (US)

( * ) Notice: Subject to any disclaimer, the term of this patent is extended or adjusted under 35 U.S.C. 154(b) by 314 days.

(21) Appl. No.: 11/149,462

(22) Filed: Jun. 9, 2005

(65) Prior Publication Data
US 2006/0002978 A1 Jan. 5, 2006

Related U.S. Application Data

(60) Provisional application No. 60/578,785, filed on Jun. 10, 2004.

(51) Int. Cl.
*A61F 2/02* (2006.01)
*A61K 9/00* (2006.01)

(52) U.S. Cl. ..................................... 424/426; 424/484

(58) Field of Classification Search ........................ None
See application file for complete search history.

(56) References Cited

U.S. PATENT DOCUMENTS

| | | | | |
|---|---|---|---|---|
| 4,647,599 | A * | 3/1987 | Bezzegh et al. | 424/470 |
| 5,916,593 | A * | 6/1999 | de Haan et al. | 424/465 |
| 6,281,256 | B1 * | 8/2001 | Harris et al. | 521/51 |
| 6,495,165 | B1 * | 12/2002 | Thosar et al. | 424/489 |
| 6,797,738 | B2 | 9/2004 | Harris et al. | |

OTHER PUBLICATIONS

Arnarson, et al., J. Pharm. Pharmac. (1977) 24P and 26P.
Aebischer, et al, Brain Research, (1998) 454:179-187.
Aebischer, et al., Journal of Neuroscience Research (1989) 23:282-289.
Baldwin, et al., Transactions of the ASME, (1995) 62; 117:62-74.
Barras, et al., Journal of Neuroscience Research (2002) 70:746-755.
Belkas, et al.Neurological Research (2004) 26:151-160.
Berry, et al., Molecular and Cellular Neuroscience 92001) 17:706-716.
Bloch, et al., Experimental Neurology (2001) 172:425-432.
Bonadio, et al., Nature medicine (1999) 5, 7:753-759.
Boyd, et al., Molecular Neurobiology, (2003) 27:277-323.
Buettner, et al., Develoopmental Biology (1994) 163:407-422.
Bunge, J. Neurol (1994) 241:S36-S39.
Bunge, The Neuroscientist (2001) 7, 4:325-339.
Calder, et al., Journal of Hand Surgery (1995) 20B: 4: 423-428.
Carstensen, et al., International Journal of Pharmeceutics, (1978), 1: 2:85-70.
Carstensen, Pharm Princ, Chapter 4 Solid Dose; pp. 219-292.
Cavallaro, et al., Biotechnology and Bioengineering (1994) 43:781-791.
Chao, Nature Reviews/Neuroscience (2003) 4:299-309.
Clark, et al., Journal of Cell Science 91993) 105:203-212.
David, et al., Annu. Rev. Neurosci (2003) 26:411-40.
Doolabh, et al., Rev. Neurosci. (1996) 7:1:47-84.
Dow, et al., Cell & Tissue Research (1991) 265:345-351.
Evans, The Anatomical Record, (2001) 263:396-404.
Fang, et al., Proc. Natl. Acad. Sci. USA (1996) 93:5753-5758.
Fawcett, et al., Annu. Rev. Neurosci. (1990) 13:43-60.
Feneley, et al., Experimental Neurology (1991) 114:275-285.
Fine, et al., Eur. J. Neurosci. (2002) 15:589-601.
Friedman, et al., Neurosurgery (2002) 51:742-752.
Geller, et al., Experimental Neurology (2002) 174:125-136.
Gibson, et al., Microsurgery (1989) 10:126-129.
Hadlock, Arch Otolaryngol Head Neck Surg. (1998) 124:1081-1086.
Hadlock, et al., Laryngoscope (1999) 109:1412-1416.
Ishaug, et al., Journal of Biomedical Materials Research (1994) 28:1445-1453.
Jang, et al., Journal of Controlled Release (2003) 86:157-168.
Jang, et al., Expert Rev. Medical Devices (2004) 1:127-138.
Jenq, et al., Experimental Neurology (1987) 97:662-671.
Kawabata, et al., Pharmaceutical Research (1995) 12:6:825-830 .
Kzarian, et al., J. Am. Chem. Soc. (1996) 118:1729-1736.
Labrador, et al., Experimental Neurology (1998) 149:243-252.
Langer, Nature (1998) 292:S5-S10.
Li, et al., Chemical Materials (1992) 9:195-200.
Lo, et al., Tissue Engineering, (1995) 1:15-30.
Maquet, et al., J. Biomed. Mat. Res. (2000) 639-651.
Mikos, Polymer (1994) 35:5:1068-1077.
Mooney, et al., Transplantation Proceedings (1994) 26:6:3425-3426.
Mooney, et al., Journal of Biomedical Materials Research (1995) 29:959-965.
Mooney, et al., Biomaterials (1996) 17:14:1417-1422.
Nof, et al., J. Bio. Mat. Res. (2001) 349-356.
Ozawa, et al., Journal of Clinical Investigation (2004), 113:4:516-527.
Pannier, et al., Molecular Therapy, (2004) 10:1:19-26.
Park, et al., Polymer Engineering and Science, (1995) 35:5:432-440.
Pascher, et al., Gene Terapy (2004) 11:133-141.
Patist, et al., Biomaterials (2004) 25:1569-1582.
Principles of Tissue Engineering, Academic Press, (1997).
Rafiuddin-Ahmed, Brain Research (2003) 993:208-216.
Rodriguez, et al., Biomaterials (1999) 20:1489-1500.
Schmidt, et al., Annu. Rev. Bioed. Eng. (2003) 5:293-347.
Segura, et al., Biomaterials (2005) 26:1575-1584.
Shea, et al., Nature Biotechnology (1999) 17:551-554.
Tai, et al., Biotechnol Prog. (1998) 14:364-370.

(Continued)

*Primary Examiner*—Anand U Desai
(74) *Attorney, Agent, or Firm*—Klauber & Jackson LLC

(57) ABSTRACT

The invention is directed to scaffolds containing porous polymer material prepared by a process of gas foaming/particulate leaching and a wet granulation step prior to gas foaming and particulate leaching, particularly having a characteristic interconnected pore structure, as well as sustained release of protein, DNA or cells, and to methods for using such porous polymer material for preparation of scaffolds, particularly for tissue engineering.

3 Claims, 30 Drawing Sheets

OTHER PUBLICATIONS

Takakura, et al., Advanced Drug Delivery reviews (1998) 34:93-108.
Talac, et al., Biomaterials (2004) 25:1505-1510.
Taylor, et al., Journal of Controlled Release (2004) 98:281-294.
Tessier-Lavigne, Genetics and Development, (1994) 4:596-601.
Travers, J. Pharm. Pharmac. (1975) 27:516-522.
Tyrone, et al., Journal of Surgical Research (2000) 93:230-236.
Valentini, et al., Experimental Neurology (1987) 98:350-356.
Van Scholk, Enc. Pharm Tech (1991) p. 3572.
Widmer, et al., Biomaterials (1998) 19:1945-1955.
Xu, et al., Bomaterials (2003) 24:2405-2412.
Zoglio, et al., J. Pharm Sci. (1975) 64:11:1869-1873.
Zoglio, et al., J. Pharm Sci. (1976) 65:8:1205-1208.

* cited by examiner

A.
B.

a.

b.

a.

b.

c.

Neurite outgrowth on PLG

<Antibody staining>

2μg, PEI/pNGF, N/P=18, 1hr incubation, 2d cell culture

BIODEGRADABLE SCAFFOLDS AND USES THEREOF

CROSS-REFERENCE TO RELATED APPLICATIONS

The present application is a non-provisional application claiming the priority of provisional application Ser. No. 60/578,785, filed Jun. 10, 2004, the disclosure of which is incorporated by reference herein in its entirety. Applicants claim the benefits of this application under 35 U.S.C. §119 (e).

FIELD OF THE INVENTION

This invention relates generally to devices for the preparation and delivery of proteins, DNA or cells to effect growth, regrowth, or repair of tissues damaged or destroyed by disease, accident or surgery. More particularly, the invention is directed to a device fabricated as a biodegradable polymeric scaffold that is particularly useful for the controlled or sustained release of DNA and/or protein or cells to promote regrowth of tissue in vivo. The invention is also directed to the use of the devices for the growth of multifilamentous tissue such as nerve tissue, and can also be used for the delivery of drugs, enzymes and other factors to sites in a host, as well as for gene therapy, and for spatially controlled release of growth or differentiation factors or DNA encoding such factors. Additionally, the present invention is directed to methods of fabrication of the devices that allows for the incorporation and release of cells or one or more bioactive factors or DNA encoding such factors to the tissue site and to the application of such to the treatment of diseases, disorders or deficiencies resulting from the loss of tissue function.

BACKGROUND OF THE INVENTION

One of the most striking features of virtually all normal tissues is the high degree of order and patterning that occurs during all stages of development. Whether one examines such diverse processes as the orderly formation of axon tracts, the creation of arrays of skeletal muscle fibers or the formation of kidney glomeruli, it is clear that the creation of normal tissue follows precise rules of organization. Little is known about how such order is generated in the body nor have techniques been developed that induce in a controllable manner the generation of multilayered ordered tissue structures in vitro or in vivo.

Just as order is a striking feature of normal tissues, so is disorder a feature of pathology. Disorder is seen in degenerative processes and is also seen in the failure of regeneration to create fully normal tissue. One common example of such disorder in tissue regeneration is seen in scar tissue in which the precisely patterned organization of cells that existed prior to injury is not reformed. When it occurs in deeper structures, function can be severely compromised. Indeed, the generation of ordered structures is so essential to the creation of a functioning nervous system that not even simple reflex loops can be established in its absence let alone the complexity of higher order motor and cognitive processes.

Since disorder is a feature of pathology and order is a feature of normal tissue function, and if normal tissue function requires the transmission of order through multiple layers of cells and the ability of cells to communicate to each other through transfer of factors, then it follows that a critical goal in the field of tissue repair or tissue engineering is the discovery of a means of creating structures that display order by allowing for the generation of multiple layers of cells and to enhance the ability of these cells to communicate with each other as a result of intentional design features utilized by the practitioner of the art.

While in general the field of tissue repair and tissue engineering has grown over the past decade to include various means for providing for new cell growth and new tissue formation, the area of nervous tissue regeneration has still proven to be perhaps the most complex. Nerve injuries complicate successful rehabilitation more than any other form of trauma. Painful neuroma formation, often more disabling than its associated sensory deficits, commonly causes major disability. Improvements in the techniques of nerve repair could provide better return of protective sensibility and tactile discrimination, reduce denervation atrophy of muscles, and prevent or minimize pain syndromes.

The nervous system is composed of numerous types of cells, including neurons and glial, or satellite cells. Glial cells include Schwann cells. The neurons carry signals between the brain and the rest of the body, while the primary role of the Schwann cells is to provide support for the neurons and to enhance the speed of electrical signals. Schwann cells also produce proteins essential for neuron growth (Bunge, M., (1994), J Neurol. December;242 (1 Suppl 1):S36-9; Tortora, (1992), Principles of Human Anatomy, Nervous System, $6^{th}$ Edition, Chapter 16, Nervous Tissue, pp. 456-468). Each neuron is composed of a cell body, an axon, and dendrites. The tip of an axon is the growth cone and is responsible for navigation. Neurons can make multiple contacts with one or more neurons. The ability of neurons to extend neurites is of prime importance in establishing neuronal connections during development. It is also required during regeneration to re-establish connections destroyed as a result of a lesion. The organization of the contacts determines the overall function of the nervous system. The axons are surrounded by an insulating layer or myelin sheath formed by the Schwann cells (Tortora, (1992), Principles of Human Anatomy, Nervous System, $6^{th}$ Edition, Chapter 16, Nervous Tissue, pp. 456-468). Injury to the axon that causes the Schwann cells to lose contact with the axons stimulates production of neurotrophic factors such as nerve growth factors. Nerve growth factor (NGF) has been shown to greatly enhance the growth of neurons in culture. With contact, regenerating axons stimulate Schwann cells to proliferate and form a basal lamina of collagen, proteoglycans, and laminin.

When a nerve is severed, a gap is formed between the proximal and distal portions of the injured nerve. In order for the nerve axon to regenerate and reestablish nerve function, it must navigate and bridge the gap. Under the appropriate conditions, e.g., minimal gap length, the proximal end forms neurite growth cones that navigate the gap and enter endoneural tubes on the distal portion. The growth cones sense the extracellular environment and determine the rate and direction of nerve growth. The motion of the axon is responsive to environmental signals provided by other cells that guide the growth cone (Tessier-Lavigne, (1994), Curr. Opin. Genet. Dev. August 4(4), pp. 596-601).

Once the growth cones reach the distal segment, they enter the endoneural tubes left from the degenerated axons. However, the growth cones and the dendrites on the proximal stump typically grow in many directions and unless the injury is small, the growth cones may never reach the distal segment. The natural ability of the nerve to regenerate is greatly reduced by the disruption of environmental cues resulting from, for example, soft tissue damage, formation of scar tissue, and disruption of the blood supply (Mackinnon and Dellon, (1988), J Hand Surg [Am]. November;13 (6):935-42;

Fawcett and Keynes, (1990), Annu Rev Neurosci.;13:43-60, Buettner et al, (1994), Dev Biol., June;163(2):407-22).

Several techniques have previously been attempted to aid and accelerate the repair of damaged nerves: suturing the severed ends, suturing an allograft or autograft, or regenerating the nerve through a biological or synthetic conduit (Valentini et al., (1987), Exp Neurol., November; 98(2):350-6; Aebischer et al., (1988), Brain Res., June 28;454(1-2):179-87; Fenely et al., (1991), Exp Neurol., December; 114(3): 275-85; Calder and Green, (1995) J Hand Surg [Br], August; 20(4):423-8).

Autografts and allografts require a segment of a donor nerve acquired from the patient (autograft) or a donor (allograft). The donor nerve segment is removed from another part of the body or a donor and then sutured between the unattached ends at the injury site. Nerve autograft procedures are difficult, expensive, and offer limited success. Often, a second surgical procedure is required and may lead to permanent denervation at the nerve donor site. Allografts typically require the use of immunosuppressive drugs to avoid rejection of donor segments.

Artificial nerve grafts have been used in attempts to avoid the problems associated with autografts and allografts. Artificial grafts do not require nerve tissue from another part of the body or a donor. However, use of artificial nerve grafts has met with only limited success. Axonal regeneration in the peripheral nervous system has only been achieved for graft lengths up to approximately 3 cm in nonhuman primates. There has been little or no success with longer grafts. The previously used artificial nerve grafts were unsuitable for bridging longer gaps between distal and proximal nerve stumps and, therefore, are unsuitable for treating a significant proportion of nerve injuries.

Neurite growth has been aided to a limited extent by fabricating grooves on substrate surfaces (Clark et al., (1993), J Cell Sci., May;105 (Pt 1):203-12; Dow et al., (1991), Cell Tissue Res. August;265(2):345-51). The grooves employed in these studies were engraved on plastic or quartz substrates. The substrates utilized are unsuitable for implantation in vivo and thus the authors were unable to determine if the grooves could guide neurite growth in an animal. Alignment of neurons using physical guidance cues alone is highly uncertain and difficult to reproduce. For example, the neurites are typically aligned on only part of the substrate and unaligned on other parts and exhibit undesirable axon branching.

Tai et al., (Biotechnol. Prog. (1998), Vol. 14: 364-370) refer to the effects of micropatterned laminin glass surfaces on neurite outgrowth and growth cone morphology. In Tai et al., micropatterns consisting of laminin stripes alternating with glass stripes were formed on glass coverslips. Neuronal cultures were prepared from chicken dorsal root ganglia and seeded on either micropatterned laminin coverslips or on a uniform laminin coated glass surface. While neuronal growth on the micropatterned laminin surface was biased in the direction of the pattern, severe axon branching formed dense axon outgrowth. Thus, while the laminin provided some level of chemical guidance, applicability of the technique was limited. In addition, the glass substrates are unsuitable for implantation into patients.

More recently, tissue engineering approaches for nerve repair employ polymer conduits to protect the regenerating nerve and promote regrowth. Nerve conduits used for peripheral nerve and spinal cord injuries are typically termed guidance channels and bridges, respectively (G. R. Evans, Anat. Rec. 263 (4) (2001), 396-404; H. M. Geller, J. W. Fawcett, Exp. Neurol. 174 (2) (2002) 125-136). These conduits are implanted across the injury site and serve to support the damaged nerve by reducing infiltrating scar tissue, maintaining a continuous path, and directing axon outgrowth by physical guidance (C. E. Schmidt, J. B. Leach, Annu. Rev. Biomed. Eng. 5 (2003) 293-347). Conduits are typically fabricated with either single or multiple lumens (R. Talac, et al., Biomaterials 25 (9) (2004) 1505-1510; P. Aebischer, A. N. Salessiotis, S. R. Winn, J. Neurosci. Res. 23 (3) (1989) 282-289) and the lumen can be filled with a hydrogel (e.g. matrigel, fibrin) (R. O. Labrador, M. Buti, X. Navarro, Exp. Neurol. 149 (1) (1998) 243-252) or used empty (K. L. Gibson, J. K. Daniloff, G. M. Strain, Microsurgery 10 (2) (1989) 126-129). Single lumen conduits have been extensively used in peripheral nerve regeneration (V. B. Doolabh, M. C. Hertl, S. E. Mackinnon, Rev. Neurosci. 7 (1) (1996) 47-84). More recently, conduits with multiple, straight lumens have been proposed to segregate functional pathways, with each lumen acting as a guidance channel for axon growth (J. A. Friedman, et al., Neurosurgery 51 (3) (2002) 742-751 (discussion 751-752)). The material, mechanics, and physical properties of the conduits can affect the extent of nerve regeneration. Guidance channels have been fabricated from a range of natural and synthetic polymers (G. R. Evans, Anat. Rec. 263 (4) (2001) 396-404) using a variety of fabrication techniques, including solvent casting, extrusion, freeze drying, and dip molding (C. M. Patist, et al., Biomaterials 25 (9) (2004) 1569-1582; T. Hadlock, et al., Laryngoscope 109 (9) (1999) 1412-1416; M. S. Widmer, et al., Biomaterials 19 (21) (1998) 1945-1955). Materials used for fabrication include both natural (e.g., collagen) (M. Rafiuddin Ahmed, R. Jayakumar, Brain Res. 993 (1-2) (2003) 208-216; S. T. Li, et al., Clin. Mater. 9 (3-4) (1992) 195-200; S. J. Taylor, J. W. McDonald III, S. E. Sakiyama-Elbert, J. Control. Release 98 (2) (2004) 281-294) and synthetic polymers (e.g., silicone, ethylene vinyl coacetate (EVAc), poly(lactide-co-glycolide) (PLG)) (K. L. Gibson, J. K. Daniloff, G. M. Strain, Microsurgery 10 (2) (1989) 126-129; E. G. Fine, et al., Eur. J. Neurosci. 15 (4) (2002) 589-601). The processing of these materials can provide conduits with a range of degradation rates, porosities, and mechanical properties. Conduits with porosity ranging from semi-permeable to macroporous have been investigated, with the hypothesis that the porosity can allow access of soluble growth promoting factors or nutrients (M. S. Widmer, et al., Biomaterials 19 (21) (1998) 1945-1955; F. J. Rodriguez, et al., Biomaterials 20 (16) (1999) 1489-1500; C. B. Jenq, L. L. Jenq, R. E. Coggeshall, Exp. Neurol. 97 (3) (1987) 662-671; V. Maquet, et al., J. Biomed. Mater. Res. 52 (4) (2000) 639-651) from the surrounding environment. Additionally, the mechanical properties of the conduit must be sufficient to avoid channel collapse, which would limit neurite outgrowth and regeneration (C. E. Schmidt, J. B. Leach, Annu. Rev. Biomed. Eng. 5 (2003) 293-347; V. B. Doolabh, M. C. Hertl, S. E. Mackinnon, Rev. Neurosci. 7 (1) (1996) 47-84. In addition to providing structural support, nerve conduits can also function as a vehicle for localized delivery of neurotrophic factors (E. G. Fine, et al., Eur. J. Neurosci. 15 (4) (2002) 589-601; X. Xu, et al., Biomaterials 24 (13) (2003) 2405-2412). Neurotrophic factors (e.g., nerve growth factor (NGF), neurotrophin-3 (NT-3), brain derived neurotrophic factor (BDNF)) are not typically produced in sufficient quantities after an injury (J. G. Boyd, T. Gordon, Mol. Neurobiol. 27 (3) (2003) 277-324). Localized delivery of these factors, which can be achieved by a pump, polymeric delivery, or the transplantation of engineered cells, has been employed to promote neuronal survival and stimulate neurite outgrowth following trauma (M. V. Chao, Nat. Rev., Neurosci. 4 (4) (2003) 299-309; S. David, S. Lacroix, Annu. Rev. Neurosci. 26 (2003) 411-440. The ability to combine neurotrophic factor delivery with a conduit can support, promote, and direct neurite outgrowth. EVAc polymers shaped into guidance channels that release neurotrophic factor demonstrated increased numbers of myelinated axons traversing an injury site relative to empty channels (E. G. Fine, et al., Eur. J. Neurosci. 15 (4) (2002) 589-601; F. M. Barras, et al., J. Neurosci. Res. 70 (6) (2002) 746-755; J. Bloch, et al., Exp. Neurol. 172 (2) (2001) 425-432.

In situations whereby it is desirous to deliver a gene encoding a particular growth factor to the site of injury to aid in growth of cells and tissues to replace those damaged by injury or disease, one general approach is to incorporate or attach the gene of interest directly into the polymeric matrix of the scaffold itself. While viral approaches can provide the most efficient means of gene transfer, biomaterials may be employed to enhance the efficacy of nonviral vectors by delaying clearance from the tissue, protecting against degradation, and maintaining effective concentrations for long times (Takakura, Y., Mahato, R. I., and Hashida, M. (1998), Adv. Drug Delivery Rev. 34: 93-108; Kawabata, K., Takakura, Y., and Hashida, M. (1995), Pharm. Res. 12: 825-830; Langer, R. (1998), Nature 392: 5-10; Pannier, A. K., and Shea, L. D. (2004), Mol. Ther. 10: 19-26.

Plasmid and modified nonviral vectors delivered from collagen scaffolds have been employed to promote tissue formation in several models, such as bone (Bonadio, J., Smiley, E., Patil, P., and Goldstein, S. (1999), Nat. Med. 5: 753-759; Fang, J., et al. (1996), Proc. Natl. Acad. Sci. USA 93: 5753-5758, cartilage (Pascher, A., et al. (2004), Gene Ther. 11: 133-141, nerve regeneration (Berry, M., et al. (2001), Mol. Cell Neurosci. 17: 706-716, and wound healing (Tyrone, J. W., et al. (2000), J. Surg. Res. 93: 230-236. Additionally, sustained delivery of plasmid DNA from a synthetic polymer, such as poly(lactide-co-glycolide) (PLG) matrices, significantly increased the level of in vivo transfection relative to direct injection (Shea, L. D., Smiley, E., Bonadio, J., and Mooney, D. J. (1999), Nat. Biotechnol. 17: 551-554). Transgene expression can influence tissue formation within or around the scaffold (Jang, J. H., Houchin, T. L., and Shea, L. D. (2004), Expert Rev. Med. Devices 1: 127-138. Although polymeric delivery of plasmid can promote gene transfer, the scaffold design parameters (e.g., porosity, loading) that regulate in vivo transgene expression are not well understood.

Accordingly, one object of the present invention is to provide a means of mechanical support for the attachment of cells to improve tissue regeneration. A second object is to incorporate into, or attach to, this biodegradable support either DNA encoding specific proteins, or the proteins themselves, such as growth factors or enzymes that can aid in modification of the microenvironment at the site of injury, thus allowing for more conducive conditions for cellular proliferation and tissue regeneration. Accordingly, the mechanisms for providing this means of tissue repair would be accomplished in a manner that can be applied at low cost and with great reproducibility.

The failure of others to achieve the above two objects is shown clearly by examples from the very fields that are most closely related to the purposes of the invention. These are the fields of tissue repair by providing a guidance tube or scaffold upon which new cells and tissue can be generated, while at the same time providing a means by which the new cells can incorporate genes of interest to aid in further cellular communication, proliferation and tissue repair.

All publications, patent applications, patents and other reference material mentioned are incorporated by reference in their entirety. In addition, the materials, methods and examples are only illustrative and are not intended to be limiting. The citation of references herein shall not be construed as an admission that such is prior art to the present invention.

SUMMARY OF THE INVENTION

In its broadest aspect, the present invention provides a biodegradable polymeric scaffold to provide a mechanical support for tissue regeneration. The scaffold comprises a polymeric matrix prepared by a gas foaming/particulate leaching procedure, and includes a wet granulation step prior to gas foaming that allows for a homogeneous mixture of porogen and polymer and for sculpting the scaffold into the desired shape. The polymeric matrix in the scaffold acts as a substrate permissible for cell growth or for incorporation of DNA or protein and for controlled or sustained release of such DNA, protein or cells at the site of injury. In addition, such protein or DNA may be taken up by cells at the site of injury to provide genes encoding proteins such as enzymes or growth factors to aid in growth of cells at the site of injury. The present invention also provides a nerve guidance tube that is fabricated in a manner that allows for spatially controlled attachment of the cells, proteins or DNA for release over a period of time sufficient to allow enhanced cell or tissue growth or regrowth. The guidance tube may contain one or more lumens. The biodegradable polymer used for preparation of the guidance tube is made by a gas foaming/particulate leaching process, as well as a wet granulation step, these methods thus avoiding the use of organic solvents and/or elevated temperatures and making it more conducive to incorporation of bioactive factors or cells. The wet granulation procedure used in preparation of the polymeric matrix for the nerve guidance tube also offers an advantage over use of the gas foaming/particulate leaching process alone, since the addition of this step allows for a more homogeneous mixture of porogen and polymer and allows for ease of fabrication of the polymeric matrix into the desired shape. The inventors have also identified particular combinations of high and low molecular weight polymers that, when combined with the wet granulation step prior to gas foaming and particulate leaching, allow for the sustained release of DNA, proteins or cells from the scaffold, and provides a mechanically stable conduit which does not compress or collapse after in vivo implantation, thus allowing the channel to remain open for proper cell growth, and in addition, when used for nerve generation, allows for proper neurite outgrowth.

A first aspect of the invention provides a scaffold for propagation of tissue, comprising a porous polymer matrix containing pores formed by gas foaming and pores formed by leaching out of a particulate from the polymer, wherein the polymer is mixed with a porogen by wet granulation prior to gas foaming and prior to molding of the scaffold. In a particular embodiment, the mixing of polymer with porogen by wet granulation results in improved homogeneity of the polymer and porogen mixture and fabrication of the desired geometry of the scaffold.

In another particular embodiment, the polymer matrix used to prepare the scaffold comprises a biocompatible and biodegradable polymer. In yet another particular embodiment, the polymer matrix is a homopolymer or copolymer of lactic acid and/or glycolic acid and/or poly(caprolactone). In yet another particular embodiment, the polymer matrix comprises a homopolymer of a lactic acid or glycolic acid or poly caprolactone, a copolymer of a lactic acid and glycolic acid, or a copolymer of a lactic acid and a poly caprolactone, or a copolymer of a glycolic acid and poly caprolactone, or a copolymer of glycolic acid, lactic acid and a poly caprolactone. In yet another particular embodiment, the polymer matrix further comprises an aliphatic polyester, a polyanhydride, a polyphosphazine, a polyvinyl alcohol, a polypeptide, an alginate, or any combination thereof.

In yet another particular embodiment, the polymer matrix used to prepare the scaffold is PLG or PLGA. In yet another particular embodiment, the polymer matrix has an interconnected and open pore structure. In yet another particular embodiment, the polymer matrix is comprised of high and low molecular weight PLG. In yet another particular embodiment, the ratio of low to high molecular weight PLG is about 50:50. In yet another particular embodiment, the ratio of low to high molecular weight PLG is about 25:75. In yet another particular embodiment, the polymer matrix exhibits an elastic modulus of about 50 to about 500 kPa. In yet another particular embodiment, the polymer matrix exhibits an elastic modulus of about 110-320 kPa. In yet another particular embodiment, the combination of low and high molecular weight polymer, when used at the given ratios, as exemplified by PLG, and when used in conjunction with the wet granulation step prior to gas foaming and particulate leaching, allows for sustained release of DNA, protein or cells from the polymer matrix of the scaffold, and further allows for retention of the shape of the scaffold following implantation.

In yet another particular embodiment, the scaffold is fabricated in any shape suitable for implantation at the site of the injury to be treated. It may be fabricated as a disk, a cylinder, or as a nerve guidance tube or conduit. The scaffold may be fabricated having a single lumen or multiple lumens. In one particular embodiment, the scaffold having a single lumen may comprise a polymer matrix having a porogen to polymer ratio ranging from about 0:1 to 15:1. In a more particular embodiment, the scaffold having a single lumen may comprise a polymer matrix having a porogen to polymer ratio ranging from about 2:1 to 7:1. In yet another particular embodiment, the scaffold having a porogen to polymer ratio ranging from about 2:1 to 7:1 results in a porosity ranging from about 60% to about 90%. In yet another particular embodiment, the scaffold having multiple lumens may comprise a polymer matrix having a porogen to polymer ratio ranging from about 0:1 to 15:1. In a more particular embodiment, the scaffold having multiple lumens may comprise a polymer matrix having a porogen to polymer ratio of about 5:1.

In yet another particular embodiment, the scaffold fabricated as a cylinder or as a nerve guidance tube or conduit is inserted into the site of an injury. In a more particular embodiment, the injury is an injury to the peripheral or central nervous system. In a more particular embodiment, the injury to the central nervous system is a spinal cord injury, either an acute or chronic spinal cord injury.

A second aspect of the invention provides a method for drug delivery comprising introducing a drug contained within a porous polymer matrix or attached to a porous polymer matrix of the scaffold. In one particular embodiment, the drug is a small organic molecule, a nucleic acid, or a polypeptide capable of stimulating angiogenesis, or of stimulating nerve regeneration or growth or cellular differentiation. In another particular embodiment, the polypeptide is a growth factor contained within the polymer matrix or is mixed with the polymer matrix of the scaffold prior to delivery to the site of injury. In yet another particular embodiment, the growth factor is selected from the group consisting of nerve growth factor (NGF), vascular endothelial growth factor (VEGF), platelet derived growth factor (PDGF), neurotrophin-3 (NT-3), brain derived growth factor (BDNF), acidic and basic fibroblast growth factor (FGF), pigment epithelium-derived factor (PEDF), glial derived growth factor (GDNF), angiopoietin, and erythropoietin (EPO). In yet another particular embodiment, the growth factor is selected from the group consisting of the following Sequence Identification Numbers: SEQ ID NO: 1 (NGF2; PubMed No. 1611243A); SEQ ID NO: 2 (BDNF; PubMed No. CAA62632); SEQ ID NO: 3 (VEGF; PubMed No. NP_003367); SEQ ID NO: 4 (PDGF; PubMed No. P01127); SEQ ID NO: 5 (GDNF; PubMed No. NP_954704); SEQ ID NO: 6 (NT-3; PubMed No. 1BNDB); SEQ ID NO: 7 (FGF1, Acidic FGF; PubMed No. AAS99352); SEQ ID NO: 8 (FGF2; PubMed No. NP_001997); SEQ ID NO: 9 (basic FGF; PubMed No. CAA73868); SEQ ID NO: 10 (PEDF; PubMed No. AAA60058); SEQ ID NO: 11 (angiopoietin; PubMed No. AAM92271); SEQ ID NO: 12 (erythropoietin or EPO; PubMed No. AAF23134).

A third aspect of the invention provides a method for tissue engineering comprising introducing the scaffold as a support for growth of the tissue. In one particular embodiment, the tissue is nerve tissue and the implantation of the scaffold to the site of injury allows for guided nerve tissue regeneration. In another particular embodiment, the guided tissue regeneration is in the spinal cord or in a peripheral nerve.

A fourth aspect of the invention provides a method for cell transplantation, comprising implanting the scaffold at the site of injury. In one particular embodiment, the cells for transplantation are attached/adhered to the polymer matrix of the scaffold. In another embodiment, the cells are entrapped within the pores of the scaffold.

A fifth aspect of the invention provides a method for delivery of a gene, or a vector containing a gene, to a site of injury, comprising introducing a gene or vector containing a gene to be delivered by incorporation of the gene or vector within a porous polymer matrix or by attaching the gene or vector to be delivered to a porous polymer matrix of the scaffold. In one embodiment, the gene or vector to be delivered is mixed with cationic polymers, lipids or other agents to aid in uptake of the gene by cells prior to incorporation of the gene or vector within a porous polymer matrix or prior to attaching the gene or vector to be delivered to a porous polymer matrix of the scaffold. In another embodiment, the gene or vector encodes a growth factor selected from the group consisting of NGF, VEGF, PDGF, NT-3, BDNF, FGF, PEDF, GDNF, angiopoietin and erythropoietin. In yet another particular embodiment, the growth factor is selected from the group consisting of the following Sequence Identification Numbers: SEQ ID NO: 1 (NGF2); SEQ ID NO: 2 (BDNF); SEQ ID NO: 3 (VEGF); SEQ ID NO: 4 (PDGF); SEQ ID NO: 5 (GDNF); SEQ ID NO: 6 (NT-3); SEQ ID NO: 7 (FGF1, Acidic FGF); SEQ ID NO: 8 (FGF2); SEQ ID NO: 9 (basic FGF); SEQ ID NO: 10 (PEDF); SEQ ID NO: 11 (angiopoietin); and SEQ ID NO: 12 (erythropoietin or EPO).

A sixth aspect of the invention provides a scaffold for propagation of tissue, comprising a section of a porous polymer comprising a polymer matrix containing pores formed by gas foaming and pores formed by leaching out of a particulate from the polymer, and a section of impermeable polymer integrally connected, wherein the porous polymer is mixed with a porogen by wet granulation prior to gas foaming and prior to molding of the scaffold. In one embodiment, the porous polymer has a homogeneous open pore structure and the impermeable polymer is of the same or different polymer material but without the open pore structure. In another embodiment, the polymer matrix comprises a biodegradable or biocompatible material. In yet another particular embodiment, the polymer matrix is a homopolymer or copolymer of lactic acid and/or glycolic acid and/or poly(caprolactone). In yet another embodiment, the polymer matrix comprises a homopolymer of a lactic acid or glycolic acid or poly caprolactone, a copolymer of a lactic acid and glycolic acid, or a copolymer of a lactic acid and a poly caprolactone, or a copolymer of a glycolic acid and poly caprolactone, or a copolymer of glycolic acid, lactic acid and a poly caprolactone. In yet another particular embodiment, the polymer matrix further comprises an aliphatic polyester, a polyanhydride, a polyphosphazine, a polyvinyl alcohol, a polypeptide, an alginate, or any combination thereof. A yet further particular embodiment provides for fabrication of the scaffold into any shape suitable for implantation at the site of the injury to be treated.

A seventh aspect of the invention provides a nerve guidance channel constructed of a biodegradable, biocompatible polymer matrix containing pores formed by gas foaming and pores formed by leaching out of a particulate from the polymer, and optionally a section of impermeable polymer integrally connected, wherein the polymer is mixed with a porogen by wet granulation prior to gas foaming and prior to molding of the nerve guidance channel.

In a particular embodiment, the nerve guidance channel comprises a polymer matrix, which may be a homopolymer or a copolymer of lactic acid and/or glycolic acid and/or polycaprolactone. In another particular embodiment the nerve guidance channel may contain a single lumen or multiple lumens. In another particular embodiment, the nerve guidance channel is capable of controlled or sustained release of protein or DNA or cells. In another particular embodiment, the nerve guidance may contain a growth factor or the DNA encoding a growth factor capable of stimulating neurite outgrowth or cellular proliferation or cellular differentiation or nerve tissue regeneration. The growth factor or the DNA encoding a growth factor may be attached to the polymer matrix of the nerve guidance channel or may be encapsulated within the polymer matrix prior to gas foaming. The nerve guidance channel may have an inner diameter equal to about 0.8 to 2.35 mm and an outer diameter of about 1.6 mm to 3.15 mm. The ratio of the porogen to polymer in the nerve guidance channel may range from about 0:1 to about 15:1. In a more particular embodiment, the ratio of the porogen to polymer in the nerve guidance channel may range from about 2:1. In yet another particular embodiment, the transverse compressive strength of the nerve guidance channel decreases as the porogen to polymer ratio increases. In yet another particular embodiment, the elastic module of the nerve guidance channel decreases with an increase in porogen to polymer ratio.

In a more particular embodiment, the sustained release of protein or DNA or cells from the polymer matrix of the nerve guidance channel is dependant on polymer composition and on the method of incorporation of the protein, or DNA, or cells into or onto the polymer matrix of the scaffold. In a yet further particular embodiment, the polymer composition comprises a mixture of high and low molecular weight PLG, and the method of incorporation of the protein, DNA or cells is selected from the group including attachment to the polymer matrix and incorporation into the polymer matrix of the nerve guidance channel. In a more particular embodiment, a polymer composition comprising about 25% low molecular weight (LMW) PLG and 75% high molecular weight (HMW) PLG results in accelerated protein release from the nerve guidance channel. In yet another particular embodiment, the construction of the polymer matrix in the nerve guidance channel by gas foaming/particulate leaching and wet granulation results in a nerve guidance channel capable of retaining its original dimensions following implantation.

An eighth aspect of the invention provides a method of promoting neurite outgrowth, or nerve regeneration comprising connecting the first end of a nerve guidance channel to the proximal stump of a severed nerve and connecting the distal stump of the nerve to the $2^{nd}$ end of the nerve guidance channel, whereby neurite outgrowth or nerve cell growth or nerve regeneration occurs within the lumen(s) of the nerve guidance channel between the severed stumps of the nerves. In one particular embodiment, the nerve guidance channel has a single lumen or a plurality of lumens. In another particular embodiment, when the nerve guidance channel is fabricated with multiple lumens, each lumen may be engineered with individual growth or trophic factors or genes encoding different growth or trophic factors to allow for specialized cellular influx for proper tissue orientation or to target various cell types.

A ninth aspect of the invention provides a process for preparing a scaffold for tissue regeneration containing a porous polymeric matrix comprising the steps of:

a) preparing a porous polymeric matrix containing pores formed by a gas foaming and particulate leaching process;

b) mixing the polymeric matrix with a porogen using a wet granulation process prior to gas foaming and particulate leaching;

c) loading the polymeric matrix into a mold having the desired geometry;

d) transferring the mold to a pressure vessel to equilibrate with gas;

e) removing the scaffold from the mold;

f) immersing the mold in water;

g) drying the mold prior to use.

Other objects and advantages will become apparent from a review of the ensuing detailed description and attendant claims taken in conjunction with the following illustrative drawings. All references cited in the present application are incorporated herein in their entirety.

Image was captured following injection of luciferin. Images show a single mouse at different time points. (B) In vivo CCD signal intensity (photons/s) at implant sites (n=6). (•) Scaffolds incorporating pLuc, (□) no DNA, (♦) empty vector, (x) background. *Statistical significance at P<0.05 between pLuc and all other conditions for all time points less than or equal to 105 days.

Figure 6:
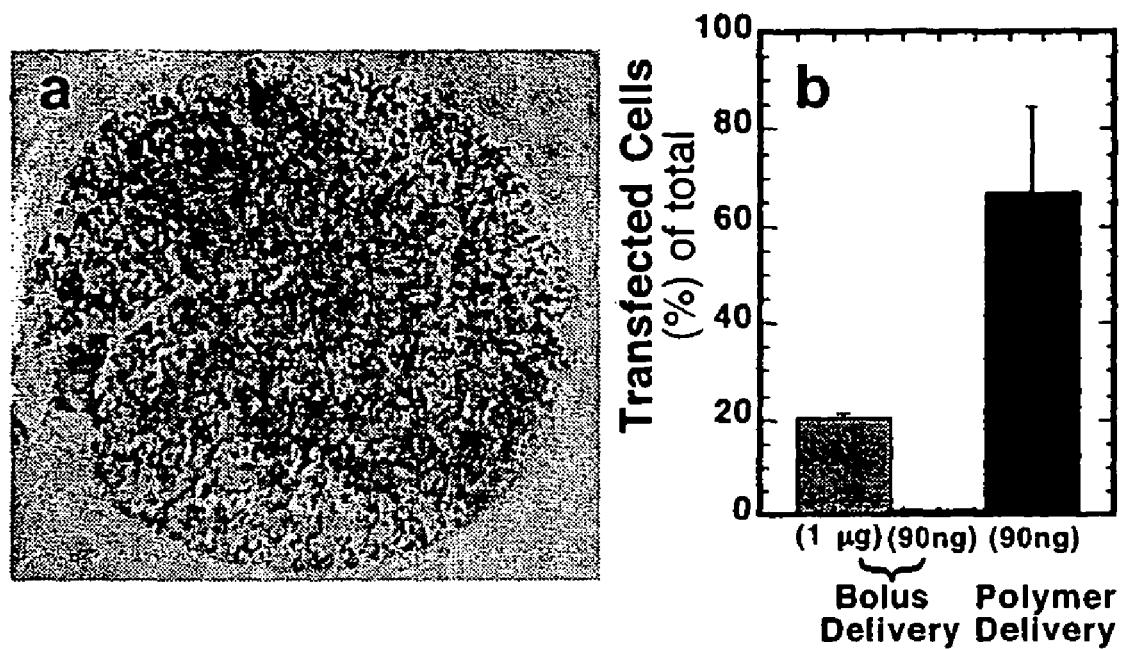

FIG. 6: (a) Photomicrograph of X-gal stained cells on a PLG disk. (b) Luciferase levels for bolus delivery and polymer delivery.

Figure 7:
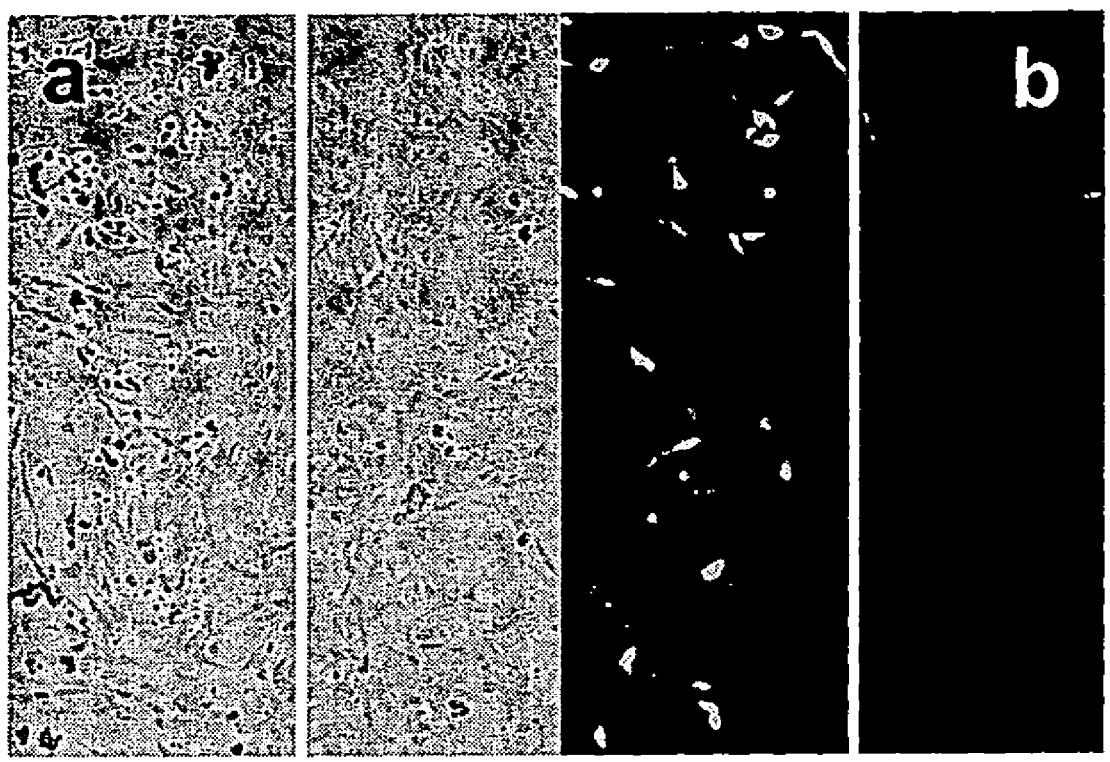

FIG. 7: Photomicrograph of (a) cell cultured on surface and (b) GFP expressing cells. The white line indicates the separation between the coated and uncoated regions.

Figure 8:
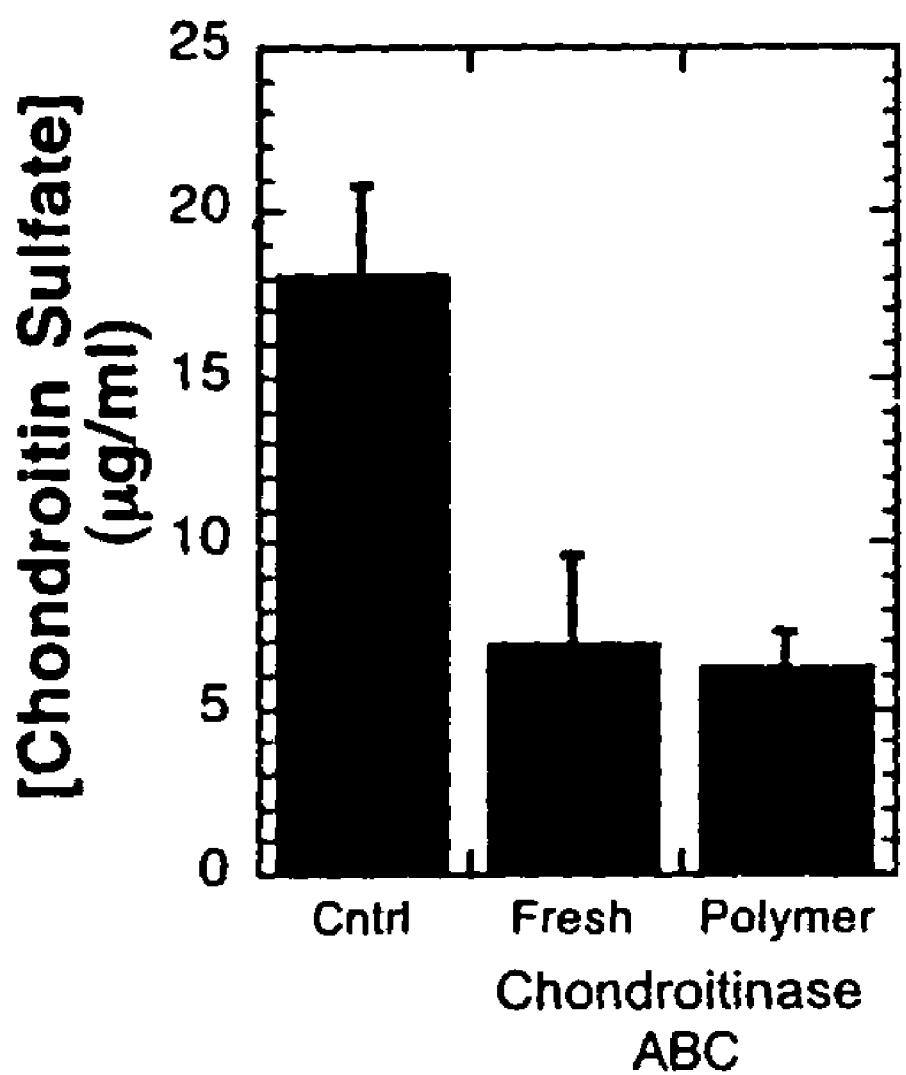

FIG. 8: Chondroitin sulfate concentration measurements using DMMB. Addition of chondroitinase ABC resulted in degradation of CS, with similar degradation observed for fresh and polymeric released enzyme.

Figure 9:
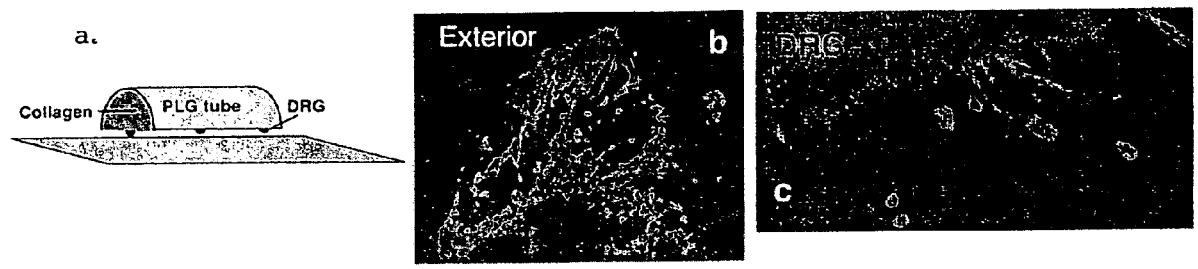

FIG. 9: (a) Schematic of an in vitro model for neurite outgrowth from DRG cultured within a PLG tube. Neurite outgrowth for DRG (b) near tube edge in which NGF is provided in the media and (c) at the center of the tube in which the NGF is released from the tube.

Figure 10:
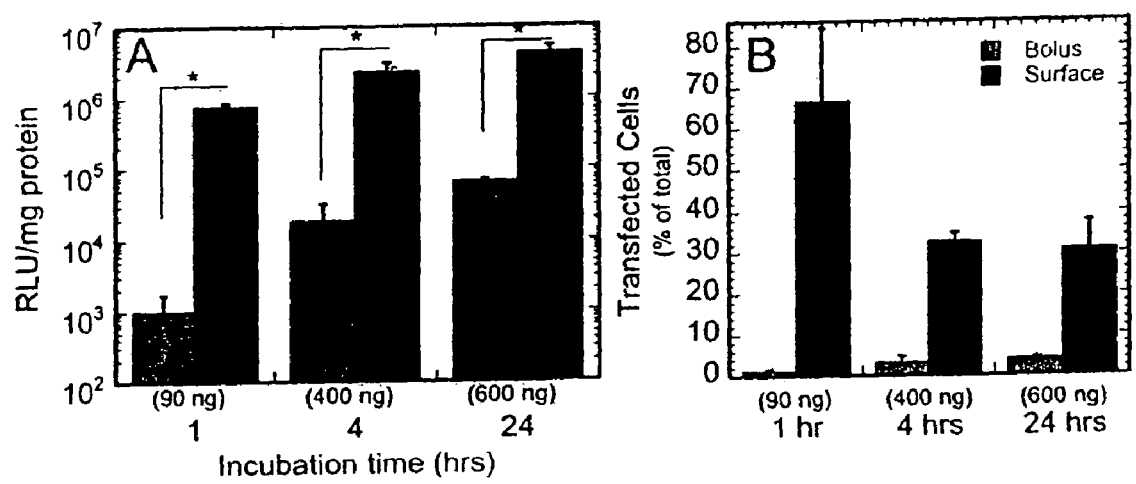

FIG. 10: The extent of transgene expression (A) and the number of transfected cells (B). Complexes formed at N/P equal to 6.

Figure 11:
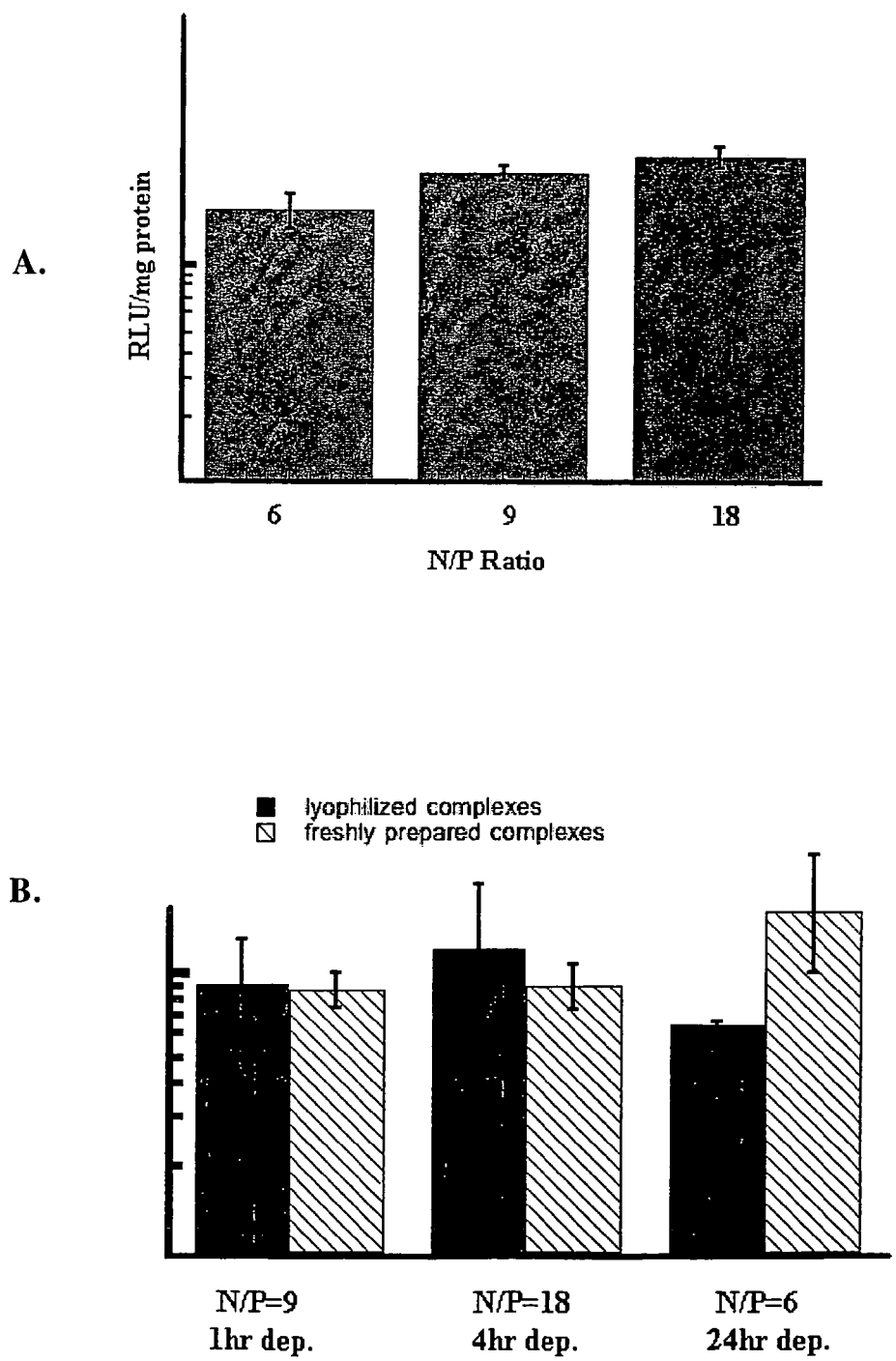

FIG. 11: (A) Transgene expression of luciferase by culture of cells on 3-dimensional porous PLG scaffolds. (B) DNA complexes retain the ability to transfect cells following lyophilization, which is similar to freshly prepared complexes.

Figure 12:
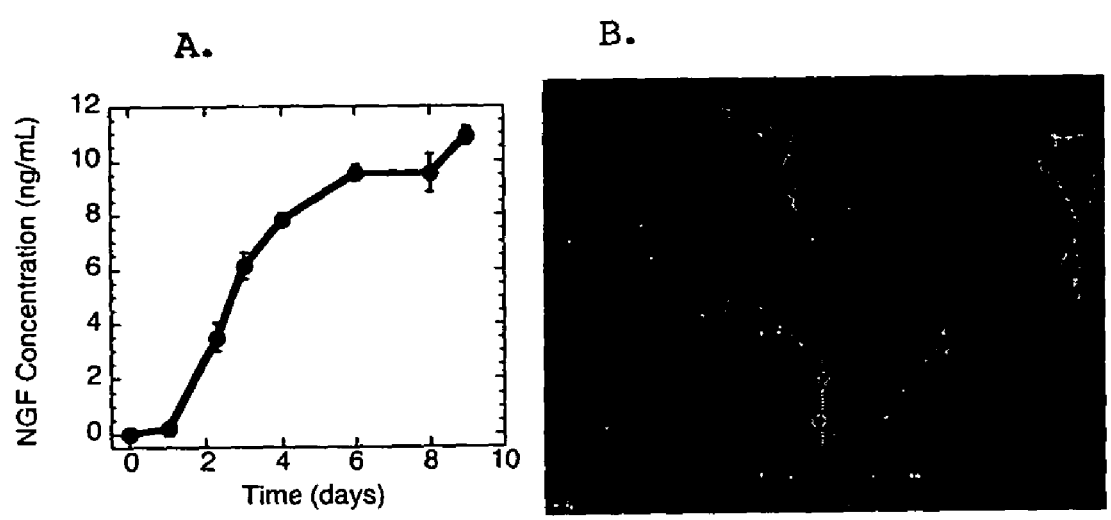

FIG. 12: (A) NGF concentration in media following transfection of PC12 cells with polymer released complexes. (B) Neurite extension by primary neurons co-cultured with 3T3 fibroblasts transfected with polymer released complexes encoding for NGF. Nuclei of all cells are labeled with Hoechst dye, while neurons are labeled with a neuron specific antibody to β-tubulin.

Figure 13:
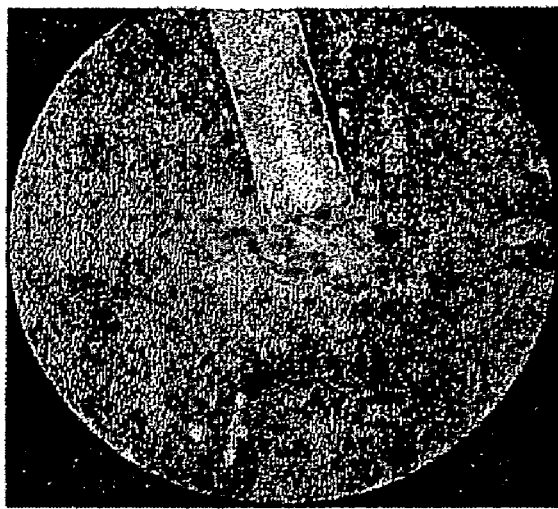
Figure 13:
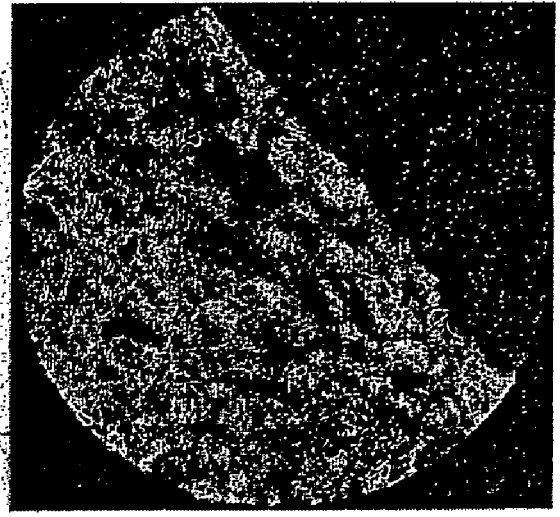

FIG. 13: (A) Photomicrograph of polymeric tube implanted into the injured spinal cord. (B) Fluorescence photomicrograph of lumbar dorsal root ganglion following 2-week implantation in vivo and staining with Fluorogold.

Figure 14:
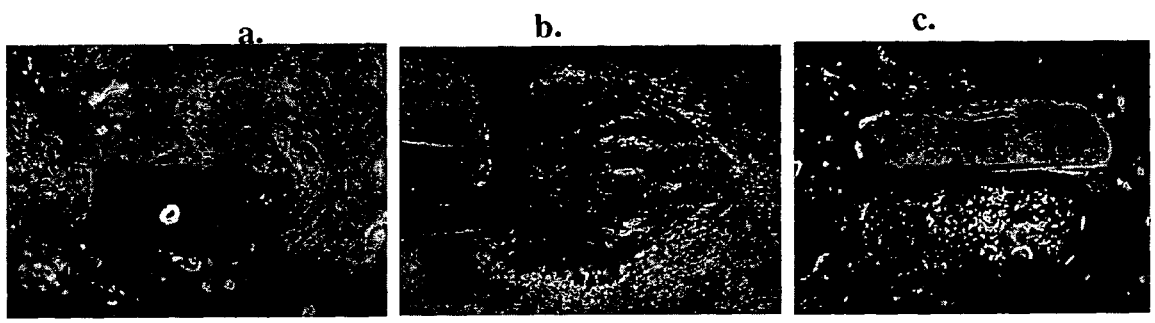

FIG. 14. Photomicrograph of spinal cord with implanted PLG scaffolds following 8-day implantation in vivo. Pictures are from 2 different spinal cords and are representative of the study (n=10). (a) is a hemi-section model showing a cavity formed in the spinal cord. (b) is a wide view and (c) is a close view of multi-lumen scaffolds (arrows) inserted into the spinal cord (*), with channels running from left to right.

Figure 15:
Figure 15:
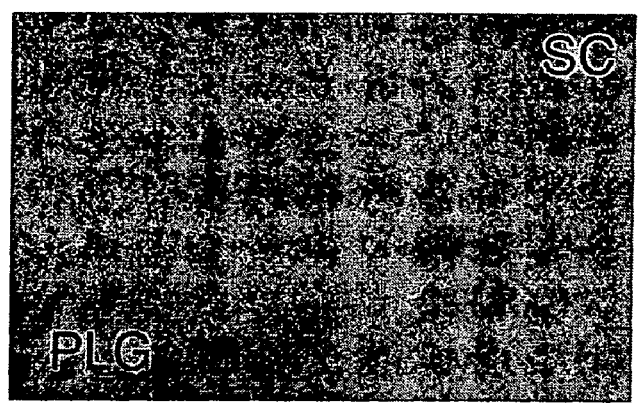

FIG. 15. Photomicrograph of spinal cord with implanted PLG scaffolds following 8 day implantation in vivo.

Figure 16:
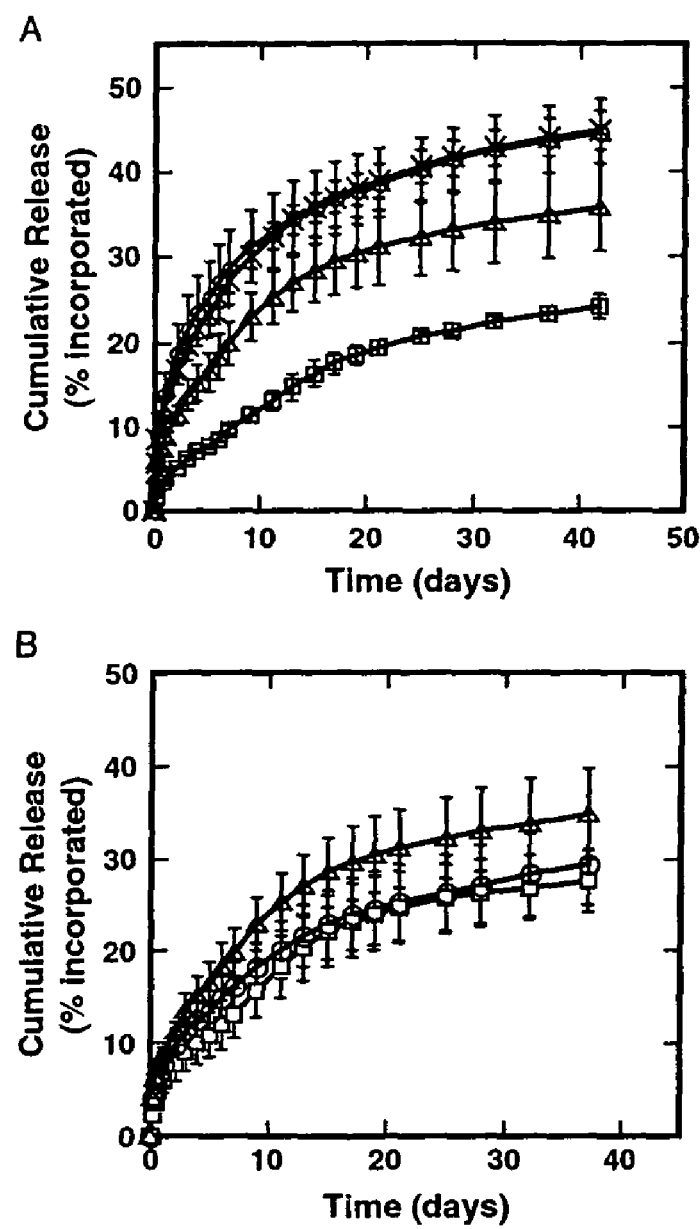

FIG. 16. NGF release from single lumen conduits. (A) Release of NGF from conduits fabricated with differing PLG composition and variations in the incorporation method (microsphere encapsulated, mixed with microspheres). □—100% HMW PLG, encapsulated NGF; ∆—75% HMW/25% LMW PLG, encapsulated NGF; ○—100% HMW PLG, mixed NGF; ×—75% HMW/25% LMW PLG, mixed NGF. Conduits were fabricated with porogen to polymer ratio of 5:1. A statistically significant difference was observed between encapsulated and mixed NGF for both 100% HMW condition and 75% HMW/25% LMW conditions (p<0.05). No statistical difference was obtained between the 100% HMW and 75% HMW/25% LMW for mixed NGF conditions (p>0.1). However, there is significant difference for the encapsulated NGF conditions (p<0.05). (B) Release curves for porogen to polymer ratios of 2:1 (□), 5:1 (∆), and 10:1 (○). Conduits were fabricated with 75% HMW/25% LMW PLG and encapsulated NGF. No statistical difference was obtained among conditions with various porogen to polymer ratios (p>0.05).

Figure 17:
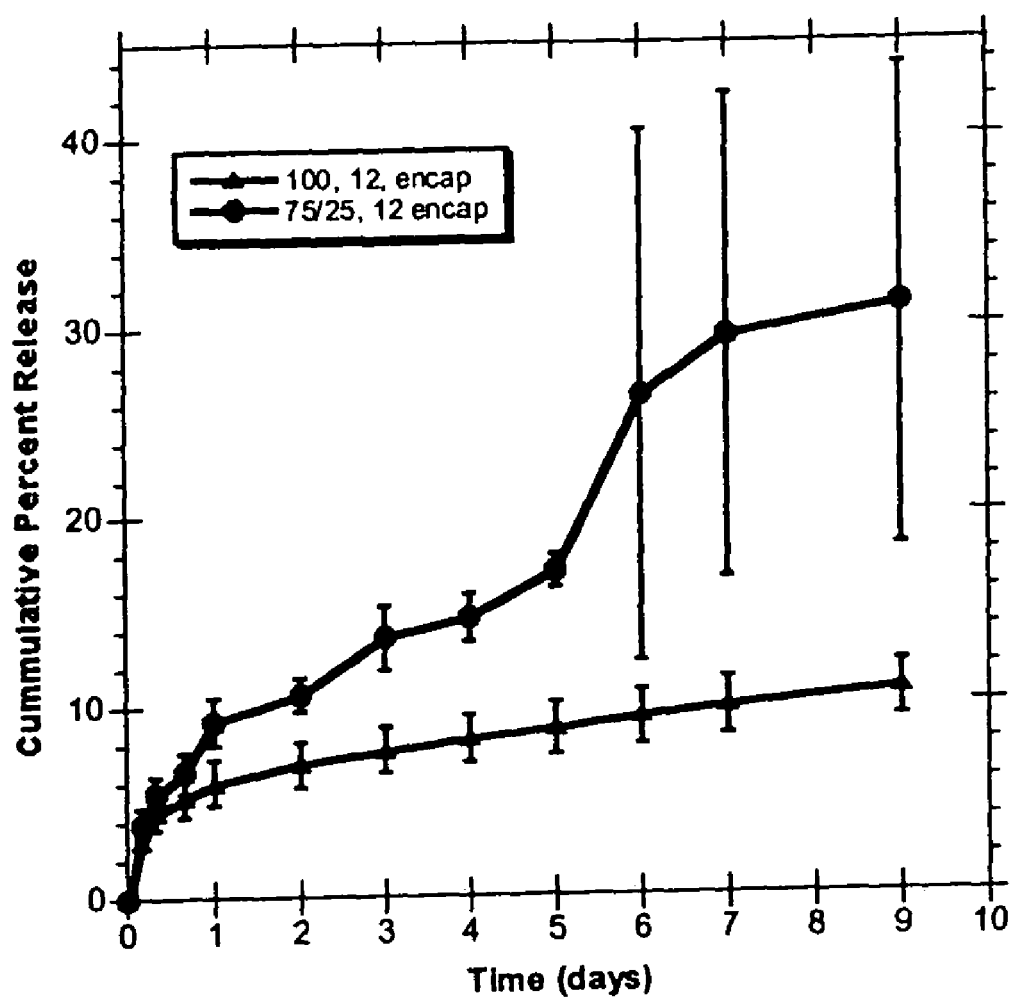

FIG. 17. Release kinetics of encapsulated I-125 NGF from multi lumen tubes fabricated from 100% high MW PLG, or 75% high MW PLG/25% low MW PLG. Homogenizer speed was kept constant at 7000 RPM and salt to polymer ratio was kept constant at 12 to 1.

Figure 18:
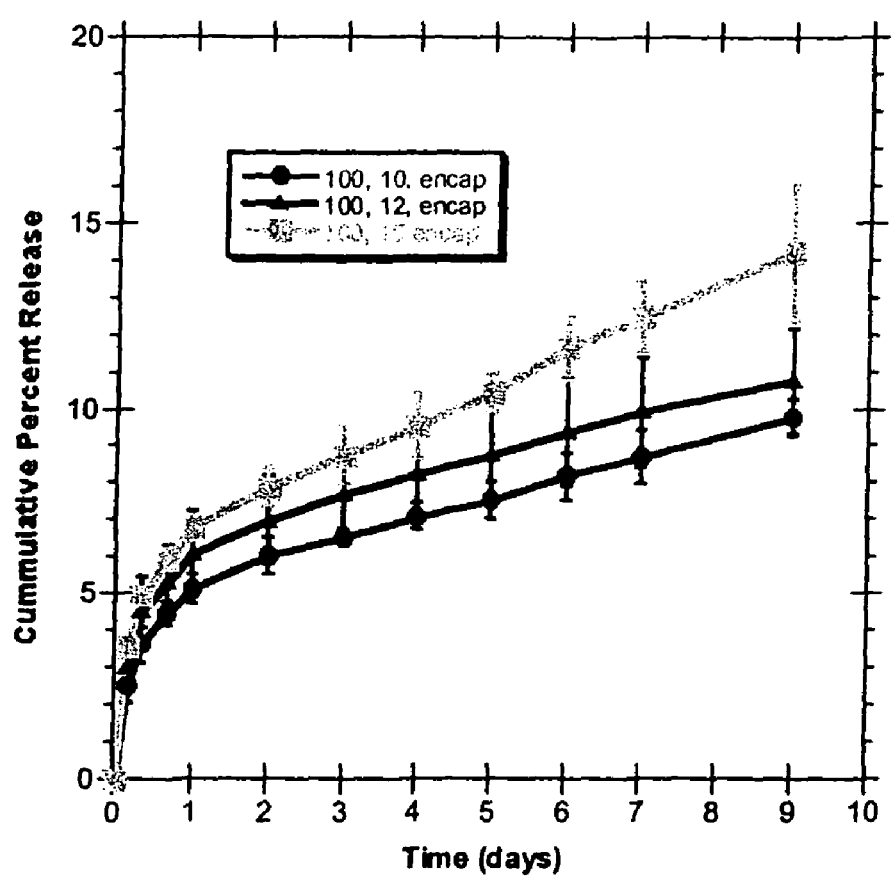

FIG. 18. Release kinetics of encapsulated I-125 NGF from multi lumen tubes fabricated from 100% high MW PLG, and salt to polymer ratio of 10 to 1, 12 to 1, and 15 to 1. Homogenizer speed was kept constant at 7000 RPM.

Figure 19:
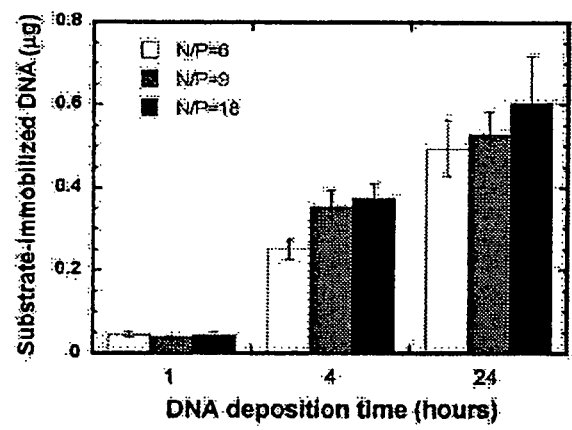
Figure 19:
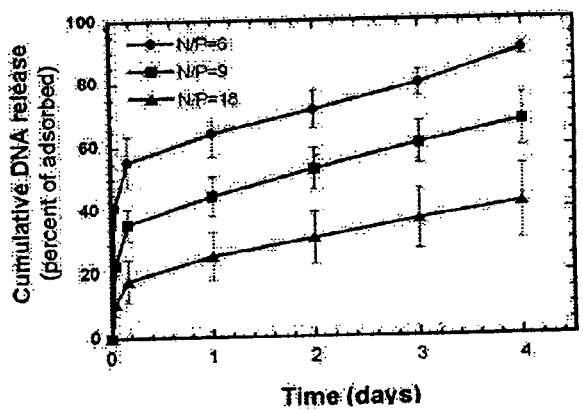
Figure 19:
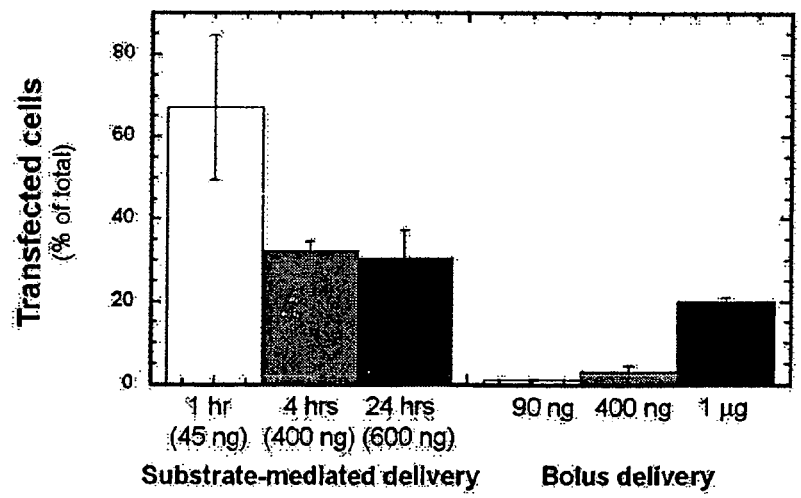
Figure 20:
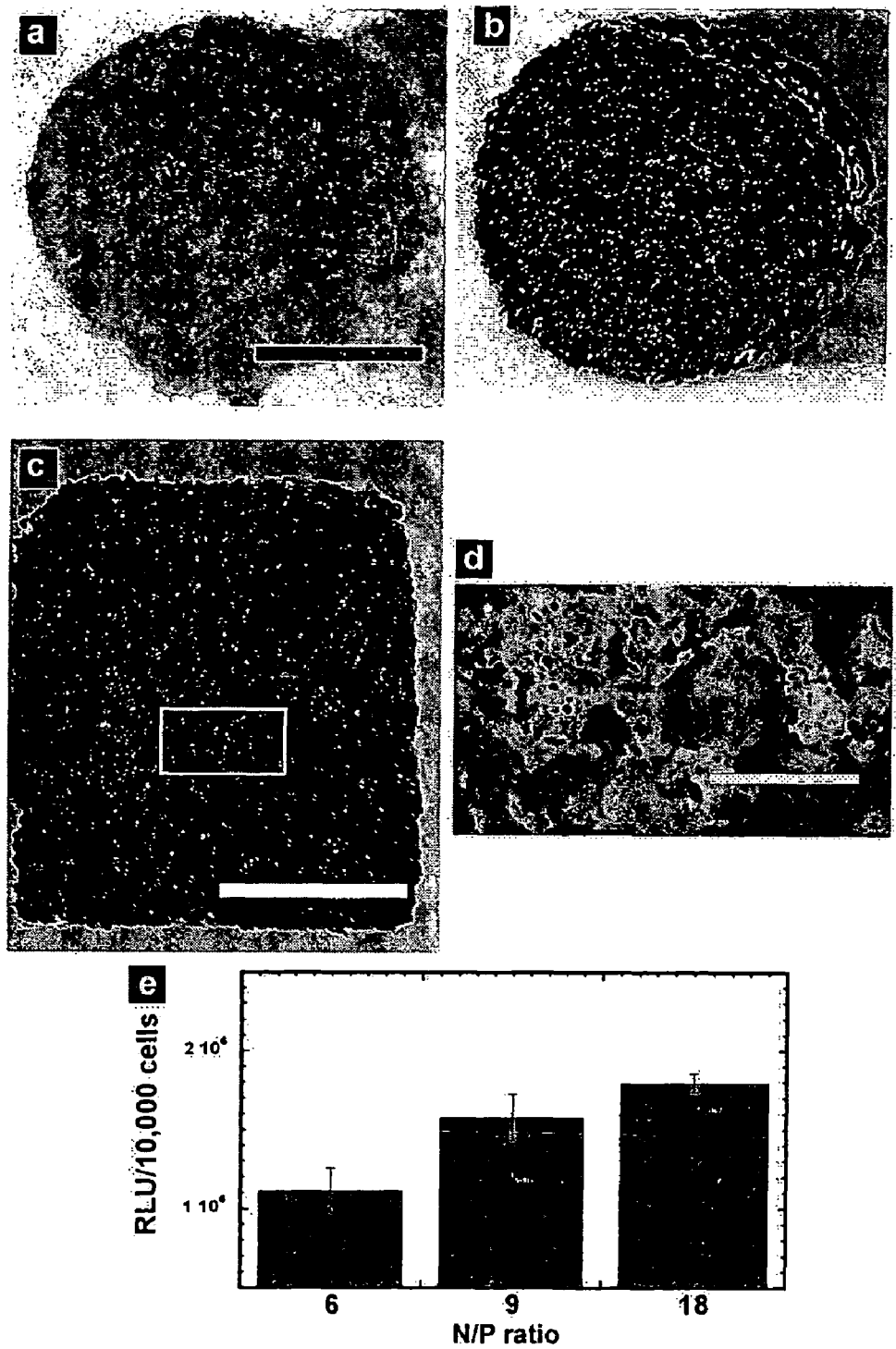

FIG. 19. PLG disks for DNA complex adsorption and release. a) Quantity of immobilized PEI/DNA complexes formed at N/P ratios equal to 6, 9 and 18. Data are represented as the average ±S.D. b) Cumulative release of adsorbed complexes from PLG disks. c) percentage of transfected cells by substrate-mediated from PLG disks and bolus delivery of complexes (N/P=9). For substrate-mediated delivery, the deposition time and approximate DNA quantities are shown in parentheses FIG. 20. Transgene expression within porous PLG scaffolds. X-gal staining of HEK293T cells seeded within the scaffold containing (a) no DNA or (b, c, d) DNA encoding for β galactosidase. Panels a and b provide a top view of the scaffold, whereas Panels c and d are cross-sectional views. Scale bars indicate 2.5 mm (a, c) and 200 μm (d), respectively. e, Transgene expression by immobilized complexes (initial loading: 50 μg) formed at N/P ratios=6, 9, 18.

Figure 21:
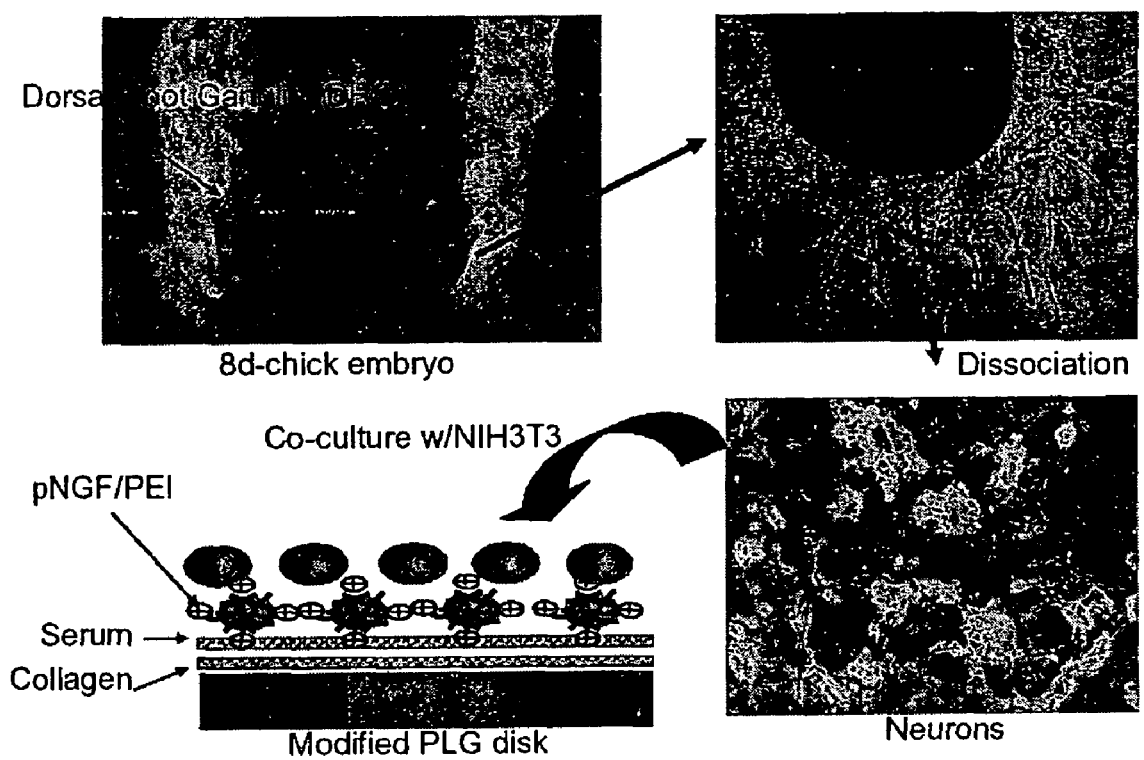

FIG. 21. Neurite outgrowth model

Figure 22:
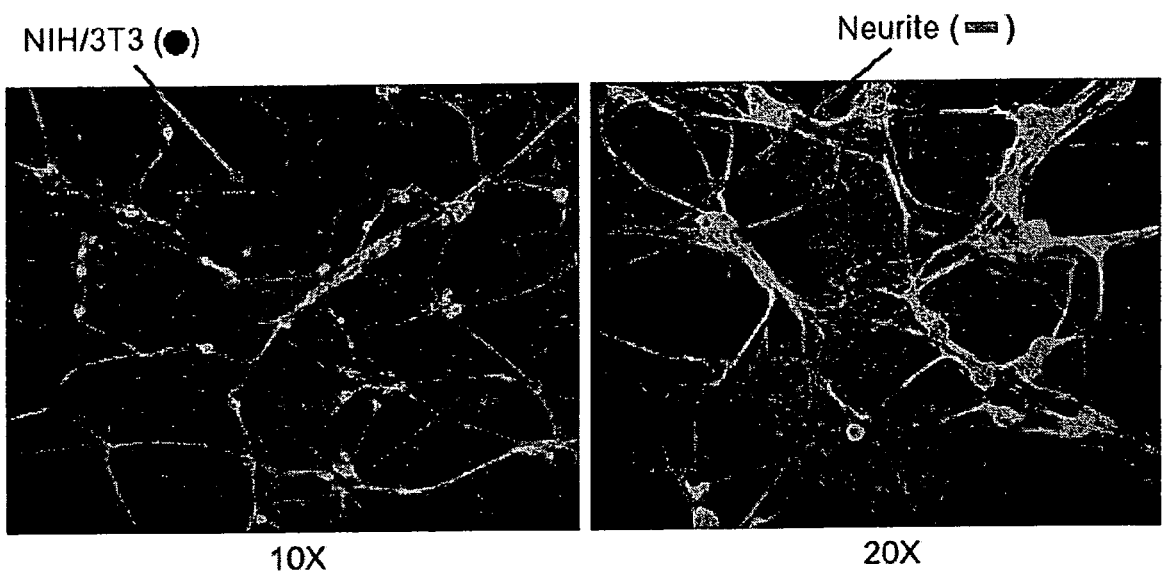

FIG. 22. Neurite outgrowth on PLG.

Figure 23:
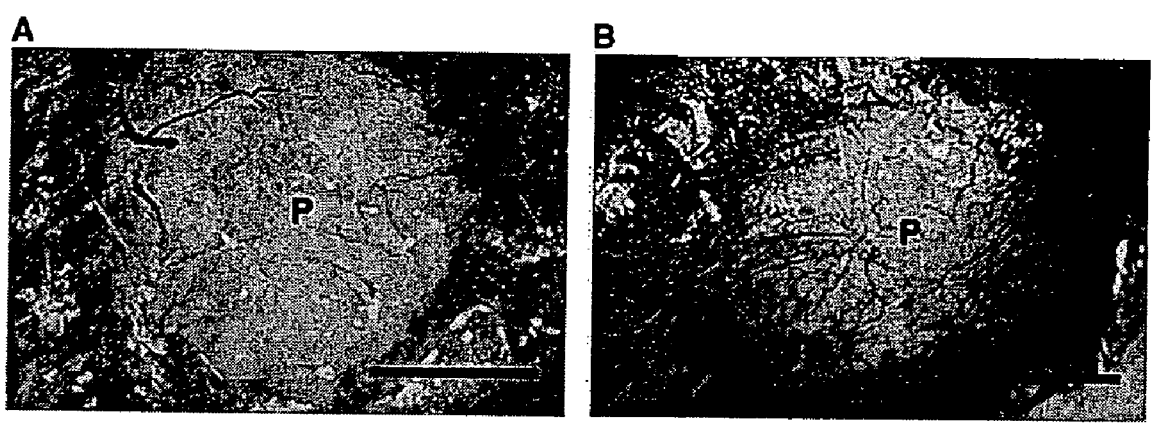

FIG. 23. Images demonstrating blood vessel formation on PLG scaffolds. Samples were retrieved 3 weeks postimplantation for (A) pLuc and (B) pVEGF. Scale bar, 2.5 mm.

Figure 24:
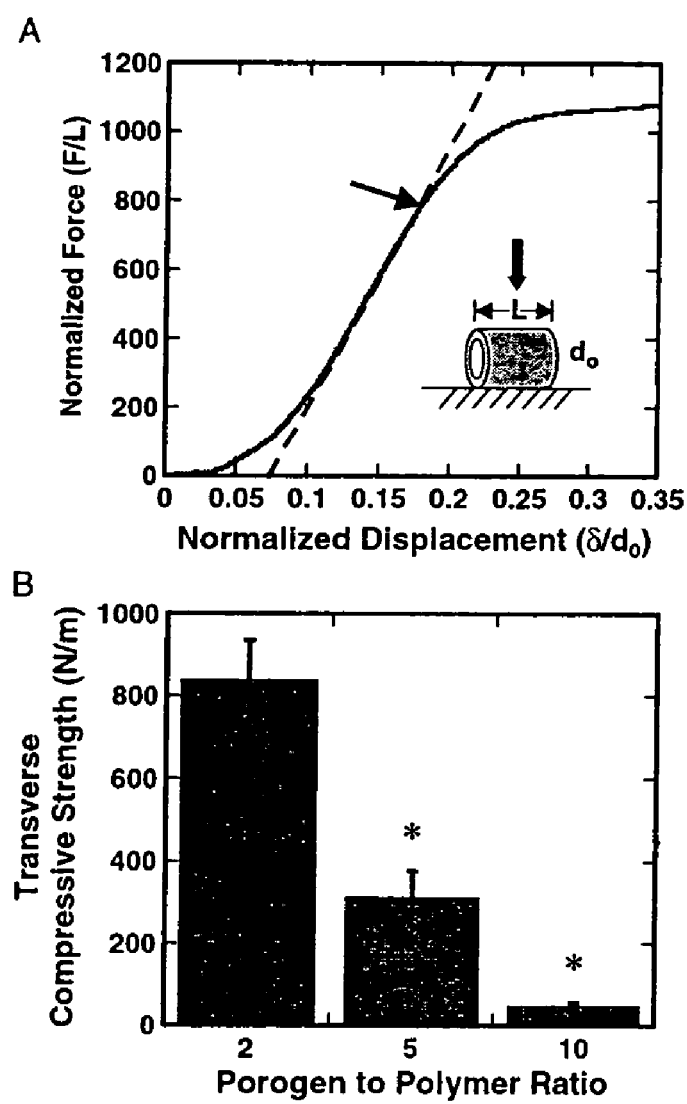

FIG. 24. Transverse compressive strength (Sc) of single lumen conduits. (A) Representative force-displacement curve for a conduit formed at a porogen to polymer ratio of 2:1. The dashed line represents a linear fit through the experimental data at the inflection point. (B) Transverse compressive strength for porogen to polymer ratios of 2:1, 5:1, and 10:1. Conduits were fabricated using HMW PLG. *Indicates statistically significant with p<0.01.

Figure 25:
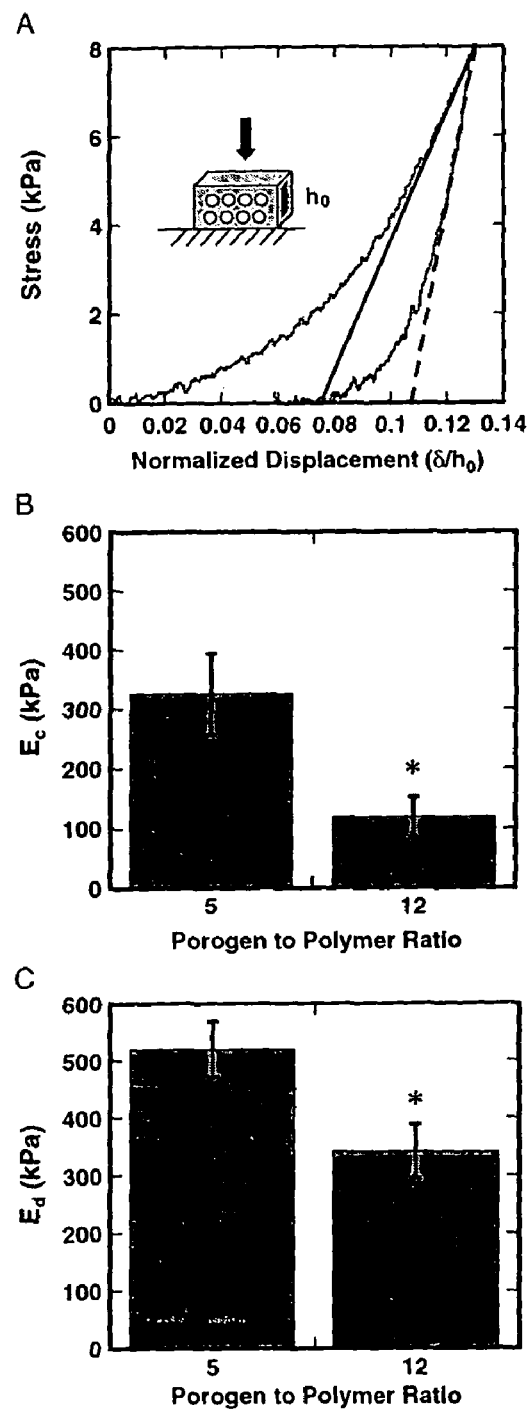

FIG. 25. Elastic modulus of multiple lumen conduits. (A) Representative compression and decompression curves for a conduit with porogen to polymer ratio of 12:1. Linear lines were fit to the compression (solid) and decompression (dashed) curve immediately adjacent to the apex. Elastic modulus for the compression curves (B) and decompression curves (C) of conduits with porogen to polymer ratios of 5 and 12. Conduits were fabricated with HMW PLG and 150 Am channels. *Indicates statistical significance of p<0.01 for the comparison.

Figure 26:
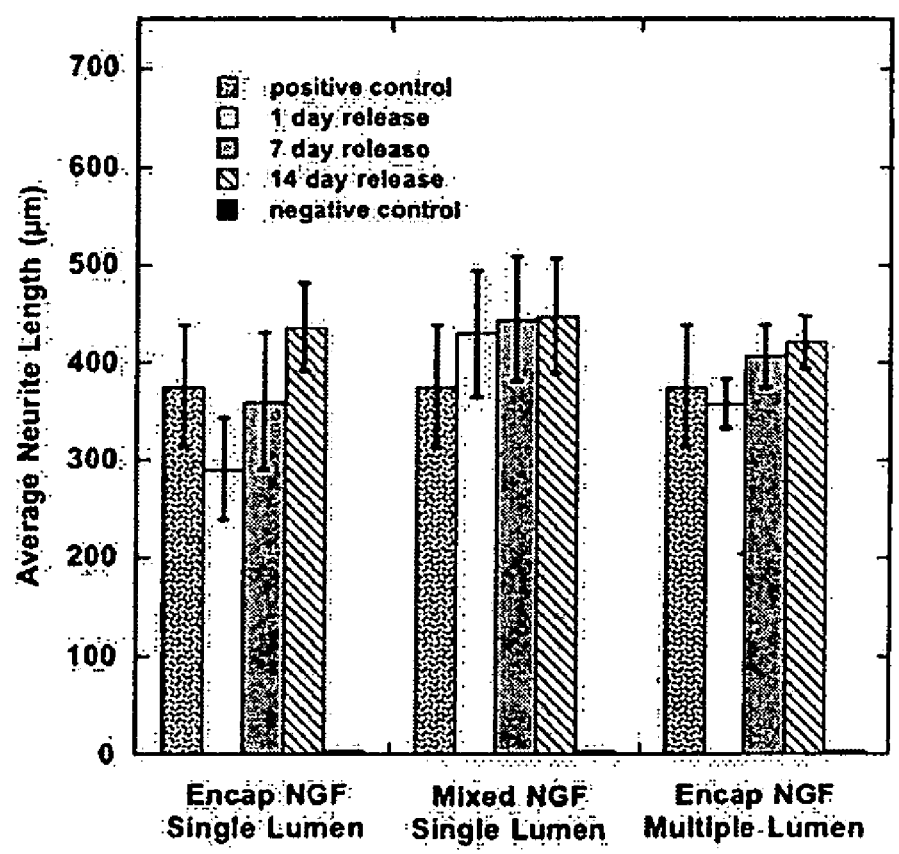

FIG. 26. Bioactivity of released NGF. Conditions tested include: single lumen conduit with encapsulated NGF, single lumen conduit with mixed NGF, and multiple lumen conduit with encapsulated NGF. NGF released at different time points was assayed for the ability to stimulate neurite extension by primary DRG neurons (n≧3). No statistical difference was obtained between the experimental and control conditions (p>0.05).

Figure 27:
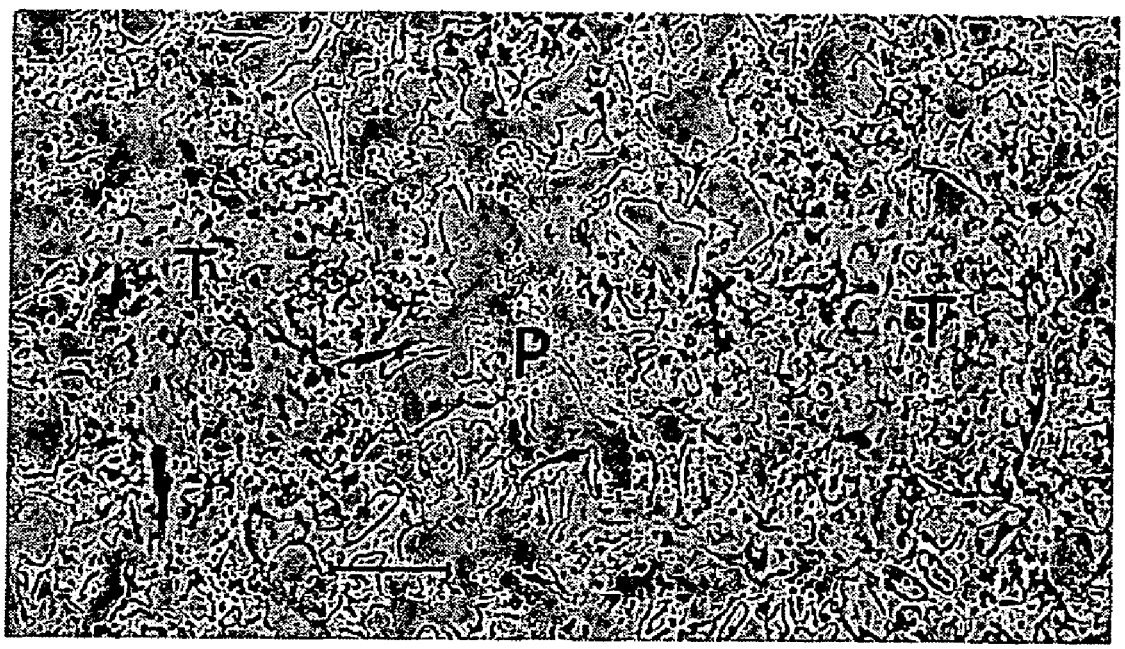

FIG. 27. Photomicrograph of in vivo retrieved scaffolds. Multiple lumen conduits (porogen to polymer=4:1) with 250 μm channels were implanted subcutaneously for 13 days. Sections (9 μm) were stained with hematoxylin and eosin and imaged under light microscopy (scale bar=100 μm). The labels T and P represent tissue and polymer, respectively.

Figure 28:
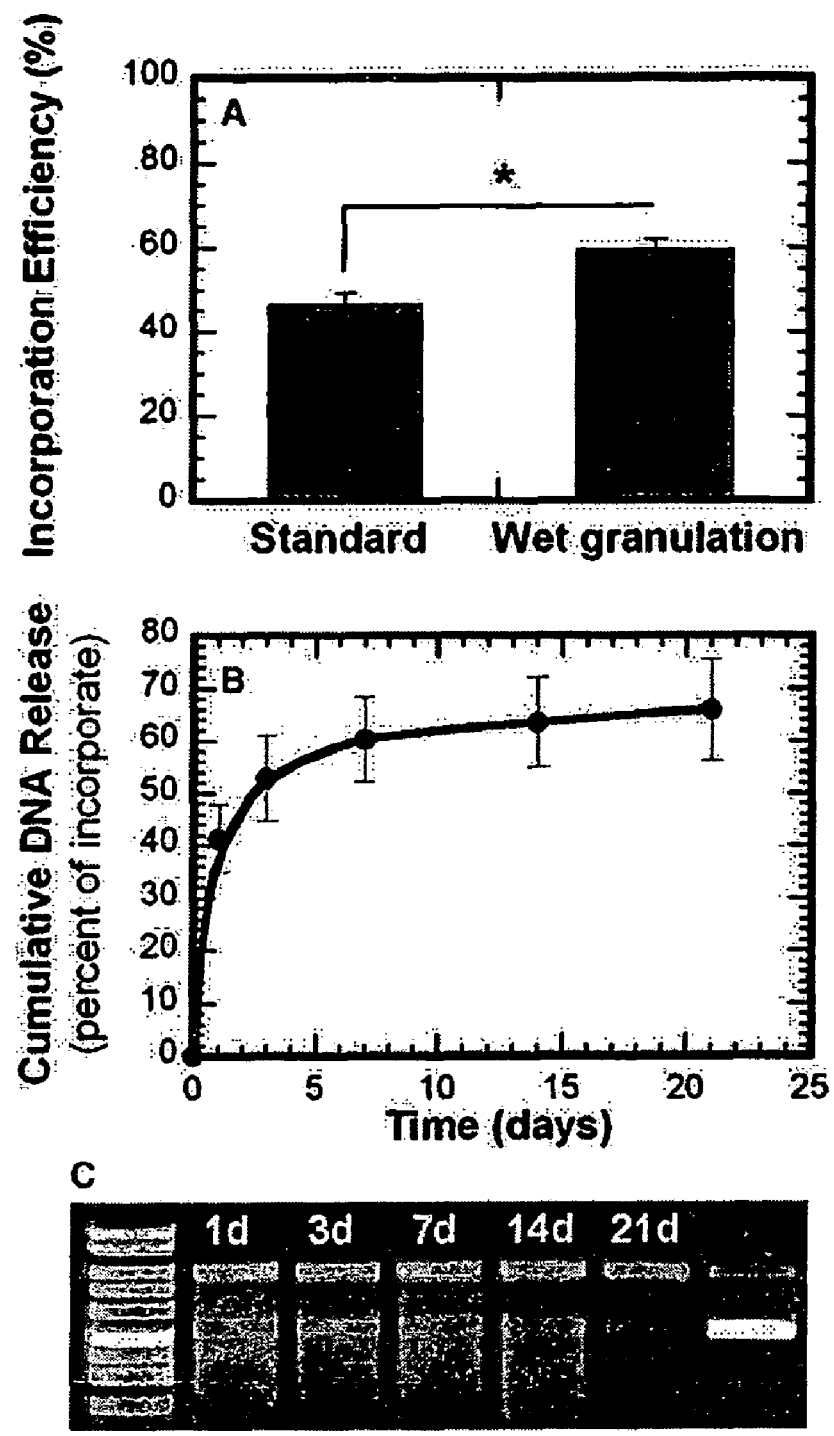

FIG. 28. Characterization of plasmid incorporation and release. (A) DNA incorporation efficiency with standard mixing and wet granulation. *Significant significance at P<0.001. (B) In vitro cumulative DNA release from scaffolds fabricated by wet granulation and subsequent gas foaming process. All the data in (A) and (B) were obtained after the leaching step. (C) Image of an agarose gel (0.8%) for plasmid released from scaffolds. Lane 1, molecular weight marker. Lanes 2-6, plasmid released at day 1, 3, 7, 14, and 21, respectively. Lane 7, unincorporated plasmid DNA.

Figure 29:
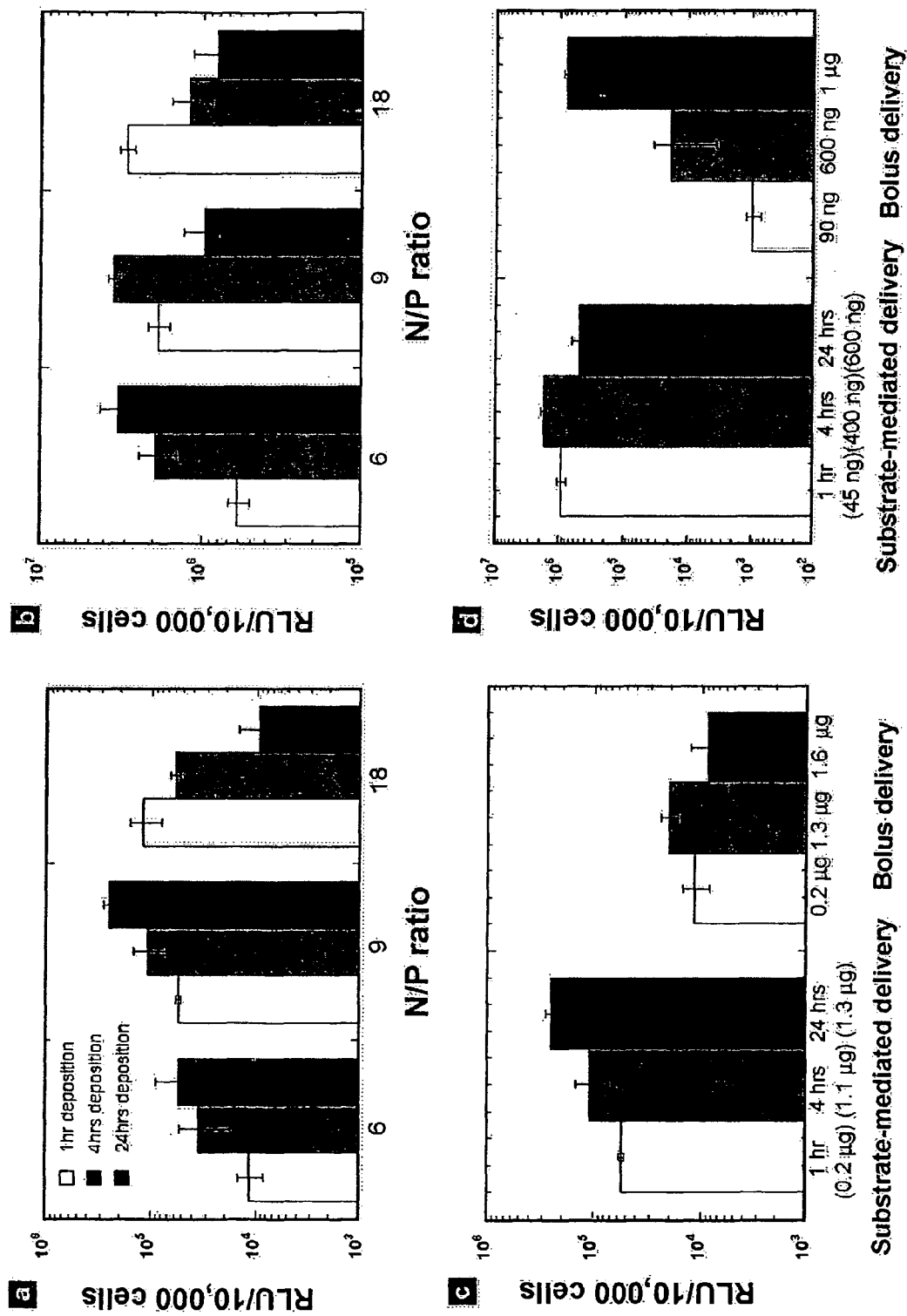

FIG. 29. Transgene expression by substrate-mediated delivery from PLG disks. Transgene expression for (a) NIH/3T3 and (b) HEK293T as a function of the N/P ratio and deposition time. Comparison of transgene expression by bolus and substrate-mediated delivery for similar DNA quantities in (c) NIH/3T3 and (d) HEK293T cells.

Figure 30:
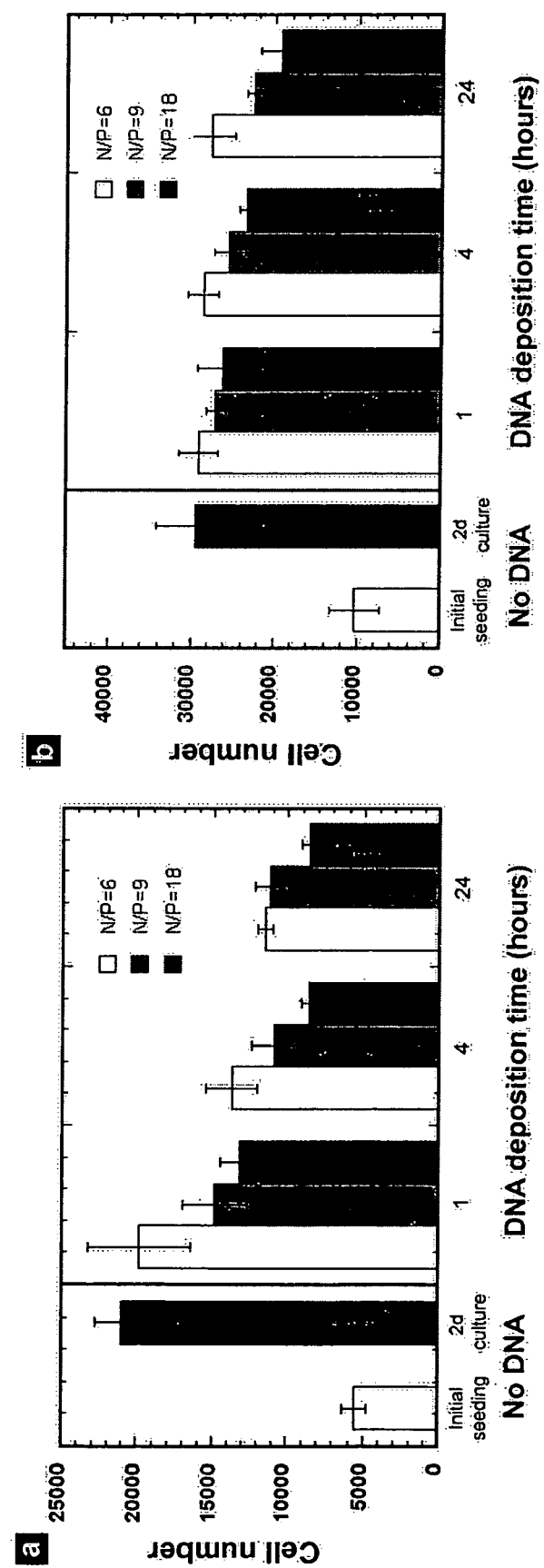

FIG. 30. Cell numbers on PLG disks. a) NIH/3T3 cells were seeded at a density of 10,000 cells well-1. b) HEK293T cells were seeded at a density of 20,000 cells well-1. Cell numbers were determined after 48-hr culture, with the exception of the initial seeding in which cell numbers were determined after 3-hr culture.

DETAILED DESCRIPTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

Definitions

The term "scaffold" as used herein, refers to a means of physical support for use in tissue engineering or tissue regeneration. The scaffold may be fabricated using various polymeric materials and may be molded in any shape suitable for its intended use, for example, as tubes, disks, sheets, sutures or any other shape suitable for use.

A "nerve guidance channel" or "conduit" or "tube" or "cylinder" refers to a polymeric material fabricated as a tubular prosthesis for use in nerve tissue regeneration. It may contain a single lumen or a plurality of lumens. It permits the damaged or severed ends of a nerve to be gently drawn into proximity and secured in place without undo trauma. It may also serve to retard infiltration of scar-forming connective tissue.

A "porogen" refers to any pore generating material, such as, but not limited to, for example, salt particles or sucrose granules.

"Gas foaming" as used herein refers to the use of a high pressure gas atmosphere for dissolving gas in a polymer. A thermodynamic instability is created, for example, by reduction in pressure, so that the dissolved gas nucleates and forms gas pores within the polymer. The procedure for "gas foaming", as used herein, is described in detail in U.S. Pat. Nos. 6,281,256 and 6,797,738, incorporated herein by reference in their entireties.

"Particulate leaching" refers to a procedure by which additional pores are created in the polymer matrix by addition of a particulate material into the polymer matrix. Upon leaching of the material from the polymer material, additional pores are formed within the matrix. Preferred leachable particulates are any particulate material which can be leached from the polymer matrix with a leaching agent. The preferred leachable particulates include salts that are soluble in an aqueous medium. The procedure for "particulate leaching", as used herein, is described in detail in U.S. Pat. Nos. 6,281,256 and 6,797,738, incorporated herein by reference in their entireties.

"Wet granulation", as used herein, refers to the addition of an aqueous material to a solid material to aid in preparation of a more homogeneous and consistent mixture with no agglomeration. The procedure also improves the flowability of the polymeric matrices to allow for ease in preparing molds having greater contours, such as the nerve guidance channels described herein. The wet granulation process also reduces the static charge of the polymer mixture, and therefore reduces the loss of material during the fabrication process.

"Growth factor" as used herein includes any factor recognized for its ability to promote growth of a particular cell type or tissue, and includes any active analog, active fragment, or active derivatives thereof. "Trophic factors" are factors desirable for growth and survival of various classes of cells in tissues. Both growth factors and trophic factors are generally macromolecular proteins.

"Guided tissue regeneration" as used herein, refers to the ability of the scaffolds containing the polymer matrices to aid in directed growth of a tissue, as opposed to a random growth of the tissue. For example, this "guided tissue regeneration" is most relevant when used to described the growth of nerve fibers or nerve tissue through the lumen(s) of the nerve guidance channels, as described herein.

"Tissue engineering" refers to the development of biological substitutes for implantation into the body or the fostering of tissue remodeling for the purpose of replacing, repairing, regenerating, reconstructing, or enhancing function of a tissue damaged by injury or disease.

The term "about" means within 20%, preferably within 10%, and more preferably within 5%.

A "vector" is a DNA molecule, capable of replication in a host organism, into which a gene is inserted to construct a recombinant DNA molecule.

The term "fragment" refers to either a protein or polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

"Analog" as used herein, refers to a nucleotide, a protein, or a polypeptide that possesses similar or identical activity or function(s) as the nucleotide, protein or polypeptide having the desired activity and therapeutic effect of the present invention (eg. growth or trophic factors to be incorporated into the scaffolds), but need not necessarily comprise a sequence that is similar or identical to the sequences of the preferred embodiments, such as that of SEQ ID NOS: 1-12 or possess a structure that is similar or identical to that of SEQ ID NOS: 1-12. As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues) of the AAPI; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quarternary structure as that of. the preferred embodiment (eg. SEQ ID NO: 1-12). The structure of a polypeptide can determined by methods known to those skilled in the art, including but not limited to, X-ray crystallography, nuclear magnetic resonance, and crystallographic electron microscopy.

"PLG" refers to poly(D,L-lactide-co-glycolide). "PLGA" refers to a copolymer of D,L-lactide and glycolide. Poly(d,l-lactide-co-glycolide) (PLG) with 75:25 mole ratio of lactide to glycolide was obtained from Boehringer Ingelheim Chemical (Resomer 755, i.v.=0.6-0.8, 80-120 kDa; Resomer 752, i.v.=0.116-0.24, 11-24 kDa, Petersburg, Va.). Resomer 755 and Resomer 752 are referred to as "high molecular weight" (HMW) and "low molecular weight" (LMW), respectively.

"Small molecule" or "small organic molecule" is an organic compound (or organic compound complexed with an inorganic compound (e.g., metal)) that has a molecular weight of less than 3 kilodaltons, and preferably less than 1.5 kilodalton.

General Description

Polymer scaffolds serve a central role in the engineering of functional tissue replacements, for which the approaches have been divided into three categories: conductive, inductive, and cell transplantation. The conductive approach primarily assumes the scaffold as a structural support that allows tissue formation by creating and maintaining a three-dimensional space, providing a support for cell adhesion, and allowing cellular infiltration from the surrounding tissue. In the cell transplantation approach, progenitor cells can be delivered with the matrix to provide a cell population capable of regenerating the tissue. Alternatively, the inductive approach presumes that the scaffold can induce tissue formation, potentially be serving as a vehicle for the controlled release of tissue inductive factors. For example, the release of VEGF in combination with PDGF can induce a vascular network to develop within the polymer scaffold. Alternatively, the delivery of tissue-specific growth factors can induce differentiation of endogenous or transplanted progenitor cells into the appropriate cell type.

Scaffolds have been fabricated into tubular structures for a range of applications. Peripheral nerve and spinal cord regeneration have employed tubular biomaterials as guidance channels or bridges. These channels are fabricated from either natural or synthetic materials, and can bridge the injury site. The tube serves to mechanically support the damaged nerve, provide a continuous path that can direct axon outgrowth, and reduce infiltration of cells from the surrounding tissue. Tubes made out of materials such as silicone, ethylene vinyl co-acetate or copolymers of lactide and glycolide (PLG). Lumen of tube may be filled with matrigel or collagen to promote neurite extension. Alternatively, tubes are being developed as stents for arterial repair. Tubular constructs are also being developed for engineering of tissues such as trachea, and esophagus. Several neurotrophic factors (e.g., nerve growth factor (NGF), neurotrophin-3 (NT-3)) have been identified that enhance cell survival and stimulate axonal extension; however, they are not typically produced in sufficient quantities to stimulate regeneration. The localized delivery of these factors, either by a pump, polymeric delivery systems, transplantation of engineered cells, or delivery of DNA encoding for these factors have also been employed to promote neuronal survival and direct axon outgrowth following trauma. Soluble factors can act over large distances to provide either attractive or repulsive signals. Protein growth factors have been delivered locally, typically by injection or infusion with mixed results. Alternatively, cells that are genetically engineered ex-vivo to secrete neurotrophic factors can be transplanted into the injury site. Localized protein production can also be achieved by delivering DNA encoding for neurotrophic factors (NGF, NT-3, BDNF). Non-viral DNA systems are generally considered to be safe; however, strategies must be developed to enhance transfection. DNA is typically complexed with cationic polymers or lipids to enhance internalization and cellular trafficking. The complexation acts to protect the DNA from degradation and produces a complex with diameters of 50-100 nm that can be efficiently internalized by cells. An alternative approach to enhance non-viral gene delivery involves the sustained release from polymer scaffolds. Polymeric delivery is thought to enhance gene transfer through an increased local DNA concentration that is maintained and thus provides multiple opportunities for internalization.

The inventors of the present application have provided improvements over the existing technologies for the preparation of scaffolds for tissue engineering. In particular, the methods described herein provide for the fabrication of neural conduits (nerve guidance channels) with either single or multiple lumens capable of controlled protein delivery. Conduits were fabricated from the copolymers of lactide and glycolide (PLG) with the assembly and fusion of microspheres using a gas foaming/particulate leaching process, which includes a wet granulation step prior to gas foaming to improve the homogeneity of the mixture and fabrication of the desired geometries. The fabrication conditions were examined for their ability to determine the porosity, mechanical properties, and rate of protein release. In particular, the release rate was characterized for conduits formed by either (i) mixing protein with microspheres or (ii) encapsulating protein within microspheres, prior to gas foaming. The release studies employed nerve growth factor (NGF) as a model neurotrophic factor. The bioactivity of released NGF was assessed by the ability to stimulate neurite outgrowth from dorsal root ganglia.

In addition, the inventors of the present application have also determined that the polymer matrices prepared by a gas foaming/particulate leaching process combined with a wet granulation step prior to gas foaming resulted in improvements in gene transfer, more particularly, the sustained release of plasmid from porous tissue engineering scaffolds. Furthermore, the design parameters that regulate the extent and duration of transgene expression and the distribution of transfected cells were characterized and optimized.

Accordingly, scaffolds for plasmid incorporation and release were fabricated by a gas foaming/particulate leaching process, in which wet granulation was employed to increase the plasmid encapsulation and scaffold integrity relative to the standard processing without wet granulation. The quantity, duration, and location of transgene expression in vivo were monitored with a noninvasive imaging system. The distribution of transfected cells within and around the implanted scaffold was also examined by immunohistochemistry. Finally, the ability of transgene expression to induce physiological responses was investigated using an angiogenesis model, in which plasmid encoding VEGF was delivered.

The tissue engineering scaffolds and the procedures utilized to prepare the polymer matrices of the scaffolds described in the present application have demonstrated advantages over existing scaffolds and matrices. In particular, the inventors of the present application have shown that the inclusion of a wet granulation step prior to gas foaming/particulate leaching improves the homogeneity of the polymer matrix, as well as promotes the ease of preparation of scaffolds such as nerve conduits, for which a certain degree of pliability is necessary in order to aid in the implantation into the site of injury. Thus, the curvature of the scaffold may be adjusted to a greater degree when the wet granulation procedure is utilized prior to gas foaming/particulate leaching, as compared to the ability to prepare a curved scaffold without the addition of the wet granulation step. The need to do this is even greater when preparing nerve conduits, in that the material for implantation must assume the shape of the damaged or severed nerve. In addition, the inventors have found that particular ratios of high to low molecular weight PLG, when combined with the wet granulation step prior to gas foaming and particulate leaching results in both a pliable conduit, with the added advantage of retaining its shape after in vivo implantation.

There are a number of criteria that must be met in order for a scaffold to be appropriate for tissue engineering procedures. These include biocompatibility and biodegradability, non-immunogenicity, negligible toxicity, chemical and mechanical stability, processable into a variety of shapes, high porosity, suitable surface chemistry that provides for cell attachment, proliferation and differentiation, and appropriate mechanical properties to match the damaged tissue. In addition, a scaffold that allows for favorable interaction between cells and promotes delivery of growth factors holds several advantages over others. Furthermore, a nerve conduit, such as that described herein that has these properties in addition to having multiple lumens, as well as the ability for sustained release of growth or differentiation factors, holds greater promise for the ability of cells to grow in a three dimensional structure and in the correct alignment for nerve tissue repair. Accordingly, the scaffolds of the present invention meet these criteria and the methods and procedures for preparation of such tissue engineering scaffolds are provided herein.

Processes and Polymers for Preparation of Scaffolds

Several techniques have been used to fabricate polymers into porous matrices for tissue engineering applications, including solvent-casting/particulate leaching (SC/PL) (A. G. Mikos, A. J. Thorsen, L. A. Czerwonka, Y. Bao, and R. Langer, "Preparation and characterization of poly(L-lactic acid) foams," Polymer, 35, 1068-1077 (1994)); phase separation (H. Lo, M. S. Ponticiello, and K. W. Leong, "Fabrication of controlled release biodegradable foams by phase separation," Tissue Engineering, 1, 15-28 (1995)); fiber extrusion and fabric forming processing (J. F. Cavallaso, P. D. Kemp and K. H. Kraus, "Collagen Fabrics as Biomaterials," Biotechnology and Bioengineering, 43, p. 781-791 (1994)); and gas foaming. (D. J. Mooney, D. F. Baldwin, N. P. Suh, J. P. Vacanti, and R. Langer, "Novel approach to fabricate porous sponges of poly(D,L-lactic-co-glycolic acid) without the use of organic solvents," Biomaterials, 17, 1417-1422 (1996).) The solvent-casting/particulate leaching and phase separation approaches require the use of organic solvents. Residues of organic solvents which can remain in these polymers after processing may damage transplanted cells and nearby tissue, and inactivate many biologically active factors (e.g., growth factors) that one might wish to incorporate into the polymer matrix for controlled release. Fiber forming typically requires high temperatures (above the transition temperature of polymer), and is not amenable to processing amorphous polymers. The high temperatures used in this process would likely denature any biologically active molecules or kill cells that one might wish to incorporate into the matrix.

The gas foaming method (for example, of Mooney et al., cited above) provides a technique to fabricate highly porous matrices from poly(lactic-co-glycolic acid) (PLGA) using a high pressure gas that avoids the use of organic solvents and high temperatures. However, the technique typically yields a closed pore structure, which is disadvantageous in many applications of cell transplantation. In addition, a solid skin of polymer results on the exterior surface of the foamed matrix and this may lead to mass transport limitations.

Harris et al. (U.S. Pat. Nos. 6,281,256 and 6,797,728) describe a polymeric matrix which has two types of porosity, the first formed by a gas-foaming process and the second formed by the action of particulate leaching. The combination of these two porosity types can be regulated by the processing conditions and materials used to provide porous polymer materials with a range of advantageous properties. The porosity from particulate leaching results in interconnected pore structure materials having an open pore structure. According to this process, a mixture of polymer particles and a leachable particulate material is molded, optionally with compression, to a desired size and shape and are subject to a high pressure gas atmosphere so that the gas dissolves in the polymer. A thermodynamic instability is then created, for example, by reduction of the pressure, so that the dissolved gas nucleates and forms gas pores within the polymer. This causes expansion of the polymer particles, and as they expand they fuse, creating a continuous polymer matrix containing the particulate material. Finally, the particulate material is leached from the polymer with a leaching agent creating a further porosity. The process thus provides a combination of the processes of gas foaming (GF) to form pores and particulate leaching (PL) to form another type of porosity. Hence, the process can be termed as a GF/PL process as opposed to the known solvent-casting/particulate leaching (SC/PL) processes. Thus, the gas foaming/particulate leaching (GF/PL) procedure described in U.S. Pat. No. 6,281,256 and U.S. Pat. No. 6,797,738 has advantages over the solvent casting/particulate leaching (SC/PL) procedure. Since no solvents or high temperatures are used, it is likely that there are no deleterious effects on cells or proteins that may be incorporated into the matrix. In addition, the procedure allows for pores formed by the gas foaming and further porosity as a result of the particulate leaching procedure. The result is a continuous polymer matrix, that is, one which is interconnected and one which has an open pore structure.

While the GF/PL procedure results in a polymer matrix that exhibits a distinct and desirous interconnected and open pore structure, the lack of a wet granulation step makes it difficult to fabricate into appropriate shapes for implantation, particularly when there is a need for particular curvature. More importantly, the GF/PL procedure, while having certain advantages over the SC/PL procedure, does not allow for a particular pliability of the matrix for shaping into specific curvatures for use as a nerve conduit. The wet granulation step of the present invention, which is described by J. T. Carstensen (Pharmaceutical Principles of Solid Dosage Forms, CRC Press, 1993), when applied to the polymer matrix prior to gas foaming and particulate leaching, allows for the ability to mold the polymer matrix into particular curved shapes to allow for implantation into the site of the damaged nerve. In addition, the polymer maintains its ability to act as a matrix for sustained release of, for example, nerve growth or differentiation factors and for cell attachment in the context of multiple lumens. Furthermore, when the wet granulation step is used prior to GF/PL with specific ratios of low and high molecular weight PLG, as described herein, the result is a pliable matrix, which contains an interconnected open pore structure able to maintain its shape after in vivo implantation, and which is not susceptible to collapse after implantation.

According to the process used to prepare the polymer matrix for the scaffolds of the invention, a mixture of polymer particles and a leachable particulate material is mixed by a wet granulation step, then molded, optionally with compression, to a desired size and shape and are subject to a high pressure gas atmosphere so that the gas dissolves in the polymer; then a thermodynamic instability is created, for example by reduction of the pressure, so that the dissolved gas nucleates and forms gas pores within the polymer; this causes expansion of the polymer particles, and as they expand they fuse, creating a continuous polymer matrix containing the particulate material; finally, the particulate material is leached from the polymer with a leaching agent creating a further porosity. The process thus provides a novel combination of the processes of wet granulation (WG), gas foaming (GF) to form pores and particulate leaching (PL) to form another type of porosity.

The novel materials prepared by the process are characterized as having pores formed from gas foaming and pores formed by particulate leaching, the particulate leaching pores also being termed macropores, and having an appropriate pliability such that molding of the matrix into a curved structure such as a nerve guidance channel is more easily achieved, and further has sufficient material strength to resist compression upon in vivo implantation. Preferably, the porosity resulting from the particulate leaching, which can be controlled by the amount and size of the particulate among other factors, is such that it results in interconnections and, thus, an open pore structure. In one embodiment, the scaffold is prepared with a 50:50 mixture of low and high molecular weight PLG, which results in a scaffold having all of these desired characteristics.

While materials prepared by a GF/PL process can provide an interconnected pore matrix, the inventors have discovered that the materials prepared by the inventive wet granulation process prior to the gas foaming and particulate leaching process exhibit significantly advantageous properties over GF/PL prepared materials, such as the added advantage of being more easily molded into scaffolds having curvatures necessary for implantation to specific tissue sites, as well as added mechanical stability. In addition, these scaffolds maintain their ability to provide sustained release of protein, DNA or cells following in vivo implantation. Further, the materials exhibit improved compression resistance. For instance, depending on the ratio of porogen to polymer or on the ratio of high to low molecular weight polymer, for example, PLG, the materials according to the invention can be prepared to maximize the compression resistance to provide materials with a compression modulus of, for example, 50-500 kPa, and in one particular embodiment, 320 kPa, or higher. Comparative SC/PL prepared materials exhibit a compression modulus of about 159±130 kPa, and compared to the GF/PL process exhibits a compression modulus of about 250 kPa, in particular, 289 kPa.

While not intending to be bound by this theory, it is reasonably hypothesized that the improved mechanical properties, improved pliability, improved homogeneity and stronger matrix of the materials prepared by the inventors' GF/PL process with the inclusion of a wet granulation step prior to gas foaming result, at least in part, from greater uniformity of polymer distribution in the materials and/or greater uniformity in size and distribution of porosity in the materials. SC/PL prepared polymers will not have such a uniform pore structure because the solvent evaporates from the polymer in a non-uniform manner and thus the polymer concentration changes non-uniformly in the material. For instance, SC/PL materials typically have non-uniformity because as the solvent evaporates the polymer concentration increases at the bottom of the matrix, i.e. the area where the matrix touches the glass cover slip. In contrast, the GF/PL materials exhibit a very uniform pore structure indicating that the polymer foams uniformly throughout the particulate bed during the gas-foaming step. In contrast to the GF/PL materials, the GF/PL with the inclusion of the wet granulation step exhibits not only increased homogeneity of pore structure, but maintenance of the sustained release characteristics in addition to better flowability and a less likelihood of collapse upon implantation.

Alternatively, it is hypothesized that in the GF/PL process the mechanical properties may be enhanced by tensile alignment of the polymer chains may be occurring during the elongation which occurs during foaming. (Principles of Tissue Engineering, Academic Press, p. 264 (1997).

In any event, it is of great advantage in tissue engineering and other applications that the materials of the invention can be prepared for maximizing tensile strength, compression resistance, as well as flowability, since they can be handled and manipulated without mechanical breakdown more readily and survive better in the environment in which they are used without mechanical breakdown. Further, the materials of the invention with both types of porosity, preferably with interconnecting porosity, provide a unique and advantageous material for many applications. The process can provide materials with a total porosity of, for example, from above 0 to 97% or higher. Preferably, the total porosity ranges from 90-97%.

For the process, a mixture of polymer and particulate material is used. The mixture is preferably as uniform as possible and can be provided by conventional means. Preferably, the mixture is molded, for example by compression molding at room temperature or other suitable temperature to effect the molding, to the size and shape which is substantially the same as that desired for its ultimate use.

The polymer and particulate materials should be selected so that the particulate can be leached with a leaching agent which does not dissolve the polymer or otherwise adversely impact on the material. Polymers and particulates useful for the SC/PL and GF/PL processes discussed herein are generally useful for the wet granulation combined with GF/PL process of the invention. Further useful materials are discussed below.

Any polymer into which gas can be dissolved and pores formed thereby and in which a particulate can be incorporated and leached therefrom can be used in the process. It is preferred, to facilitate dissolution of the gas, that the polymer be an amorphous or predominantly amorphous polymer. However, if it is desired to use a crystalline polymer the crystallinity can be reduced to a level such that the gas can be dissolved therein and then the crystallinity restored after formation of the pores. Depending upon the application of the materials, the polymer may be selected to be biodegradable or non-biodegradable. For many applications, such as tissue engineering, the polymer preferably is biocompatible to the environment in which it is used. A preferred useful class of polymers are homopolymers and copolymers of lactic acid and glycolic acid, for example, poly (D,L-lactide-co-glycolide). (PLG), poly-L-lactic acid (PLLA), poly-D,L-lactic acid (PDLLA), polyglycolic acid (PGA) and copolymers of D,L-lactide and glycolide (PLGA), particularly with 50% or more of the lactide in the copolymer. Although under many conditions copolymers are preferred over homopolymers, homopolymers may be preferred in some circumstances. Other useful polymers, for example, are aliphatic polyesters, such as polyhydroxybutyrate, poly-ε-caprolactone. Further, polyanhydrides, polyphosphazines, polypeptides may be used.

Additionally, blends of different polymers may be used or polymers which contain other agents, particularly which effect the mechanical properties of the resulting matrix. For example, blends of differing PLGA polymers which have distinct properties can be used to take advantage of the properties of both. Also, other polymers can be blended with the PLGA polymers, particularly for modifying the mechanical properties thereof. For instance, a blend of a PLGA polymer and alginate material was found to provide a tougher matrix with greater elasticity and ability to withstand greater strain before breaking. Thus, it can be useful, depending on the application, to blend polymers which result in a matrix with better pliability and/or strength. Blends with materials which act as plasticizers, toughening agents or modifiers of other properties are, therefore, useful in the invention. These materials can either be polymers or smaller molecule agents which may act in a temporary manner and then diffuse from the matrix.

The polymer composition and molecular weight also have a large affect on the three dimensional matrices' porosity and mechanical properties. Copolymers of PLGA have been shown to foam to a much greater extent than either homopolymer PGA or PLLA. This finding is consistent with previous reports that the amorphous PLGA copolymers foam more than does the crystalline polymer PGA (Mooney et al., Biomaterials, 17, 1417-1422, 1996). This is likely due to an increased gas dissolution in amorphous polymers as compared to crystalline polymers (D. F. Baldwin et al., J.Eng. Mat. Tech., 117, 62, 1995; and D. W. Van Krevelen, Properties of Polymers, Elsevier Publ., 1976). The molecular weight of the polymer has a large effect on scaffold porosity. A polymer with a high molecular weight (large i.v.) did not form scaffolds with as high of porosity as the same polymer with a lower molecular weight. The longer polymer chains of the high molecular weight polymer likely entangle to a greater extent, thus providing a stronger resistance to expansion than the shorter polymer chains.

In one preferred embodiment, it was also determined that a mixture of high and low molecular weight PLG provided a matrix having the desired mechanical stability (due to the presence of the high molecular weight polymer) and optimal incorporation efficiency of the DNA, protein or drug (due to the presence of the low molecular weight polymer), and when used with the wet granulation step prior to gas foaming/particulate leaching, resulted in the added advantage of increased flowability. In another preferred embodiment, optimal results are achieved using a combination of low and high molecular weight PLG for use in nerve guidance channels, where neurite outgrowth is desired. They may be used alone for guided tissue regeneration or combined with growth or trophic factors or genes or vectors encoding these factors. More particularly, they may be utilized to deliver growth factors in a sustained, local manner to promote regeneration. In addition, they could be used to transplant cells directly to a site to promote tissue regeneration from these cells and interacting host cells.

The leachable particulate is any particulate material which can be leached from the polymer matrix with a leaching agent. Preferred are salts soluble in an aqueous medium, preferably water. As salts, NaCl, Na citrate, Na tartrate, and KCl are useful particulate materials. Other useful particulates leachable by dissolution include, for example, gelatin, collagen and alginate particulates. It is also possible to use particulates which are leachable by organic solvents where the solvent does not adversely effect the polymer, however, this is not preferred since such would mitigate the advantage of lack of need for an organic solvent and lack of residue in the product. As discussed above, the size of the particulate will affect the size of the pores formed upon leaching of the particulate. Although not limiting of the invention, it is preferred that the particulate has an average size of from 10 to 500 microns. This size will correspond approximately to the size of the pores formed by the leaching thereof.

A gas is dissolved in the polymer of the, preferably molded, mixture of polymer and particulate by subjecting the mixture to a pressurized atmosphere of a gas which is inert to the system and will dissolve in the polymer under suitable conditions. Suitable gases and conditions are known from other gas-foaming processes and they can generally be used herein. Preferred examples of suitable gas include $CO_2$, air, nitrogen, helium, neon, krypton, argon, xenon or oxygen. Also volatile liquids which provide a gas at the gas foaming temperature may be used, e.g. water. However, other gases or volatile liquids which form gases known to be useful as blowing agents may also be used. These include, for example, fluorinated, including perfluorinated, hydrocarbons. Preferred for these are aliphatic or cycloaliphatic fluorinated hydrocarbons of up to 8 carbon atoms such as trifluoromethane, difluoromethane, difluoroethane, tetrafluoroethane, heptafluoroethane, perfluoropropane, perfluorobutane, perfluorocyclobutane, perfluoropentane, perfluorohexane, perfluoroheptane, pefluorooctane, perfluorocyclopentane, perfluorocyclohexane, hexafluoropropane and heptafluoropropane. Sulfur hexafluoride may also be a useful blowing agent. Other known blowing agents include alkanes such as propane, butanes and pentanes; cycloalkanes and cycloalkenes such as cyclobutane, cyclopentene and cyclohexene; dialkyl ethers such as dimethyl ether, methyl ethyl ether and diethyl ether; cycloalkylene ethers such as furan; ketones such as acetone and methyl ethyl ketone; and carboxylates such as formic acid, acetic acid and propionic acid.

The pressure is selected to facilitate dissolution of gas into the polymer and will, thus, depend upon the gas used, the polymer used and the temperature. Pressures of from about 600 to 900 psi are generally useful for $CO_2$ and PLGA polymers, although not limiting on the invention. For example, gases at super- or sub-critical conditions can even be used. Furthermore, a volatile liquid which can be dissolved in the polymer and forms a gas upon imposition of the thermodynamic instability can be used. As an example, $CO_2$ can be dissolved in a mixture of poly[D,L-lactic-co-glycolic acid] polymer and NaCl particulate at a pressure of about 800 psi applied for about 48 hours to allow saturation.

The specific gas used in foaming can be a critical variable in production of porous matrices. The choice of gas used in foaming has a large effect on the final scaffold structure. $CO_2$ produced highly porous matrices, whereas $N_2$ and He led to no measurable pore formation. These results are consistent with a number of previous studies in which $CO_2$ has been used to create porous polymer structures (Mooney et al., Biomaterials, 17, 1417-1422, 1996). While the exact mechanism underlying this result is not known, the greater degree of foaming experienced with $CO_2$ as compared to both $N_2$ and He may be the result of a specific interaction between $CO_2$ and the carbonyl groups of PLGA (Kazarian et al., J. Am. Chem. Soc, 118, 1729-1736, 1996).

The gas equilibration time and pressure release rate affected the porosity and stability of the matrices, although not as strongly as the other variables.

In order to initiate nucleation of the dissolved gas and growth of gas pores in the material, a thermodynamic instability is created. This phenomenon is described for example by Park, Baldwin and Suh, "Effect of the Pressure Drop Rate on Cell Nucleation in Continuous Processing of Microcellular Polymers," Polymer Engineering and Science, 35, pp. 432-440 (1995). Preferably, this is done by lowering the pressure of the gas atmosphere, for example, down to atmospheric pressure over a short time period. The time period being, for example, from a few seconds to about 15 minutes. The gas phase separates from the polymer via pore nucleation and growth of the pores occurs through diffusion of gas into areas adjacent the nucleation sites. The pore growth in turn reduces the polymer density. Other methods for creating the instability, such as raising the temperature, may be used, but, are not preferred due to ease of processing. The pore structure and pore size of the gas pores formed will be a factor of, among others, the type of gas used, the amount of gas which will depend upon temperature and initial and final pressure of the gas atmosphere applied, the solubility of the gas in the particular polymer, the rate and type of pore nucleation and the diffusion rate of the gas through the polymer to the nuclei. These and other factors can be adjusted to provide gas pores of a suitable size. Sufficient gas should be dissolved to cause formation of a continuous polymer matrix when the polymer expands during gas pore growth.

As a result of the thermodynamic instability, pore nucleation and gas pore formation and expansion, the polymer containing the particulate material forms a continuous phase, i.e matrix, around the gas pores.

The particulate is leached from the polymer with a leaching agent. Useful as leaching agent is any agent which will leach, e.g., dissolve and remove, the particulate from the polymer. As discussed above, an aqueous-based leaching agent, particularly water, is preferred. The leaching of the particulate from the polymer forms the type of porosity, other than that formed by the gas-foaming, which as discussed above can provide for an interconnecting pore structure.

Wet Granulation

In general, the purpose of wet granulation is to either enlarge the particle size, to improve the particle shape, to make the surface of the particles hydrophilic (that is, to promote wetting and consequently disintegration and dissolution) and to promote compressibility (Carstensen, Pharmaceutical Principles of Solid Dosage Forms, Chapter 6)

When it is desirous to wet granulate a dry solid, a binder is added to the dry mixture, such that the particles are more or less glued together into spherical granules. The most common binders used are the modified starches. Older binders are acacia and gelatin, or combinations of the two. A standard protocol may call for the addition of one part of cornstarch to one part of cold water and a uniform suspension is then prepared by stirring. This may then be added to nine parts of boiling water such that a translucent gel forms. The order of addition of one to the other may be reversed. The starch paste which forms using either procedure will differ due to the temperature profile of the cornstarch. The starch paste is then added to the drug or polymer matrix and will start forming wet bridges between the particles. The wet paste is initially distributed unevenly, but rapidly equilibrates (Zoglio, M. A. (1975), J. Pharm. Sci. 64:1869; Zoglio, M. A. (1976), J. Pharm. Sci 65: 12054). When the granulation is dried, the actual bond is a function of how long the granulation was kneaded. A higher temperature of paste increases the hardness and disintegration time, due to the higher solids content of the binder bridges ((Pilpei, N. (1977), J. Pharm. Pharmacol. 26:24P). The paste may "soup out", that is, the liquid phase may become so large and the solid phase so small, that the solid phase no longer supports the liquid. Thus, it will turn into a suspension. Great care must be taken to monitor the temperature during granulation so as not to allow this to occur.

There are several advantages in wet granulation procedures over direct compression. In particular, the wetting properties are better, particularly in the case of hydrophobic substances. That is, the addition of the hydrophilic binder makes the surface of the hydrophobic drug or polymer more hydrophilic. This aids in both disintegration and dissolution. The content uniformity is better. And further, the particle size and shape are optimized.

The particle size of the granulation product is also a function of the amount of binder used (Carstensen, J. T. et al., (1978), Int. J. Pharm. 1:65).

Granulations are carried out in mixing equipment known as kneaders. Examples are the Hobart Mixers (small), the Sigma-type kneaders, and the high -intensity mixers (V-blenders with intensifier bars, lodige mixers with choppers, and bowl mixers with impellers. Granulation can also be carried out in fluid bed driers. Continuous methods have been suggested as an improvement over present day techniques. In this method, a granulating agent is melted and fluidized and pumped into a stream of the solid particles and essentially enrobes them.

After the end-point is reached, the granulation is discharged from the kneader and must be dried. This type of drying may be done in a tray dryer or by a vacuum dryer. Alternatively, it may be carried out in a fluid bed dryer (Travers, D. N. (1975), J. Pharm. Pharmacol. 27:516).

More recently, the microwave dryer has been successfully employed (VanScoik, K. M., (1991), In Encyclopedia of Pharmaceutical Technology, J. Swarbrick and J. C. Boylan, eds., New York, N.Y., Marcel Dekker, p. 494). The advantage here is that the temperature required is much lower.

As noted herein, the process for preparing the polymeric matrices to be used in the scaffolds for tissue engineering involves a wet granulation step prior to the use of gas foaming and particulate leaching to create the pores in the matrices. The advantages of using such a wet granulation step are evident from the present invention in that it allows for better uniformity of the matrix and allows for better flowability, which is important for the preparation of scaffolds having particular curvatures, such as that observed in the nerve guidance channels of the invention.

Therapeutic Uses of Scaffolds

The materials prepared by the process of the invention exhibit a wide range of utilities. They may be applied to any use which requires a porous polymeric material, particularly with an open pore structure. Further, the materials are particularly applicable for uses wherein organic solvent residue is not tolerable, e.g. in applications wherein biocompatability is desired. For instance, the materials are useful as matrices in which cells are compatible and grow to achieve their intended function, such as in tissue replacement, eventually replacing the matrix depending on its biodegradability. Furthermore, the materials can be used to provide matrices already bound to cells which may then be surgically implanted into a body. Further, the materials can be used as a sustained release drug delivery system, as wound healing matrix materials, as matrices for in vitro cell culture studies or uses similar thereto. The stable structure of the materials of the invention provide ideal cell culture conditions.

The materials of the invention prepared by the wet granulation plus GF/PL process generally further have applications similar to those of materials prepared by the GF/PL without wet granulation process and the SC/PL and phase separation techniques, for example, in a variety of cell transplantation applications, including for hepatocytes (D. J. Mooney, P. M. Kaufmann, K. Sano, K. M. McNamara, J. P. Vacanti, and R. Langer, "Transplantation of hepatocytes using porous biodegradable sponges," Transplantation Proceedings, 26, 3425-3426 (1994); D. J. Mooney, S. Park, P. M. Kaufmann, K. Sano, K. McNamara, J. P. Vacanti, and R. Langer, "Biodegradable sponges for hepatocyte transplantation," Journal of Biomedical Materials Research, 29, 959-965 (1995)), chondrocytes and osteoblasts. S. L. Ishaug, M. J. Yaszemski, R. Biciog, A. G. Mikos; "Osteoblast Function on Synthetic Biodegradable Polymers", J. of Biomed. Mat. Res., 28, p. 1445-1453 (1994). However, the materials of the invention have better mechanical properties and avoid the problem of organic solvent residue that may damage transplanted or migrating cells and nearby tissue and/or inactivate biologically active factors.

While any cell type may adhere to the matrix material, as an exemplary cell type, it has been shown that smooth muscle cells readily adhere to the matrix material of the invention and create three-dimensional tissues within these porous structures; thus, they provide a suitable environment for cell proliferation. In vitro experiments indicate concentrated cell growth around the periphery of the matrix. This is likely due to $O_2$ diffusion limitations to the cells at the center of the matrix because of the thickness (3.4 mm) of the sponge.

In addition, these matrices have a better potential to incorporate growth factors than those prepared using organic solvents. The potential problem with organic solvents is that residue remains in these polymers after processing may damage the transplanted cells and nearby tissue. Further, exposure to organic solvents would inactivate many biologically active factors. Currently, incorporation of growth factors with biomaterials are done using microspheres. This method also uses organic solvents during fabrication. This disadvantage can be eliminated with the matrix materials of the invention because the growth factor can be incorporated directly into the polymer matrix to obtain a better release. As shown herein, one example of such growth factor is a nerve growth factor.

One preferred manner of incorporating growth factors in a matrix for tissue engineering and/or cell proliferation is to provide a growth factor contained within a polymeric structure in particle form, e.g. as beads microspheres, or blended with another polymer or other molecules, before adding to the polymer, such as PLG or PLGA, for foaming. The polymeric structure can be formed of another copolymer of PLG or PLGA which degrades at a different rate than the PLG or PLGA utilized to form the bulk of the matrix or from a different polymer material, such as an alginate or modified alginate material. Such a system provides an additional level of control over the release kinetics of molecules from the matrices, and additional control over their bioactivity because the growth factors contained within the polymeric structure can be designed to provide a controlled release effect therefrom in addition to the release kinetics provided by the matrix. The release is this situation will likely be controlled by either disassociation of the factor from the bead, release from the PLG or PLGA, or both. Thus, a high degree of control over release kinetics is provided over a potentially wide range. Further, multiple factors can be included in a matrix (in multiple types of the described particles and/or in polymer comprising the bulk of matrix) which will release at varying times. This will be useful if a cascade of growth factor release, or waves of release of the same factor (e.g., for use in immunizations) is desired. Incorporation of the growth factors into these particles (e.g., alginate beads) is also more suitable for maintaining the long-term bioactivity of the factors than if they were immobilized directly in the polymer comprising the bulk of foamed matrix.

Highly porous matrices, for example, from PLG or PLGA, with a combination of gas foaming and particulate leaching can be prepared by the invention. The method avoids the use of organic solvents or high temperatures and yields materials with desirable pore structures. It is possible to control the porosity and pore structure of these matrices by varying the particulate polymer ratio and particulate particle size for example. These matrices exhibit enhanced mechanical properties, and can be utilized to form three-dimensional tissues.

This novel fabrication method can be used, for example, as an approach for drug and/or growth factor incorporation into polymers used as tissue engineering matrices.

Another useful application for the polymer matrices of the invention is for guided tissue regeneration (GTR), such as described in the Examples for nerve tissue regeneration. This application is based on the premise that progenitor cells responsible for tissue regeneration reside in the underlying healthy tissue and can be induced to migrate into a defect and regenerate the lost tissue. A critical feature of matrices for GTR is the transport of cells into the matrix, a property which is dictated by the pore size distribution and pore continuity, i.e., interconnectivity. The matrix must allow the desired cells to invade the matrix while preventing access to other cell types.

The materials of the invention, for example, a polymer sponge or a tubular scaffold made of PLG, poly(lactic acid) PLA, poly(glycolic acid) (PGA), or poly(lactic-co-glycolic acid) (PLGA), having an impermeable layer on one side can provide this selective permeability feature. The impermeable layer is composed of the same polymers but without the extent of porosity, and a variety of methods can be used to couple the impermeable layer to the polymeric sponge.

An impermeable layer can be created on one side of the sponge by one of the following techniques, preferably performed before gas foaming of the material. The sponge can be pressed into shape on a layer of PGA at a temperature greater than the melting temperature for PGA. The melted PGA will be able to adhere to the sponge thus forming a thin layer. This layer is impermeable because the foaming process and the leaching process have a negligible effect on pure PGA. An impermeable layer of PLGA can also be created on the sponge by pressing the sponge onto a layer of PLGA. Spraying a solution of PLA in chloroform onto one side of the sponge can also create an impermeable layer. Further, it is possible to use the same polymer material and alter the amount of leachable particulate in each section so that one section forms an open pore structure and one does not. Also, by using different polymers, materials wherein one section foams, and the impermeable layer section does not, can be provided. Although PLGA does foam following release of pressure from the bomb, an impermeable skin forms on the thin layer of PLGA which remains intact during the leaching process. Alternatively, following the foaming and leaching process, the polymeric sponge can be dipped in either melted PGA or in a solution of PLGA in chloroform. These procedures can be used to create a sponge which has a porosity of greater than 95% with an impermeable side.

Similar methods can be applied to analogous materials, as discussed above, to provide other sponge materials according to the invention useful for GTR applications.

The PLG or PLGA matrices also can provide a suitable substrate for bone formation. A critical feature of a matrix for replacement of bony tissues is its ability to provide an appropriate environment for tissue development and matrix mineralization.

A critical feature of the matrix for use in guided nerve tissue regeneration is the ability of cells to migrate into the matrix and for cells expressing growth factors to promote neurite extension through the tube. Previous experiments confirm cells readily migrated into and throughout the matrix in vitro. The studies presented herein provide proof that the incorporation of a nerve growth factor or a DNA encoding such factor actually promotes neurite extension in the scaffold.

Another potential application of these sponge materials for GTR is for the treatment of periodontal disease. Periodontal disease is characterized by the loss of attachment of the periodontal ligament to the alveolar bone. The epithelial cells of the gingiva begin to grow into the site where the periodontal ligament was attached. A sponge of the matrix material according to the invention with an impermeable side could be used to prevent the downgrowth of epithelial cells while allowing the appropriate cells to occupy the porous sponge thereby regenerating the periodontal ligament. Further guidance as to such application is provided by Shea et al., Tissue Engineering: Fundamentals and Concepts, Chapter III.6, "Biodegradable Polymer Matrices in Dental Tissue Engineering."

For other applications in which cells are seeded or otherwise incorporated and grown within the inventive matrices, incorporation and growth of the cells can be facilitated in a manner known in the art. Examples of such methods are provided in U.S. Pat. Nos. 5,041,138; 5,567,612; 5,696,175 and 5,709,854; all of which are incorporated herein by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Suitable Growth or Tropic Factors for Delivery to the Site of Injury

Suitable growth factors for use with the present invention may include any that are known to induce cellular proliferation or differentiation for the tissue in need of repair. For example, when a scaffold is to be fabricated as a nerve conduit, it is desirous to incorporate into or attach to the nerve guidance channel a nerve growth factor such as NGF2, NT3, BDNF, GDNF, FGF1, FGF2, VEGF, PDGF, PEDF, angiopoietin and erythropoietin. For use in repair of blood vessels, it may be necessary to incorporate a factor such as VEGF. The sequences for these factors are as follows: SEQ ID NO: 1(NGF2); SEQ ID NO: 2 (BDNF); SEQ ID NO: 3 (VEGF); SEQ ID NO: 4 (PDGF); SEQ ID NO: 5 (GDNF); SEQ ID NO: 6 (NT-3); SEQ ID NO: 7 (FGF1, Acidic FGF); SEQ ID NO: 8 (FGF2); SEQ ID NO: 9 (basic FGF); SEQ ID NO: 10 (PEDF); SEQ ID NO: 11 (angiopoietin); SEQ ID NO: 12 (erythropoietin or EPO).

In this disclosure, we describe the fabrication of a biodegradable tube for the delivery of protein or DNA. Biodegradable guidance channels can serve as a vehicle for the sustained delivery of protein, DNA and DNA complexed with cationic lipids or cationic polymers. Additionally, the polymers may have one or more lumens. Guidance channels are currently being developed to create and maintain a space and limit the formation of scar tissue. The lumen provides an environment into which stimulatory factors can be controlled. The guidance channels are filled with a permissive substrate and may allow the accumulation of growth promoting factors. Additionally, these channels may be used as a cell transplantation vehicle to deliver stem cells, Schwann cells, or genetically engineered cells. Our approach extends the applications of the guidance channel by fabricating it as a controlled protein or DNA delivery vehicle. The proteins released from the tube can directly stimulate cellular processes. Alternatively, cells within the lumen can internalize the released DNA and subsequently act as bioreactors for the local production of neurotrophic factors. Sustained delivery of cationic lipid condensed DNA is expected to enhance gene delivery. In addition, the delivery may be spatially controlled, which may serve to create concentration gradients that can direct neurite extension.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Materials and Methods

The following Materials and Methods were utilized by the inventors of the present application for those examples presented below that relate to gene delivery from porous polymeric scaffolds, unless otherwise indicated.

Materials

Plasmid DNA was purified from bacteria culture using Qiagen (Santa Clara, Calif., USA) reagents and stored in Tris-EDTA (TE) buffer solution at −20° C. The plasmid pLuc has luciferase in the pNGVL (National Gene Vector Labs, University of Michigan) vector backbone with a CMV promoter. The plasmid pVEGF was provided by Dr. Dan Gazit and has VEGF-165 inserted into the pcDNA 3.1 vector backbone, which also has a CMV promoter. Poly(d,l-lactide-co-glycolide) (75:25 mole ratio of d,l-lactide to glycolide, i.v. 0.6-0.8 dl/g) was obtained from Alkermes, Inc. (Cincinnati, Ohio, USA), and Resomer 752 (75:25 mole ratio of d,l-lactide to glycolide, i.v. 0. 16-0.24 dl/g) was purchased from Boehringer Ingelheim (Petersburg, Va., USA). All other reagents were obtained from FisherBiotech (Fairlawn, N.J., USA) unless otherwise indicated.

Scaffold Fabrication.

Scaffolds were fabricated based on a previously described gas foaming/particular leaching process (Jang, J. H., and Shea, L. D. (2003), J. Controlled Release 86: 157-168; Nof, M., and Shea, L. D. (2002), J. Biomed. Mater. Res. 59: 349-356), with modifications to include wet granulation to improve solid mixing. Equal masses of PLG (i.v.=0.6-0.8, 0.16-0.24 dl/g) were dissolved in methylene chloride for subsequent microsphere manufacturing. A primary emulsion technique (w/o) was employed to create microspheres with a mean diameter of 12.5 µm (Jang, J. H., and Shea, L. D. (2003). Controllable delivery of non-viral DNA from porous scaffolds. J. Controlled Release 86: 157-168). Plasmid (500 or 800 µg at 1.0 or 1.6 µg/Al, respectively) was lyophilized with PLG microspheres (7 mg) in the presence of lactose (5.5 mM, 5.6 Al), with NaCl (135 mg, diam. 250-400 µm) added to the resulting solid. In the standard method, the solid components are mixed and loaded into the mold. For the wet granulation process, water (2 µl) was added to the solids and mixed for 1-2 min, which was sufficient to obtain a consistent mixture with no agglomeration. The solid mixture was loaded into the mold and compression molded at 1500 psi using a Carver press and the resulting construct was then equilibrated with $CO_2$ (800 psi) for 16 h in a custom-made pressure vessel. A rapid reduction in pressure results in fusion of adjacent microspheres. The construct was then immersed in water (2 ml) for 4 h to leach the porogen to produce the porous structure. The polymer constructs were dried and stored in a vacuum desiccator until use.

Characterization of DNA Incorporation and Release

DNA incorporation into the scaffold was characterized by quantifying the mass of DNA in the scaffold after the leaching process. To determine the amount of DNA in the scaffold, the leached scaffold was dissolved in chloroform (600 µl) and plasmid was extracted from the organic solution by the addition of TE (400 µl) and centrifugation at 5000 rpm for 10 min. The buffer addition and centrifugation step was repeated three times to maximize DNA recovery. DNA was quantified using a fluorometer (TBS 380, Turner Biosystems, CA, USA) and the fluorescent dye Hoechst 33258 (Molecular Probes, Eugene, Oreg., USA). The incorporation efficiency was defined as the ratio of the DNA mass present in the scaffold after the leaching step divided by the mass of DNA initially input. In vitro release assays were conducted to determine the release kinetics of DNA from the PLG scaffolds. Scaffolds were immersed in 500 µl of PBS (pH 7.4), and the solution was replaced with fresh PBS at the specified times. The concentration of DNA released from the scaffold was quantified using the fluorometer. DNA integrity was analyzed by agarose (0.8%) gel electrophoresis with ethidium bromide. A digital image of the gel was captured using a Kodak gel documentation system and the fraction of DNA in supercoiled conformation was determined using NIH Image software.

In vivo Transgene Expression

Scaffolds (cylindrical, 5 mm diameter×3.3 mm height) loaded with plasmid were implanted subcutaneously into male CD1 mice (20-22 g). Conditions examined include scaffolds fabricated with (i) pLuc, (ii) an empty vector with the luciferase cDNA removed, and (iii) no DNA ($n \geq 6$ for all conditions). In vivo luciferase expression was monitored using an IVIS imaging system (Xenogen Corp., Alameda, Calif., USA), which includes a cooled CCD camera. For imaging, the animals were injected ip with d-luciferin (Molecular Therapeutics, Inc., MI, USA; 150 mg/kg body wt, 20 mg/ml in PBS) using 28-gauge insulin syringes. The animals increased in weight during the experiment, and the volume of d-luciferin injected increased proportional to the weight of the animal. The animals were placed in a light-tight chamber and bioluminescence images were acquired (every 5 min for a total of 20 min) until the peak light emission was confirmed. Gray-scale and bioluminescence images were superimposed using the Living Image software (Xenogen Corp.). A constant size region of interest (ROI) was drawn over the implantation site. The signal intensity was reported as an integrated light flux (photons/s), which was determined by IGOR software (WaveMetrics, OR, USA). Background photon fluxes were obtained using the same procedures prior to the injection of d-luciferin. For these and other results, statistical comparisons between conditions were performed using the software package JMP (SAS Institute, Inc., Cary, N.C., USA).

Immunolocalization of Luciferase Expression.

The location of luciferase expression was visualized by performing immunohistochemistry with luciferase antibodies on frozen tissue sections. Scaffolds with luciferase-induced light emission above background were retrieved 3, 17, and 126 days postimplantation, fixed in 4% paraformaldehyde overnight at 48 C, and subsequently immersed in 10 and 30% sucrose solutions. Tissue blocks were embedded in OCT and frozen. Sections were cut (9 µm) and mounted on poly-l-lysine-coated slides. After blocking, sections were incubated with primary rabbit anti-luciferase antibody (Cortex Biochem, CA, USA) diluted (1:100) in PBS/0.1% BSA for 1 h at 37° C. A biotinylated goat anti-rabbit secondary antibody (Vector Laboratories, Burlingame, Calif., USA) was added, followed by incubation with the ABC reagent (Vector Laboratories). After rinsing, the slide was incubated in 3-amino-9-ethylcarbazole (Sigma, St. Louis, Mo., USA) peroxidase substrate, which produced a red product for visualization. For PCNA staining, tissue sections were incubated with primary rabbit anti-PCNA polyclonal antibody (Abcam, Mass., USA; 1:50 dilution) and subsequently with biotinylated goat anti-rabbit secondary antibody (Vector Laboratories; 1:200 dilution). Diaminobenzidine (DAB) substrate kit (Vector Laboratories) was used for staining proliferating cells, and tissue sections were counterstained with hematoxylin.

Angiogenesis

Scaffolds loaded with pVEGF were implanted subcutaneously into male CD1 mice as described earlier. Scaffolds containing pLuc were used as controls. Samples were retrieved 3 weeks post-implantation and embedded in OCT for subsequent cryosectioning as described earlier. In sections, blood vessels were identified by performing immunohistochemistry using purified rat anti-mouse CD31 (PE-CAM-1) monoclonal antibody (1:20 dilution; BD Biosciences, CA, USA) and an affinity-purified biotinylated anti-rat IgG (10 Ag/ml; Vector Laboratories). The color of positively stained blood vessels was developed with the DAB substrate kit (Vector Laboratories), and the sections were counterstained with hematoxylin. To quantify the density of blood vessels, sections were taken from three different regions of the scaffold for each condition (n=3). For each section, 15 images of the tissue were captured and the number of blood vessels was manually counted and normalized to tissue area, which was measured using NIH Image software. To measure blood vessel area, 420 blood vessels were selected for each condition and the area of the blood vessels was quantified using the NIH Image software.

Materials and Methods

The following Materials and Methods were utilized by the inventors of the present application for those examples presented below that relate to neurotrophin releasing single and multiple lumen nerve scaffolds or conduits, unless otherwise indicated.

Materials

Poly(d,l-lactide-co-glycolide) (PLG) with 75:25 mole ratio of lactide to glycolide was obtained from Boehringer Ingelheim Chemical (Resomer 755, i.v.=0.6-0.8, 80-120 kDa; Resomer 752, i.v.=0.16-0.24, 11-24 kDa, Petersburg, Va.). Resomer 755 and Resomer 752 are referred to as high molecular weight (HMW) and low molecular weight (LMW), respectively. Poly(vinyl alcohol) (PVA, 88% hydrolyzed, average MW 22,000) was purchased from Acros Organics (Morris Plains, N.J.). Recombinant rat nerve growth factor (NGF) was obtained from R&D Systems, Inc. (Minneapolis, Minn.). All other reagents were obtained from Fisher Scientific (Fairlawn, N.J.) unless otherwise indicated.

NGF Loaded Microsphere Fabrication

NGF-encapsulated microspheres were fabricated using an established cryogenic double emulsion technique (S. Ando, et al., PLGA microspheres containing plasmid DNA: preservation of supercoiled DNA via cryopreparation and carbohydrate stabilization, J. Pharm. Sci. 88 (1) (1999) 126-130). Briefly, a protein solution containing 50 mg/mL sucrose, BSA (2000: 1; BSA to NGF ratio), MgCO3 (3% wt of BSA), and NGF was added to a 3% solution of PLG in dichloromethane. This mixture was emulsified by sonication, and the inner aqueous phase was selectively frozen by immersion in liquid nitrogen. A PVA solution (5%, 50 mL with 50 mg/mL sucrose) was added to the mixture, and a second emulsion was formed by homogenization at 5000 rpm for 15 s. The resulting solution was diluted in PVA (1%, 30 mL with 50 mg/mL sucrose) and stirred at room temperature for 3 h. Microspheres were collected by centrifugation, washed three times with deionized water, and lyophilized overnight.

Conduit Fabrication with Single Lumen and Multiple Lumens

PLG conduits having either a single lumen or multiple lumens were fabricated by a gas foaming/particulate leaching process (see U.S. Pat. Nos. 6,281,256 and 6,797,738, incorporated by reference in their entireties). For single lumen conduits, NGF loaded microspheres were mixed with a porogen (NaCl, 250 µm<particle diameter (dp)<420 µM) to a total mass of 30 mg. A wet granulation process was employed to facilitate homogeneous mixing of the polymer and porogen (J. T. Carstensen, Pharmaceutical Principles of Solid Dosage Forms, CRC Press, 1993). Small quantities of deionized water (<3.0 µL) were added to the porogen/polymer granulation and mixed manually. The polymer and porogen were loaded into a custom made stainless steel cylindrical mold for the fabrication of single lumen conduits. For conduits with multiple lumens, the solids were loaded into an aluminum custom-made mold that contained stainless steel pins (diameter=150 or 250 µm) to create parallel lumens within the conduit. Multiple lumen scaffolds were formed with salt crystals with dp between 106 µm and 250 µm. After loading, the molds were transferred to a pressure vessel to equilibrate with $CO_2$ gas (800 psi) for 12 to 16 h. After quenching the pressure, conduits were removed from the molds, immersed in deionized water for 4 h to leach the porogen, and then dried overnight. A leaching time of 4 h was determined by comparing the scaffold mass after immersion for 4, 6, and 24 h. Longer leaching times had negligible effect on the mass of the scaffold. Therefore, 4 h of leaching time was chosen to ensure that protein losses during leaching were minimized.

Conduit Porosity and Architecture.

The porosity of the conduits was determined based on the physical properties and the pore structure was visualized using scanning electron microscope. The porosity (P) is calculated according to Eq. (1), where Vp and Vc are the volumes of polymer and conduit, respectively.

$$P=(1-V_p/V_c)\times 100 \quad \text{Eq. 1}$$

The volume of the polymer (Vp) is calculated using Eq. (2) from mass of the conduit (Mconduit) and density of the polymer (Dpolymer).

$$Vp=M_{conduit}/D_{polymer} \quad \text{Eq. 2}$$

The volumes of the conduits, both single lumen (Vc,single) and multiple lumen (Vc,multiple), are calculated from the physical dimensions of the conduit according to Eqs. (3) and (4). For the single lumen conduits, the lumen volume is not incorporated into the porosity calculations, but based on measurements of the inner and outer diameters (Douter, Dinner), and length (L) of the conduit. For conduits with multiple lumens, the porosity due to the channels is included in the overall porosity measurements and calculated according to Eq. (1), where the conduit volume is defined with the height (H), width (W), and length (L) of the conduit.

$$Vc,\text{single}=\pi\times(D^2\text{outer}-D^2\text{inner})/4 X L \quad \text{Eq. 3}$$

$$Vc,\text{multiple}=H\times W\times L \quad \text{Eq. 4}$$

The volume attributed to the channels (Vmultiple, channel) was separately calculated using Eq. (5) with the channels area (kr2 channel), length of conduit (L), and the number of channels (nchannels).

$$V\text{multiple,channel}=\pi r^2_{channels}\times L\times n_{channels} \quad \text{Eq. 5}$$

Visualization of the conduit microstructure was achieved using scanning electron microscopy (Hitachi 3500N, Japan).

The conduits were sputter coated (Cranberry Twp., Cressington, Pa.) with a gold film (3 nm), and examined using an electron voltage of 20 kV.

Mechanical Testing Analysis

The mechanical properties of the porous PLG conduits were measured by using a custom-built probe test fitted with a rigid flat punch. The probe displacement and the force that was exerted normal to the axis of the channel(s) were recorded using a Labview program. For single lumen tubes, the load was normalized by the conduit length and the displacement was normalized by the outer diameter. Conduits were compressed until collapse of the lumen. A line was fit through the experimental data at the inflection point of the force-displacement curve. The transverse compressive strength (Sc) was defined as the force at which the force-displacement curve deviates from the fitted line by 1% (FIG. 24A). For the conduit with multiple lumens, the applied stress is calculated by dividing the load by the cross-sectional area of the conduit. The applied strain is obtained by dividing the displacement by the un-deformed thickness of the conduit. These conduits were compressed until a maximum stress of approximately 10 kPa. Elastic moduli (E) were determined from slopes of the stress/strain curve obtained during both compression and decompression of the conduit (FIG. 25A).

Release Kinetics of NGF from PLG Conduits

The release kinetics from conduits with a single lumen were determined using radiolabeled NGF, the results of which can be found in FIGS. 17 and 18. Conduits were fabricated with $I^{125}$-labeled NGF (Amersham Biosciences, Piscataway, N.J.) that was either mixed with or encapsulated within the microspheres. Upon fabrication and leaching, conduits were incubated in phosphate buffered saline (PBS, 2 ml, pH=7.4) at 37° C. At specific time points, the conduit was removed and immersed in fresh PBS. The activity of the released medium was determined using a Gamma counter (Micromedic 4/600 Plus, Micromedic, Horsham, Pa.). The cumulative release of NGF from PLG conduits was calculated by dividing the cumulative activity released into the liquid by the initial activity present in the conduit.

Bioactivity Assay of Released NGF

The bioactivity of NGF released from PLG conduits was assayed by neurite extensions from dorsal root ganglia (DRG) cultures. Embryonic (E8) chick DRG (fertile white leghorn chicken eggs, Lansing Mich.) was dissected according to established procedures (G. Banker, K. Goslin, Culturing Nerve Cells, 2nd ed., MIT Press, Cambridge, Mass., United States, 1998), and cultured at 37 8 C and 5% CO2 in DMEM (Invitrogen, Gaithersburg, Md.) supplemented with 13 mg/mL BSA, 0.067 mg/mL insulin, 0.067 µg/mL selenium, 6.7 µg/mL avian transferrin. Conduits containing NGF were incubated (37° C., 5% CO2) in basal culture media for subsequent bioactivity testing. At specific time points, this release media was collected and added to culture media at a final NGF concentration of 14 ng/mL, with the appropriate dilution calculated from release studies. DRG were cultured within 0.5 mg/mL collagen gel (rat tail collagen, type I, BD Biosciences, Bedford, Mass.). Neurite extension by DRG was observed under phase contrast microscopy. The neurite length was characterized by averaging the length of 20 randomly selected neurites from each DRG after 24 h of culture. Control experiments include DRG cultured with media containing 14 ng/mL NGF and release media collected from PLG conduits without NGF. All experiments were performed in triplicate with replication.

In vivo Studies

The channel integrity was examined in vivo by subcutaneous implantation of the conduits into male CD-1 mice (Charles River Laboratories, Wilmington, Mass.). The conduits were retrieved after 13 days of implantation, and fixed with 4% paraformaldehyde overnight at 4° C. The samples were then immersed in 10% and 30% sucrose for 4 h and overnight, respectively. Samples were embedded in OCT, rapidly frozen, sectioned, and stained with hematoxylin and eosin for examination by light microscopy. Animals were treated in accordance with the NIH Guide for the Care and Use of Laboratory Animals and the IACUC protocol at Northwestern University.

Statistical Analysis

Statistical analyses were performed using the statistical package JMP (SAS, Cary, N.C.). For multiple comparisons, pairs were compared using the Student's t-test with p values indicated in the figure legend.

Example 1

Fabrication of Cylindrical Scaffolds by the Gas Foaming Procedure

A gas foaming process has been employed to fabricate cylindrical scaffolds, with either a single (FIG. 1a) or multiple (FIG. 1b) lumens, by assembly and fusion of assembled microspheres. The copolymer of lactide and glycolide (PLG) are used for fabrication, which as been widely used in tissue engineering and neural regeneration, and is well known to the skilled artisan. Microspheres are loaded into a custom built mold (O.D.=3 mm) and fused using a gas foaming process as described in U.S. Pat. No. 6,281,256. Molds are equilibrated in high pressure $CO_2$ (800 psi), and pressure quenching leads to the nucleation and growth of gas pores in the polymer, resulting in fusion of adjacent microspheres. PLG copolymers (50:50, 75:25, and 85:15) with a range of molecular weights (i.v.=0.2 to 1.4 dL/g) can be processed, allowing scaffolds to be fabricated that degrade over times ranging from weeks to months.

Figure 1:
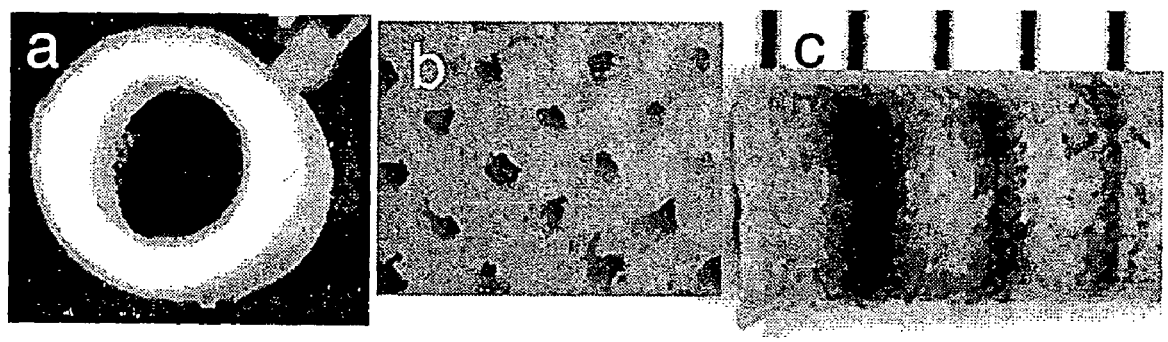
FIG. 1: Cylindrical scaffold fabricated with a single lumen (a) or multiple lumens (b). For c), scaffolds were fabricated in layers using a combination of empty and trypan blue loaded microspheres.

For application in nerve regeneration, scaffolds exteriors limit cell infiltration through the curved exterior to maintain an open path, but are porous to allow nutrient transport. The exterior surface can be coated with a 2% alginate solution that is then immersed in 100 mM $CaCl_2$, which crosslinks the alginate and creates a thin coating (FIG. 1a). Alginate limits protein adsorption and does not support cell adhesion without covalent modification, which limits cellular infiltration in vivo. Additionally, alginate gels have average pore diameters in the range of 5 to 200 nm, and offer little transport resistance to diffusion of small molecules (<40 kDa), such as nutrients. Polymer scaffolds fabricated with a porogen:polymer ratio greater than 2:1 have sufficient porosity to allow nutrient transport that supports cell survival through 8 days of culture in vitro (not shown).

Spatially controlled drug incorporation: The spatial location of bioactive factor along the length of the scaffold can be controlled by assembling the microspheres in layers. Each layer can contain a controlled quantity of drug. To demonstrate spatially patterned incorporation, empty microspheres (white) and trypan blue loaded microspheres (blue) were layered into the mold and subsequently processed by gas foaming (FIG. 1c). The minimum width of the stripes is approximately 0.2 mm.

Example 2

Drug Incorporation and Release from Cylindrical Scaffolds

Figure 2:
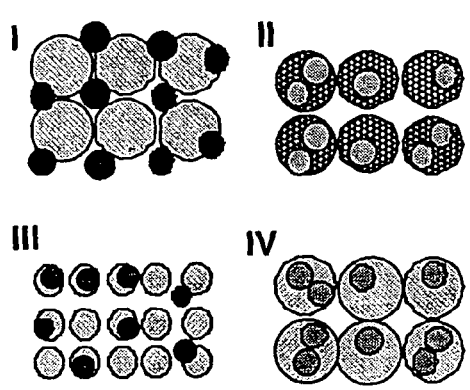
FIG. 2: Schematics of drug incorporation. DNA is I) lyophilized with microspheres, or II-IV) encapsulated within microspheres (II: low MW polymer, III: small microspheres, IV: high MW polymer). Release kinetics depend upon the method of incorporation (I vs. IV), polymer molecular weight (II vs. IV), and microsphere size (III vs. IV).
Figure 2:
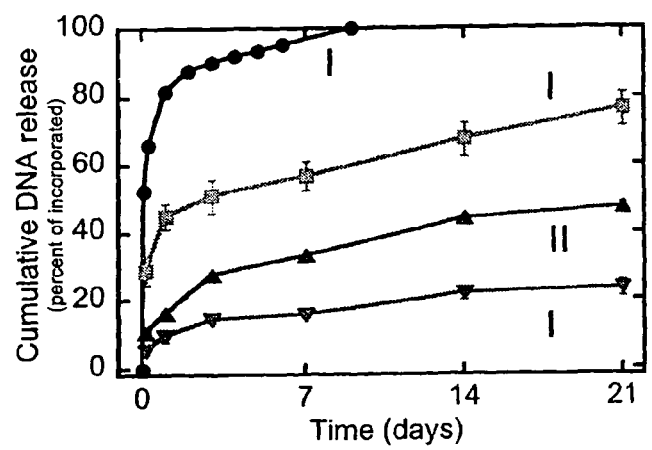

The gas foaming procedure allows for the incorporation of bioactive factors into polymers by two methods shown schematically in FIG. 2. In the first method (FIG. 2-I), lyophilized drug is mixed with polymer microspheres, compression molded, and foamed into a structure. Proteins and DNA can be lyophilized in the presence of stabilizers (e.g., sucrose, lactose 0.1 M), which retain their integrity and activity during the freezing and dehydration processes. Alternatively, the factors can be incorporated directly into the polymer microspheres using a double emulsion process, and then formed into the cylindrical structure (FIG. 2, II-IV).

The two techniques for incorporation can be used to differentially regulate the release kinetics of drug from the polymer scaffold (FIG. 2). Scaffolds with incorporated DNA were fabricated as shown in FIG. 2, immersed in PBS, and the concentration of DNA released into the surrounding fluid was measured with the Hoechst dyebinding assay. A sustained release of plasmid DNA was observed, with times for total release of plasmid ranging from 4 days to more than 21 days (FIG. 2). Mixing lyophilized DNA with blank microspheres led to a rapid release (FIG. 2I), likely due to surface association of the DNA with the polymer. Conversely, encapsulation of DNA into microspheres showed a sustained release for at least 21 days. Release kinetics from the polymer can also be manipulated through the molecular weight (MW) of the polymer and the microsphere diameter used during fabrication.

Example 3

Transfection with Release DNA Complexes Encoding for Reporter Genes

Figure 3:
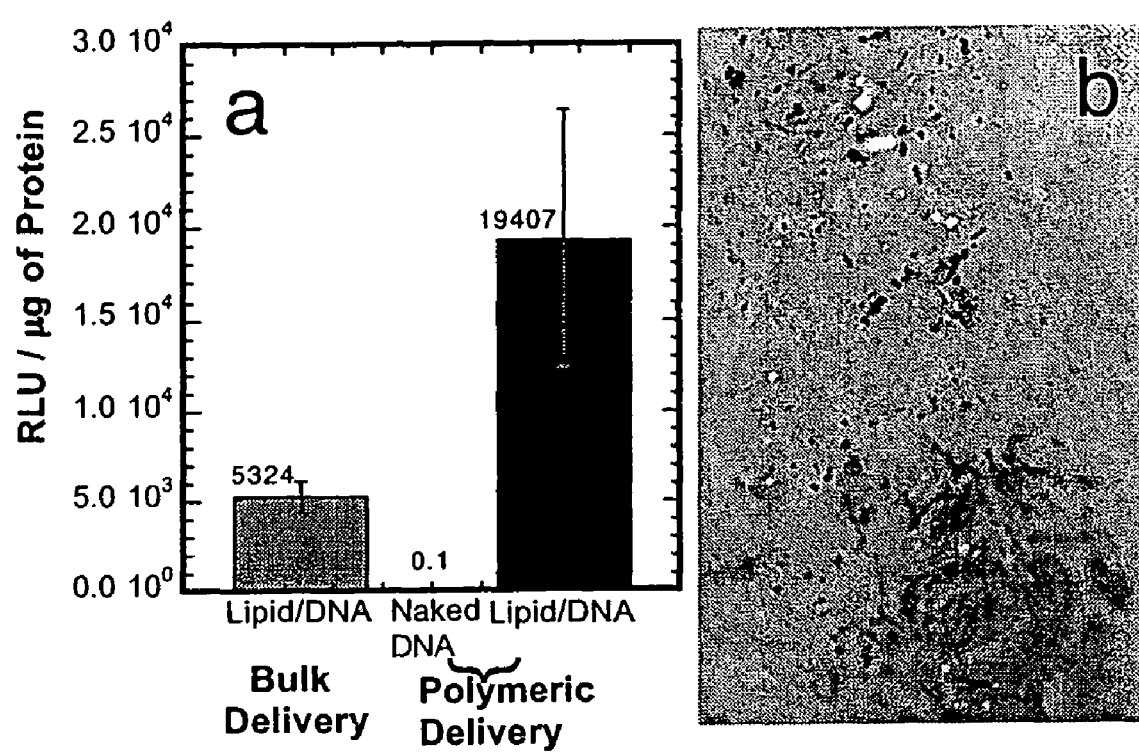
FIG. 3: (a)Transfection of NIH/3T3 fibroblasts with the luciferase-encoding plasmid by incubation with PLG scaffolds. (b) Photomicrograph of X-gal stained collagen sponges. Sponges were cultured in scaffolds in which the DNA complexes were loaded throughout the scaffold.

The ability of DNA complexes released from the polymer scaffolds to transfect cells in vitro was subsequently examined. The reporter genes luciferase and b-galactosidase were used to characterize transfection through measurements of the quantity of protein production (luciferase assay) and the number of cells transfected (light microscopy). The release of naked DNA from the polymer scaffolds resulted in low quantities of protein production (FIG. 3a). The release of lipid/DNA complexes, termed lipoplexes, resulted in expression by NIH/3T3 cells at levels similar to bolus delivery of freshly prepared lipoplexes. Polymeric tubes releasing DNA lipoplexes (10 μg) transfected cells cultured within the lumen. NIH/3T3 cells were seeded onto collagen matrices using a dynamic seeding procedure and cultured within the lumen. X-gal staining of the collagen showed transfected cells throughout the collagen (FIG. 3b).

Example 4

Figure 4:
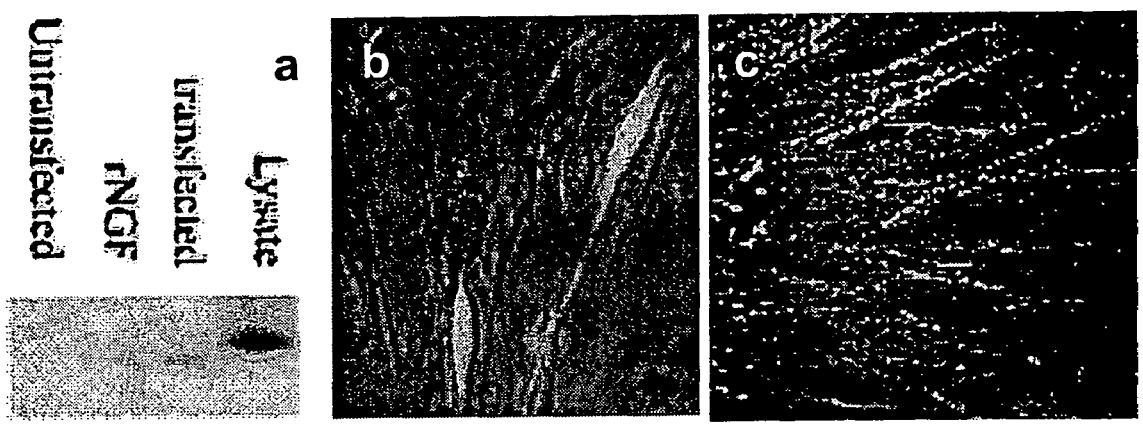
FIG. 4: (a) Western blot for PC12 cells transfected with a NGF-encoding plasmid. Lanes 3 and 4 are representative of triplicate samples collected from the media and cell lysates respectively. (b) Transfected Schwann cells, which are able to stimulate DRG neurite extension in vitro. Schwann cells (>98% purity) were isolated from rat sciatic nerve (c) Confocal image of neurite extension by DRG within a collagen gel. DRG were isolated from E8 chick embryos and placed in culture within an NGF-releasing tube.

In vitro Transfection with Nerve Growth Factor to Induce Neuronal Differentiation Released lipoplexes encoding for NGF have also been used with primary cultures of Schwann cells and DRG. Transfection of PC12 cells with the pRK5-NGF plasmid, provided by Dr. Nomoto, resulted in NGF production as evidenced by Western blotting (FIG. 4a) and neurite extension (not shown). The NGF cDNA has been inserted into pCMS-EGFP (Clontech), which is a dual expression vector, and have confirmed that the plasmid produces functional NGF (not shown). This NGF/EGFP vector (pCE-NGF) will allow EGFP and NGF production, with each under the control of different promoters. The GFP will remain localized to the transfected cells whereas the NGF will be secreted, which allows the location of transfected cells to be visualized with respect to neurite extension. Released lipoplexes were able to transfect Schwann cells (FIG. 4b) and the protein produced by cells was able to initiate neurite extension by DRG. Neurite extension through collagen can be visualized by confocal microscopy (FIG. 4c).

Example 5

In vivo Transfection and Non-Invasive Monitoring of Gene Expression

The quantity and duration of gene expression in vivo by DNA delivery from the scaffolds were examined using a non-invasive imaging system. Polymer scaffolds containing naked DNA encoding for luciferase were implanted into a subcutaneous pocket of CD1 mice. Luciferase bioluminescence was detected using a sensitive CCCD system (Xenogen) that allows non-invasive monitoring of luciferase expression (FIG. 5a). Luciferase activity was seen around the scaffolds releasing the luciferase plasmid, but not in the control scaffold that had no DNA. The quantity of expression was analyzed using software to measure the photons emitted and subtracting the reading from a similar sized background (FIG. 5b). For porous scaffolds, expression was sustained for 105 days (n=5).

Example 6

Substrate-Mediated Gene Delivery from Tissue Engineering Scaffolds: Surface Immobilized PEI/DNA Complexes Materials and Methods Fabrication of Polymer Scaffolds PLG (75:25 mole ratio of D, L-lactide to glycolide, i.v.=0.6-0.8 dl g-1) (Alkermes Inc., OH) disks and porous scaffolds were fabricated using the previously described gas foaming process. Microspheres were made with a primary emulsion technique (w/o) and used as building blocks for disk and scaffold fabrication. For disk fabrication, microspheres (10 mg) were loaded into a cylindrical stainless steel die (inner diameter 5 mm) and compression molded (10 seconds at 1500 psi) using a Carver laboratory press (Carver, Muncie, Ind.). For porous scaffold fabrication, microspheres (7 mg) were mixed with a porogen (NaCl, 220 mg), loaded into a cylindrical die, and compression molded. The molded disks and scaffolds were then equilibrated with $CO_2$ (800 psi) for 16 hours in a custom-made pressure vessel. Reducing the pressure results in microsphere fusion to make intact polymer constructs. The scaffolds were immersed in water for 4 hours to leach the salt. Polymer constructs were stored in a vacuum dessicator until use.

DNA Complex Immobilization

DNA complexes were formed by mixing plasmid with branched PEI (25 kDa) (Aldrich Chemical Company, Milwaukee, Wis.). The initial amount of PEI mixed with plasmid was varied to control the ratio of nitrogen/phosphate (N/P=6, 9, 18). PEI was dissolved in sodium bicarbonate (1 mM, pH 8.0) and diluted (100 μL final volume) with 150 mM sodium chloride solution, which was added to 100 μL of the plasmid DNA.

Polymer disks and scaffolds were coated with 10% fetal bovine serum (FBS) in PBS by incubating polymers with FBS at 37° C. for 24 hours prior to complex adsorption. Polymer disks were attached to tissue culture plates (96-well) using autoclaved silicon grease. For twodimensional non-porous disks (diameter=5 mm), DNA complexes (200 μL) were incubated (1, 4, 24 hours) and washed with PBS (×2). The surface-bound complexes were visualized by adsorbing complexes containing fluorescently-tagged DNA (Rhodamine labeling kit, Mirus Bio Corp., WI). HEK293T (20,000 cells well$^{-1}$) or NIH3T3 (10,000 cells wells$^{-1}$) in culture media (DMEM with 10% (v v$^{-1}$) FBS, 1% (v v$^{-1}$) penicillin streptomycin, and 1% (v v$^{-1}$) sodium pyruvate) were seeded and cultured on the PLG at 5% CO2, 37° C., and 95% humidity for 48 hours.

For three-dimensional porous scaffolds (diameter=5 mm, height=6.5 mm), serum-coated coated and PBS-washed scaffolds were dried on gauze pads prior to incubation with DNA complexes. PEI/DNA complexes (1 mL of 50 μg in 150 mM NaCl) were lyophilized in the presence of 20 mM sucrose. Complexes were rehydrated in 100 μL of sterile deionized water and added to the porous scaffold, which were then incubated for 1 hour. After washing with PBS (×2), HEK293T cell suspension (60 μL of 5×105 cells mL$^{-1}$) was subsequently added to the porous scaffold, incubated for 4 hours (5% CO$_2$, 37° C.), and then immersed in media (2 mL) for 48 hr culture.

Quantification of Surface-Bound Complexes

The quantity of DNA immobilized to the polymer was determined using radiolabeled DNA. Plasmid DNA was radiolabeled with a α-32P dATP using a nick translation kit (Amersham Pharmacia Biotech, Piscataway, N.J.) according to the manufacturer's protocol with minor modifications as described in Segura et al. (Segura, T., Chung, P. H. & Shea, L. D. *Biomaterials* 26, 1575-1584 (2005)). PEI/DNA complexes were formed using 32P DNA and adsorbed onto the PLG disks. At the specified times (1, 4, 24 hours), the supernatant was removed and the disks were washed twice with PBS. Subsequently, the disks were placed in scintillation cocktail (5 mL; ScintiVerse II) and the radioactivity was measured with a scintillation counter. The amount of DNA was calculated using a calibration curve.

Transfection Analysis

The extent of transgene expression and the number of transfected cells were determined using the reporter genes luciferase (transgene expression) and β-galactosidase (number transfected). After 48 hour culture, luciferase levels were measured on a luminometer using the luciferase assay system (Promega, Wis.), with levels normalized to the initial cell seeding. Alternatively, the expression of β-galactosidase was visualized by staining with X-gal solution, and the number of transfected cells was determined by counting 5 random fields on the surface (non-porous disks). To determine the total cell number, cells were trypsinized and counted using a hemocytometer. The efficiency of cell removal from the polymer was examined by incubation with Hoechst 33258 to label the nuclei of any remaining cells, which could be manually counted. The number of remaining cells was less than 0.5% of the total cell number. The fraction of transfected cells was determined as the number of transfected cells divided by the total cell number. All experimental conditions were performed in triplicate.

In vivo Expression

Scaffolds containing adsorbed PEI/DNA complexes (initial loading: 50 μg) were implanted subcutaneously into male CD1 mice (20 to 22 g). For these in vivo studies, scaffolds were hydrolyzed by immersing in 1N NaOH for 3 minutes. The increased presence of carboxylic acids following surface hydrolysis was confirmed by Fourier Transform Infrared Spectroscopy (FTIR, Thermo Nicolet, Nexus 870 with the Tabletop optics module (TOM)). After hydrolysis, scaffolds were vigorously rinsed with deionized water and PEI/DNA complexes were deposited on the scaffolds as described earlier. Note that an in vivo formulation of PEI was employed for these studies (Qbiogene, Irvine, Calif.).

In vivo luciferase expression was monitored using an IVIS imaging system (Xenogen Corp., Alameda, Calif.), which includes a cooled CCD camera. To increase the cross-sectional area for bioluminescence detection, the scaffold dimensions were adjusted to a height of 1.5 mm and a diameter of 1.3 cm, by compression molding with a stainless steel mold with a 1.3 cm diameter. For imaging, the animals were injected i.p. with D-luciferin (Molecular Therapeutics Inc., MI, 150 mg kg$^{-1}$ body weight). The animals were placed in a light-tight chamber and bioluminescence images were acquired (every 5 minutes for a total of 20 minutes) until the peak light emission was confirmed. Gray scale and bioluminescence images were superimposed using the Living Image software (Xenogen Corp., CA). A constant size region of interest (ROI) was drawn over the implantation site. The signal intensity was reported as an integrated light flux (photons sec$^{-1}$), which was determined by IGOR software (WaveMetrics, OR). Background photon fluxes were obtained using the same procedures prior to the injection of D-luciferin. Background levels have been shown to not be statistically different from scaffolds containing no DNA. For these and other results, statistical comparison between conditions was performed using the software package JMP (SAS Institute Inc., NC).

Results

DNA Immobilization

The incubation of macromolecules with biomaterials results in surface adsorption of these macromolecules, a property observed for many synthetic polymers. Many biomaterials that are employed as a support for cell growth, or as a delivery vehicle for cell transplantation, are coated with proteins to facilitate cell adhesion. After fabrication, PLG scaffolds are hydrophobic, resulting in large contact angles. Surface hydrophobicity promotes protein adsorption through an entropic driving force. Incubation of PLG scaffolds with serum resulted in protein adsorption to the polymer, with fibers homogeneously distributed across the surface, which dramatically differed from the unmodified surface (data not shown). This serum coating creates a hydrophilic substrate and functions to promote cell adhesion. DNA complexes were formed by mixing plasmid with polyethylenimine (PEI), which is a cationic polymer that is a widely used transfection reagent, and subsequently adsorbed to PLG either before or after serum coating. Serum coated PLG maintained complex sizes regardless of deposition time, whereas the absence of serum resulted in the gradual aggregation of complexes on the scaffold with increasing deposition time. Preliminary evaluation of gene transfer in vitro by immobilizing DNA to serum coated and uncoated scaffolds indicated that transfection was significantly higher on serum-coated scaffolds. We subsequently focused on DNA complex immobilization, release, and in vitro transfection from serum coated scaffolds.

The quantity of immobilized complexes on serum-coated polymer increased with the time of deposition. DNA was complexed with PEI at three N/P ratios (6, 9, 18) prior to adsorption, with N/P defined as the ratio of amines in PEI to phosphates in DNA. The quantity adsorbed was not substantially affected by the N/P ratio of the complexes (P>0.05). PEI/DNA complexes with N/P ranging from 5 to 25 had zeta potential measurements ranging from −13 mV to 20 mV. Thus, the independence of adsorption on N/P ratio suggests that immobilization is not mediated exclusively through electrostatic interactions. Increasing the deposition time from 1 hour to 24 hours increased the amount immobilized from approximately 2.2% to 27.1% of the incubated DNA (i.e., 2 μg) (FIG. 19a). For 2 μg of DNA incubated with the polymer, the mean quantity of immobilized PEI/DNA complexes for deposition times of 1, 4, and 24 hours was 45, 317, and 544 ng, respectively. Increasing the amount of complexes incubated with the scaffold to 5 μg increased the total amount immobilized, with the percent immobilized unchanged (data not shown). The percentage of DNA immobilized to the PLG scaffold were substantially less than that previously observed on polystyrene surfaces (nearly 80% after 24 hours). These differences in immobilization likely reflect differences in the surface chemistry of the polystyrene and the polymer, and the extent to which serum adsorbs to each.

The stability of DNA complexes on the polymer was subsequently examined through release studies. An increasing N/P ratio resulted in less dissociation of complexes from the polymer (FIG. 19b). Complexes immobilized to the scaffold had initial bursts ranging from 17.8% to 55.5% at 4 hours for N/P ratios in the range of 6 to 18. After the initial burst, a steady release from the scaffold was seen during the subsequent 4 days at a rate of 7.3% per day for all conditions. The total amount release ranged from 41.8% to 90.2%.

Non-specific adsorption of macromolecules to surfaces results from a combination of molecular level interactions, including electrostatic, hydrophobic, and van der Waals interactions. The adsorption of proteins to hydrophilic substrates has generally been described as supporting reversible binding, whereas protein adsorption to hydrophobic substrates generally results in more permanent adsorption due to conformation changes that can occur at the surface. The cationic polymer PEI has been used as a coating for polystyrene substrates. Nevertheless, PEI/DNA complexes, which contain plasmid self-assembled with PEI, may have substantially different adsorption properties than proteins. Although DNA complex adsorption was independent of the N/P ratio, complex release from the surface did depend upon the N/P ratio, with greater release for complexes formed at a lower N/P ratio. This dependence of release on N/P was unexpected given the independence of adsorption on N/P, and suggests that the mechanism of desorption differs from adsorption. Desorption may reflect a partial dissociation of the complex, such as release of DNA from a fraction of the PEI that remains on the surface.

In vitro Transfection

Cell attachment directly to the substrate, on which the complexes are adsorbed, may overcome limitations with gene delivery that are associated with mass transport or complex aggregation. Substrate-mediated delivery substantially increased the number of transfected cells relative to bolus delivery, while requiring significantly less DNA. Large numbers of transfected cells were seen homogeneously across the PLG. The percentage of transfected cells by surface-bound complexes (N/P=9) decreased from 67.1±17.5% to 30.7±6.7% as the deposition time increased from 1 hour to 24 hours (FIG. 19c). Maximal numbers of transfected cells were observed with the lowest quantity of surface-bound complexes (45 ng), which is an order of magnitude less DNA required to achieve the highest levels of transfection by bolus delivery. For bolus delivery, addition of 1 μg of DNA was able to achieve transfection of approximately 20% of the cell population. The increase in the number of transfected cells relative to bolus may result from the substrate effectively distributing the DNA complexes among the cell population. Complexes immobilized to the substrate are prevented from aggregating in solution, which may distribute them more effectively among the cell population.

Maximal transgene expression was dependent upon an appropriate balance between the N/P ratio and the amount of immobilized DNA, which is regulated by the deposition time (FIG. 29a, b). At the lowest N/P ratio, transgene expression increased with the deposition time. However, for N/P equal to 18, transgene expression decreased with an increase in deposition time. At the intermediate N/P ratio of 9, the relationship between transgene expression and deposition time was a function of cell type. For NIH/3T3 cells, transgene expression increased with an increasing deposition time, whereas HEK293T cells demonstrated a biphasic relationship between transgene expression and deposition time. At short incubation times, increasing the N/P ratio increased transgene expression. However, for the intermediate and long deposition times, transgene expression was maximal for N/P equal to 9. The N/P ratio of the complex, which affected the stability at the surface, also influenced transgene expression. Delivery by immobilization to the substrate enhanced transgene expression by 1-3 orders of magnitude relative to bolus delivery of similar DNA quantities (FIG. 29c, d). An important issue for the ultimate use of DNA immobilized scaffolds is the maintenance of activity during long-term storage. Scaffolds with immobilized DNA complexes maintained their transgene expression levels following lyophilization in the presence of sugars, such as sucrose or lactose (data not shown).

Similar to bolus delivery, the quantity of DNA complexes delivered from the substrate must be sufficient to promote transgene expression; however, excessive quantities of complexes may decrease cell proliferation or increase cytotoxicity. The quantity of surface-immobilized DNA was regulated through the amount incubated and the deposition time of complexes, and increasing doses led to a decrease in the percentage of transfected cells (FIG. 19c). To examine this phenomenon, the cell number on the polymer was examined. The seeding efficiency, which was defined as the ratio of cells remaining after 3-hr culture to cells initially seeded, was 55.8% and 51.7% for NIH/3T3 and HFK293T, respectively (FIG. 30a, b). For all conditions, the number of cells on the polymer increased relative to the initial number seeded during the 48-hour culture; however, longer deposition times produced smaller increases in cell number. Increasing doses given as a bolus have been associated with decreasing metabolic activity and increasing cytotoxicity, consistent with the reduction in cell number that is observed for the scaffold at higher DNA loadings.

The N/P ratio is a critical property that significantly affects gene transfer from the surface, through affecting complex size, zeta potential, substrate binding and release, and intracellular trafficking. The cationic polymer PEI supports the adsorption of complexes to the substrate and lower N/P ratio of complexes resulted in faster initial burst (FIG. 19b). Higher N/P ratios have been proposed to enhance transfection by facilitating complex association with plasma membrane and promoting endosomal escape. However, complexation at high N/P ratios can result in the presence of free PEI, which can be toxic due to permeabilization of the plasma membrane. Free PEI should not be a significant issue for substrate-mediated delivery given the multiple washing steps that are performed. Immobilized complexes with higher N/P ratio decreased the number of cells on the substrate; yet transgene expression generally increased for deposition times of 1 or 4 hours. However, consistent with reports for bolus delivery, longer deposition times (i.e., increased quantities of DNA) and higher N/P ratios significantly decreased the number of transfected cells and transgene expression, potentially due to excessive quantities of PEI (FIG. 19c, 29).

Substrate-mediated delivery can be readily applied to highly porous three-dimensional tissue engineering scaffolds. The volume in which the complexes were prepared, the quantity of DNA, and the deposition time were manipulated to achieve a homogeneous distribution of DNA immobilized throughout the scaffold. Seeding of HEK293T cells resulted in transfected cells throughout the scaffold (FIG. 20b, c, d), which was not observed on control scaffolds without plasmid (FIG. 20a). Transgene expression on the porous scaffold was comparable to that observed for cells cultured on two-dimensional disks. Also consistent with the disk culture, transgene expression increased with an increase in N/P ratio (FIG. 20e). The ability to transfect cells throughout this scaffold suggests that this approach could be applied to any geometry to which complexes can be adsorbed. Additionally, the surface area of the scaffolds may be a key design parameter for regulating transgene expression, as the surface area regulates both complex adsorption, and cell adhesion.

In vivo Expression

Although DNA complexes are widely used for in vitro applications, the translation of these vectors to in vivo applications has been limited by low levels of gene transfer, which are similar to or less than that obtained with naked DNA. The physicochemical properties of polyplexes and lipoplexes can lead to interactions with serum proteins that can inactivate the complexes, through processes such as complex destabilization, aggregation, or clearance. Immobilization of DNA complexes to the biomaterial substrate may limit the inactivation of the complexes and promote transgene expression. Preliminary studies using serum-coated scaffolds showed no significant transgene expression in vivo, which we hypothesized to be related to the vector stability at the surface. Subsequently, scaffolds were hydrolyzed with NaOH prior to complex immobilization, which has been used previously to promote protein adsorption and enhance cell attachment to the scaffold. FTIR analysis confirmed the increased presence of carboxylic acid groups after hydrolysis of the PLG scaffolds. An increased presence of carboxylic acid groups at the surface would create a more negatively charged scaffold, potentially enhancing electrostatic interactions between the complex and surface. Surface hydrolysis significantly increased the retention of PEI/DNA complexes (N/P=9) at the surface after 3-day incubation in buffer, with 90.7±2.3% of the immobilized complexes on the hydrolyzed surface relative to less than 40% retained on the non-hydrolyzed surface (FIG. 19b).

Subcutaneous implantation of the PLG scaffolds with immobilized PEI/DNA complexes induced localized transgene expression over the scaffolds. Light emission from the scaffold was significantly above background during the first 2- days post-implantation, and declined to background levels at day 4. Light emission was not observed for scaffolds that had not been hydrolyzed (not shown), indicating that the surface chemistry must be appropriately tuned for the application (e.g., in vitro or in vivo). Interestingly, the light emission obtained by substrate-mediated delivery of 50 μg of PEI/DNA complexes was comparable to that obtained by sustained delivery of 250 μg of plasmid DNA, suggesting an increased gene transfer efficiency. The duration of transgene expression by immobilization was less than has been observed for sustained release systems, and thus may provide a complementary approach to promote the initial steps of tissue formation. However, alternative surface chemistries or immobilization strategies may be able to extend the duration of transgene expression. The ability to express tissue inductive factors from within a tissue engineering scaffold may provide a powerful tool to stimulate the in vivo development of functional tissue replacements.

Non-specific adsorption of DNA complexes to tissue engineering scaffolds can achieve localized gene transfer in vitro and in vivo, using less DNA relative to delivery as a bolus. Immobilization also homogeneously distributes the DNA throughout the scaffold, resulting in large numbers of transfected cells at these low quantities. Gene transfer is dependent upon the complex and substrate properties, which must balance binding and release with cellular internalization and trafficking. The substrate can be prefabricated in an appropriate geometry, for the subsequent immobilization of complexes. This approach may be widely applicable to numerous existing materials. Alternatively, novel materials may ultimately be designed that specifically adsorb DNA complexes. The nano-scale control of chemical and physical properties of biomaterial substrates, combined with the development of strategies to regulate vector immobilization and release will enable numerous applications. Precisely controlling the substrate chemistry, architecture, and patterning may enhance the delivery efficiency and control gene transfer, which would increase applications to research, diagnostics, and therapies.

Further Studies on Substrate-Mediated Gene Delivery for Spatially Patterned Gene Expression Additional studies were done to examine immobilization of PEI/DNA complexes to the polymer surface. HEK293T cells seeded onto a polymer disk with immobilized PEI/DNA complexes encoding for b-galactosidase showed significant numbers of transfected cells across the disk following X-gal staining (FIG. 6a). For substrate-mediated delivery on PLG, the percentage of transfected cells was equal to 67% for delivery from the polymer of immobilized DNA complexes (FIG. 6b). The number of transfected cells by surface delivery was significantly greater than that obtained for bolus delivery of similar or greater quantities of DNA.

This ability to transfect cells by immobilized DNA was subsequently translated to three- dimensional structures. PEI/DNA complexes encoding for beta galactosidase were incubated within the scaffolds for 2 hours, and then cells were seeded into the pores of the scaffolds. X-gal staining of the scaffolds showed transfected cells throughout the scaffold. This approach provides significant transfection in vitro, and experimental studies propose to examine this mechanism in vivo, and apply it to studies of tissue formation in vitro and in vivo.

Complexes have been immobilized to specific regions to demonstrate the potential of substrate-mediated delivery to spatially pattern gene transfer. A section of the surface was coated with DNA complexes. After complex adsorption, the surfaces were washed and cells were seeded homogeneously (FIG. 7a). Extensive cells transfection (green) was observed in the region with immobilized complexes, while few cells were transfected sections without immobilized complexes (FIG. 7b). These images indicate the ability of substrate-mediated delivery to spatially pattern gene expression.

Example 7

Bioactivity of Chondroitinase ABC Released from Tubular Scaffolds

The ability to encapsulate and release the enzyme chondroitinase ABC, in active form, was confirmed. Scaffolds were fabricated by gas foaming a mixture of lyophilized enzyme with empty microspheres. The tubes were immersed in buffer and the released enzyme was collected. The enzyme was incubated with a solution of chondroitin sulfate A. The integrity of chondroitin sulfate (CS) was monitored by measurement of the absorbance of CS with 1,9-dimethylmethylene blue (DMMB—Aldrich) at 525 nm. As expected, incubation of the released enzyme with CS results in degradation of CS, indicating that the released enzyme is active (FIG. 8). When compared to controls, we estimate that the enzyme has retained greater than 80% of its activity.

Example 8

NGF Releasing Tubes for Directing Neurite Outgrowth

Tubes capable of NGF release are able to direct neurite extension through the tube more effectively than the addition of NGF to the culture media. An in vitro culture system has been developed in which a collagen gel fills the lumen of a half-tube (FIG. 9a). The dorsal root ganglia (DRG) are then placed onto the collagen at either the end or the center of the tube and the entire construct is mounted to a glass slide. This system allows visualization of the direction and extent of neurite extension by the DRG using a fluorescence microscope. For blank tubes (i.e., no NGF) and with NGF added to the culture media, the DRGs placed near the end of the tube have neurite extension toward the exterior solution (FIG. 9b), with minimal neurite extension toward the interior. DRG placed at the center of the tube have minimal neurite extension, likely due to limited availability of the NGF. In contrast, DRGs at the center of an NGF releasing tube have extensive neurite extension through the collagen (FIG. 9c). Additionally, the DRGs near the end of the tube have preferential neurite extension toward the interior of the tube relative to extension toward the exterior.

Example 9

Transfection by Immobilized PEI/DNA Complexes

We had previously demonstrated the ability to transfect cells by DNA immobilized to a 2- or 3-dimensional PLG scaffold. We have characterized binding and transfection to translate this mechanism to engineering of tissues. Initial studies quantified the extent of binding of PEI/DNA complexes to the substrate as a function of the N/P ratio and the amount of DNA incubated with the surface. For all conditions, increasing the time of incubation results in increased binding. However, most of the DNA binds within the first 4 hours. The immobilized DNA is stable, with less than 15% released during the initial 24 hours (not shown).

Increasing the incubation time of DNA complexes on the disk, which increases the amount of immobilized DNA, results in increasing extents of transgene expression. For all conditions tested, substrate immobilization increases expression relative to delivery of similar quantities as a bolus (FIG. 10a). However, note that the number of transfected cells decreases with increasing time of incubation (FIG. 10b). Nearly 70% of the cells are transfected with 90 ng of complexes immobilized to the substrate, with only 30% transfected for a 24 hour incubation. Again, the number of cells transfected is significantly enhanced by delivery from the substrate relative to bolus delivery.

The expression levels on the three-dimensional scaffold were approximately an order of magnitude greater than on the two-dimensional scaffolds (FIG. 11a). Additionally, the ability to store polymer with immobilized DNA was examined by lyophilizing disks followed by subsequent seeding of cells. Disks lyophilized in the presence of sucrose had levels of expression that were similar to the expression levels observed without lyophilization (FIG. 11b). The ability to store the scaffolds suggests the potential for scaffolds to be prefabricated and used when desired, which would be important for future clinical applications Surface delivery of DNA complexes provides an opportunity to regulate the number of transfected cells, and the extent of transgene expression. Studies with transplantation of cells genetically engineered to secrete varying levels of VEGF, have demonstrated that the number of expressing cells and the extent of transgene expression significantly affect the physiological response and quality of tissue formed (Ozawa et al (2004), J Clin Invest., February;113(4):516-27).

Example 10

In vitro Regeneration Model: DRG and Fibroblasts Co-Cultured on DNA Release Polymer Substrates A co-culture system was developed involving NIH/3T3 fibroblasts and primary neurons isolated from chick dorsal root ganglion (Day 8). The neurite outgrowth model is depicted in FIG. 21. Fibroblasts simulate the target for in vivo delivery, and serve as bioreactors for the localized production of nerve growth factor. Fibroblasts are transfected by DNA complexes that are either released from the polymer or that are immobilized to the surface. Delivery of a plasmid encoding for nerve growth factor, results in secretion of NGF into the media and increasing concentrations over time (FIG. 12a). Primary neurons cultured with the fibroblasts extend neurites in response to the NGF secretion by the fibroblasts (FIG. 12b and FIG. 22).

Example 11

Axonal Elongation Model

Polymer tubes were implanted into the axonal elongation model (FIG. 13a) and supported and directed neurite outgrowth. The axonal elongation model involves the attachment of a graft to the spinal cord. The graft is attached only at one end, which prohibits functional recovery. However, axon entry into the graft can be easily quantified and traced to the cell body in the ganglia. The dorsal columns of adult rats are transected bilaterally, severing the primary somatosensory axons ascending in the spinal cord from dorsal root ganglia (DRG) below the level of the lesion. Two weeks following in vivo implantation, neurite extension into the tube was assessed by filling the site with the fluorescent tracer Fluorogold, which is internalized by neurites and transported to the cell body. The dorsal root ganglia from the lumbar region were subsequently isolated and examined for the presence of fluorescently labeled neurons. Approximately 4% of the neurons in the dorsal root ganglia were labeled with the fluorescent tracer (FIG. 13b). These results indicate that the polymer implanted at the injury site does not inhibit neurite extension and provides a baseline to examine the ability of controlled drug delivery from the tube to promote neurite extension.

Example 12

Functional Recovery Model

The functional recovery model involves inserting a polymer scaffold into an injury site in the spinal cord, and regeneration is assessed through analysis of neurite ingrowth and the regain of ambulatory function. Adult male Sprague-Dawley rats (200-300 g) were anesthetized and a laminectomy was performed at the T10 vertebral level to expose the spinal cord. A cavity was formed in the left of the spinal cord (FIG. 14a), and a multi-lumen polymer scaffold was inserted (FIG. 14b, c). Sutures (5-0 chromic gut) were used to appose the muscle, and wound clips were used on the skin.

Following implantation, bladders were expressed twice daily for the first 3 days, at which point the animal recovered bladder function. Implants retained their position at the implant site and had good apposition with the surrounding tissue (FIG. 15a, b). The Basso, Beattie, and Bresnahan (BBB) scoring system was employed to monitor neurological recovery from injury to the spinal cord (Table 3). By 4 days, the left side (implant) had either no movement, up to slight movements of ankle, joint, and hip. The right side had slight movement of all 3 joints, with some showing plantar placement. By 8 days, most animals were frequently stepping, but with no coordination (BBB score: 11). These studies demonstrate the ability to implant scaffolds into the injury model, with the scaffolds performing the necessary mechanical functions. Additionally, these studies provide the foundation for examining enhanced regeneration by localized DNA delivery.

Example 13

Neurotrophin Release from Single and Multiple Lumen Nerve Guidance Channels

The fabrication of neural conduits (nerve guidance channels) with either single or multiple lumens capable of controlled protein delivery was studied. Conduits were fabricated from the copolymers of lactide and glycolide (PLG) with the assembly and fusion of microspheres using a gas foaming process. The gas foaming process has been to fabricate porous tissue engineering scaffolds, and the current studies demonstrate the capability of forming conduits with a defined macrostructure. A wet granulation process was adapted to improve homogeneity of the mixture and fabrication of the desired geometries. The fabrication conditions were examined for their ability to determine the porosity, mechanical properties, and rate of protein release. In particular, the release rate was characterized for conduits formed by either (i) mixing protein with microspheres or (ii) encapsulating protein within microspheres, prior to gas foaming. The release studies employed nerve growth factor (NGF) as a model neurotrophic factor. The bioactivity of released NGF was assessed by the ability to stimulate neurite outgrowth from dorsal root ganglia. The materials and methods used in these studies have been outlined above.

Results

Single Lumen Conduit

PLG conduits with a single lumen were fabricated by fusion of microspheres within a custom-designed mold. The resulting conduits have an inner diameter equal to 2.35 mm and an outer diameter of 3.15 mm (FIG. 1a). Similar molds have been employed to fabricate conduits with inner diameters equal to 0.8 mm and 1.4 mm, with corresponding outer diameters of 1.6 mm and 2.6 mm, respectively (data not shown). Increasing the porogen to polymer ratio from 0:1 to 15:1 increases the conduit porosity, with a maximal porosity of $91.6 \pm 1.5\%$ (Table 1). For conduits formed without porogen, the outer and inner surfaces appear relatively smooth. A cross-sectional view of these conduits shows an internal closed pore structure, which is consistent with the porosity measurements that indicate the conduits are approximately 50% porous (Table 1). Forming conduits with porogen increased the porosity (Table 1), and open pores could be visualized at the conduit surface.

Multi-Lumen Conduit

Conduits with multiple lumens were fabricated using a custom-designed mold (FIG. 1B) that allowed the creation of uniform, linear channels through the interior. Conduits have been fabricated in length ranging from 4 mm to 1 cm, and the channels can be observed at each end (FIG. 1B). Channels with diameters of 150 µm or 250 µm have been created that span the length of the conduit. For channels with a diameter of 150 µm, a total of 30 channels could be incorporated within a cross sectional area of 1.35 mm$^2$. Note that all conduits are formed with porogen to polymer ratios greater than 2:1, since fabrication without porogen leads to difficulties with pin removal. Consistent with the single lumen conduits, the porosity increased with an increasing porogen to polymer ratio (Table 1). Additionally, the porosity attributable to the channels ranged from $2.5 \pm 0.2\%$ to $4.2 \pm 0.2\%$ of the total porosity, with the larger channels contributing a greater porosity.

PLG Porous Conduit Mechanical Properties

The transverse compressive strength (Sc) and elastic moduli (E) of the conduits were strongly decreasing functions of the porogen to polymer ratio. A representative force/displacement curve for a single lumen conduit, from which the Sc was determined, is shown (FIG. 24A). The yield point typically occurred at values for the normalized displacement between 0.15 and 0.20. Values for Sc at this yield point decreased from 840 N/m to 45 N/m as the porogen to polymer ratio increased from 2:1 to 10:1 (FIG. 24B, $p<0.01$). For the multiple lumen conduits, a representative stress/strain curve used for determination of the moduli is shown (FIG. 25A). These moduli were determined for both the compression (Ec) and decompression (Ed) modes. The curve shown in FIG. 25A corresponds to values for Ec and Ed which are equal to 134 kPa and 382 kPa, respectively. The moduli determined from each curve decreased with an increasing porogen to polymer ratio. For the compression curve, the value of Ec for conduits formed with porogen to polymer ratio of 5:1 was more than 2.5 times higher than for a porogen to polymer ratio of 12:1, (FIG. 25B, $p<0.01$). For the decompression curve, the value for Ed decreased from 520 kPa to 340 kPa as the quantity of porogen increased (FIG. 25C, $p<0.01$). The greater values for Ed relative to Ec indicate that the deformation is not completely elastic. This inelasticity likely results from damages that accumulate during the compression process due to collapse of weaker pores within the conduit.

NGF Release from PLG Conduits

The leaching step for the conduits, which is performed to create a porous structure, resulted in losses ranging from 3% to 14% of the incorporated protein. Conduits fabricated by mixing of lyophilized NGF with the microspheres prior to foaming resulted in greater losses during the leaching step (N1%) relative to NGF that was encapsulated into the microspheres (ranged from 3% to 8%) (Table 2). For the same polymer composition, NGF loss during leaching increased as the porogen to polymer ratio increased from 2:1 to 10:1. A sustained release of protein from the porous conduits was observed for at least 42 days, with the release rate primarily dependent upon the mechanism of incorporation. Nerve conduits with single lumens were formed from microspheres composed of either (i) high molecular weight polymer alone, or (ii) blended high and low molecular weight polymer prior to microsphere fabrication. The release from the single lumen conduits was sustained for at least 42 days, and the percentage of incorporated protein released was statistically greater ($p<0.05$) for the mixed formulation (44.6±3.9%) than for encapsulated microspheres (24.1±1.3%, FIG. 16A). The release from the multiple lumen conduits was observed up to 9 days (FIGS. 17 and 18). The polymer composition did not affect the release profile for conduits formed with lyophilized protein mixed with the microspheres ($p>0.1$). However, for conduits formed by protein encapsulation into microspheres, the release profile is dependent upon the polymer composition, with faster release observed for microspheres containing 25% low molecular weight polymer and 75% high molecular weight polymer ($p<0.05$). Varying the porogen to polymer ratio from 2:1 to 10:1 indicated that the release is not dependent upon the porogen content, ($p>0.05$, FIG. 16B). However, the absence of porogen during conduit fabrication resulted in an initial burst of protein during the initial 48 h, with no significant release for the following 36 days (data not shown).

Bioactivity Assay of NGF Released

NGF released from porous PLG conduits (single and multiple channels) was bioactive and stimulated neurite outgrowth by DRG. NGF collected from the release medium at 1 day, 7 days, and 14 days stimulated neurite outgrowth by primary DRG (FIG. 26). Furthermore, the average neurite length at 24 h of culture was not statistically different ($p>0.05$) for the released NGF compared to fresh NGF, indicating that the protein remains bioactive. This bioactivity was seen for NGF released from single lumen or multiple lumen conduits. For single lumen conduits, bioactivity was observed for both mixing protein with the microspheres and encapsulating protein in the microspheres. Negative controls of release media from conduits without NGF did not elicit neurite extension.

In vivo Studies

The stability of the channels within the conduit was assessed by subcutaneous implantation. The channels remained intact and cells from the surrounding tissue infiltrated into the channels and the porous structure. At 13 days post-implantation, tissue was found within each of the channels, and the channels had retained their original dimensions (FIG. 27).

Summary of Results

As shown herein, single lumen and multiple lumen nerve guidance channels (conduits) capable of controlled, sustained release of neurotrophic factors were fabricated, and have potential application in nerve regeneration. These conduits were fabricated from a mixture of PLG microspheres and porogen that were processed by gas foaming/particulate leaching process and a wet granulation process enhanced the flowability and homogeneity of the porogen/polymer mixture and enabled the fabrication of the desired structures. The quantity of porogen incorporated with the polymer regulated the porosity and mechanical properties of the resulting construct. For single lumen conduits, increasing the porogen to polymer ratio from 2:1 to 10:1 decreased the Sc from 840 N/m to 45 N/m. For multiple lumen conduits, increasing the porogen to polymer ratio from 5:1 to 12:1 decreased the compression elastic modulus by more than 2.5 times. In vivo implantation of the conduits showed retention of the channel architecture and cellular infiltration from the surrounding tissue. NGF was incorporated by either mixing with the polymer microspheres or encapsulating within the microspheres prior to gas foaming. A sustained release was observed for at least 42 days, with the release rate controlled by the method of incorporation and the polymer molecular weight. Release studies using the neurotrophic factor NGF demonstrated the ability to stimulate neurite outgrowth from primary DRG.

Encapsulation of the protein within the polymer microsphere prior to foaming results in a more sustained release relative to mixing of the protein with the polymer. Encapsulating the protein likely retards the release by effectively entrapping the protein within the polymer interior, thus increasing the barrier for release from the conduit. The molecular weight of the polymer examined in this study was shown to influence the release rate from the conduit for protein encapsulation into microspheres prior to gas foaming. However, in the case of NGF that was mixed with polymer, the release was not affected by the polymer composition. Here, the protein is likely present at the polymer surface, with release controlled by hydration of the conduit and subsequent protein desorption from the polymer and diffusion through the pores. For both mixed and encapsulated protein, the incorporation of porogen into the conduit led to a sustained release relative to the absence of porogen. In the absence of porogen, release is hypothesized to occur from the surface associated protein, with the remainder of the protein entrapped within the polymer and unable to be released within the study duration. For porogen to polymer ratios ranging from 2:1 to 10:1, the structures are at least 50% porous with open pores, which likely provides sufficient water penetration for subsequent protein release. The increasing porogen content leads to greater losses during the leaching process, yet has no significant effect on the release profile. The released protein retained its bioactivity during the time periods investigated.

Nerve conduits must maintain a stable path across the injury site, which is dependent upon the mechanical properties of the conduit. A common problem with nerve conduits in vivo is the collapse of the channel, thereby limiting neurite outgrowth and subsequent regeneration (C. E. Schmidt, J. B. Leach, Annu. Rev. Biomed. Eng. 5 (2003)293-347; V. B. Doolabh, M. C. Hertl, S. E. Mackinnon, Rev. Neurosci. 7 (1) (1996) 47-84). Nerve regeneration models typically examine times ranging from a few weeks to several months, with tissue growing through the conduit within weeks (J. S. Belkas, M. S. Shoichet, R. Midha, Neurol. Res. 26 (2) (2004) 151-160; T. Hadlock, et al., Arch. Otolaryngol. Head Neck Surg. 124 (10) (1998) 1081-1086; M. B. Bunge, Neuroscientist 7 (4) (2001) 325-339). The implanted conduits must create and maintain the space for tissue regeneration during this time period. Preliminary in vivo results indicate that the nerve guidance channels studied here retain their original architecture, and allow for cellular infiltration through the channels. The ability to manipulate the porosity allowed fabrication of conduits with a wide range of mechanical strength. The single lumen conduits have values for Sc ranging from 45 N/m to 840 N/m that are dependent upon the porosity. The wet granulation/gas foaming process produces an elastic modulus during compression (Ec) for the porous conduit ranging from 110 to 320 kPa.

The combination of a nerve conduit with neurotrophic factor release can physically support neurite outgrowth and provide the factors that stimulate neuron survival and neurite extension. These conduits provide a structural support that stabilizes the damaged nerve and maintains a path between the stumps by limiting infiltration from the surrounding tissue In conclusion, an approach to fabricate conduits with single or multiple lumens that are capable of controlled protein delivery was developed. These conduits have sufficient mechanical properties, controlled by porogen content, to maintain open channels that allow for tissue in growth in vivo. Protein delivery from the conduit is regulated by the mechanism of incorporation (encapsulated versus mixed), the polymer molecular weight, and the presence of porogen. The combination of a nerve conduit and controlled protein delivery has the potential to support and promote regeneration in the nervous system.

TABLE 1

Porosity for single lumen conduits and multiple lumen conduits with various porogen to polymer ratios

| Single lumen conduit | | Multiple lumen conduit | | |
| --- | --- | --- | --- | --- |
| Porogen to polymer ratio | Total porosity (%) | Porogen to polymer ratio | Number of channels (diameter) | Total porosity (%) | Porosity due to channels (%) |
| 0:1 | 50.5 ± 3.5 | 5:1 | 12 (150 µm) | 87.9 ± 0.8 | 2.2 ± 0.1 |
| 2:1 | 73.5 ± 6.3 | 10:1 | 12 (150 µm) | 92.9 ± 0.4 | 2.3 ± 0.1 |
| 5:1 | 80.1 ± 6.4 | 12:1 | 12 (150 µm) | 93.2 ± 0.7 | 2.5 ± 0.2 |
| 10:1 | 90.0 ± 1.6 | 12:1 | 8 (250 µm) | 93.6 ± 0.1 | 4.2 ± 0.2 |
| 15:1 | 91.6 ± 1.5 | 15:1 | 12 (150 µm) | 94.5 ± 0.3 | 2.4 ± 0.1 |

The shaded region indicates the variation in number of channels.

TABLE 2

Experimental conditions for release studies of single lumen conduits with percent protein lost due to leaching

| Conditions | Polymer composition | Porogen to polymer ratio | Incorporation method | % Loss due to leaching |
| --- | --- | --- | --- | --- |
| 1 | 100% HMW | 5:1 | Encapsulated | 3.1 F0.2 |
| 2 | 75% HMW, 25% LMW | 5:1 | Encapsulated | 5.6 F0.6 |
| 3 | 50% HMW, 50% LMW | 5:1 | Encapsulated | 5.0 F1.8 |
| 4 | 75% HMW, 25% LMW | 2:1 | Encapsulated | 3.3 F0.2 |
| 5 | 75% HMW, 25% LMW | 10:1 | Encapsulated | 8.0 F0.7 |
| 6 | 100% HMW | 5:1 | Mixed | 11.0 F1.5 |
| 7 | 75% HMW, 25% LMW | 5:1 | Mixed | 14.0 F1.2 |

Example 14

Plasmid Delivery in vivo from Porous Tissue-Engineering Scaffolds: Transgene Expression and Cellular Transfection Gene transfer for the sustained release of plasmid from porous tissue engineering scaffolds was investigated to identify the design parameters that regulate the extent and duration of transgene expression and to characterize the distribution of transfected cells. Scaffolds were fabricated by a gas foaming/particulate leaching process, in which wet granulation was employed to increase the plasmid encapsulation and scaffold integrity relative to the standard processing without wet granulation. The quantity, duration, and location of transgene expression in vivo were monitored with a noninvasive imaging system. The distribution of transfected cells within and around the implanted scaffold was also examined by immunohistochemistry. Finally, the ability of transgene expression to induce physiological responses was investigated using an angiogenesis model, in which plasmid encoding VEGF was delivered. The materials and methods used in these studies have been outlined above.

Results

In Vitro Characterization of Plasmid-Releasing Scaffolds

Wet granulation prior to gas foaming improved the plasmid incorporation efficiency, yet had little effect on the release profile or DNA integrity. The standard mixing procedure produced encapsulation efficiencies of 46.5 +/-3.9%, and wet granulation increased the efficiency to 59.5±2.4% ($P<0.001$, FIG. 28A). Scaffolds formed following wet granulation of the solid mixture had a sustained release of plasmid for at least 3 weeks with retention of DNA integrity. We observed an initial burst equal to 53.0±8.1% of the incorporated DNA during the first 3 days, followed by a steady release of approximately 3% per week (FIG. 28B). We found supercoiled DNA throughout the 21 days of the release study; however, the fraction of released plasmid in the supercoiled conformation decreased to less than 20% after 14 days (FIG. 28C).

In Vivo Luciferase Expression

Figure 5:
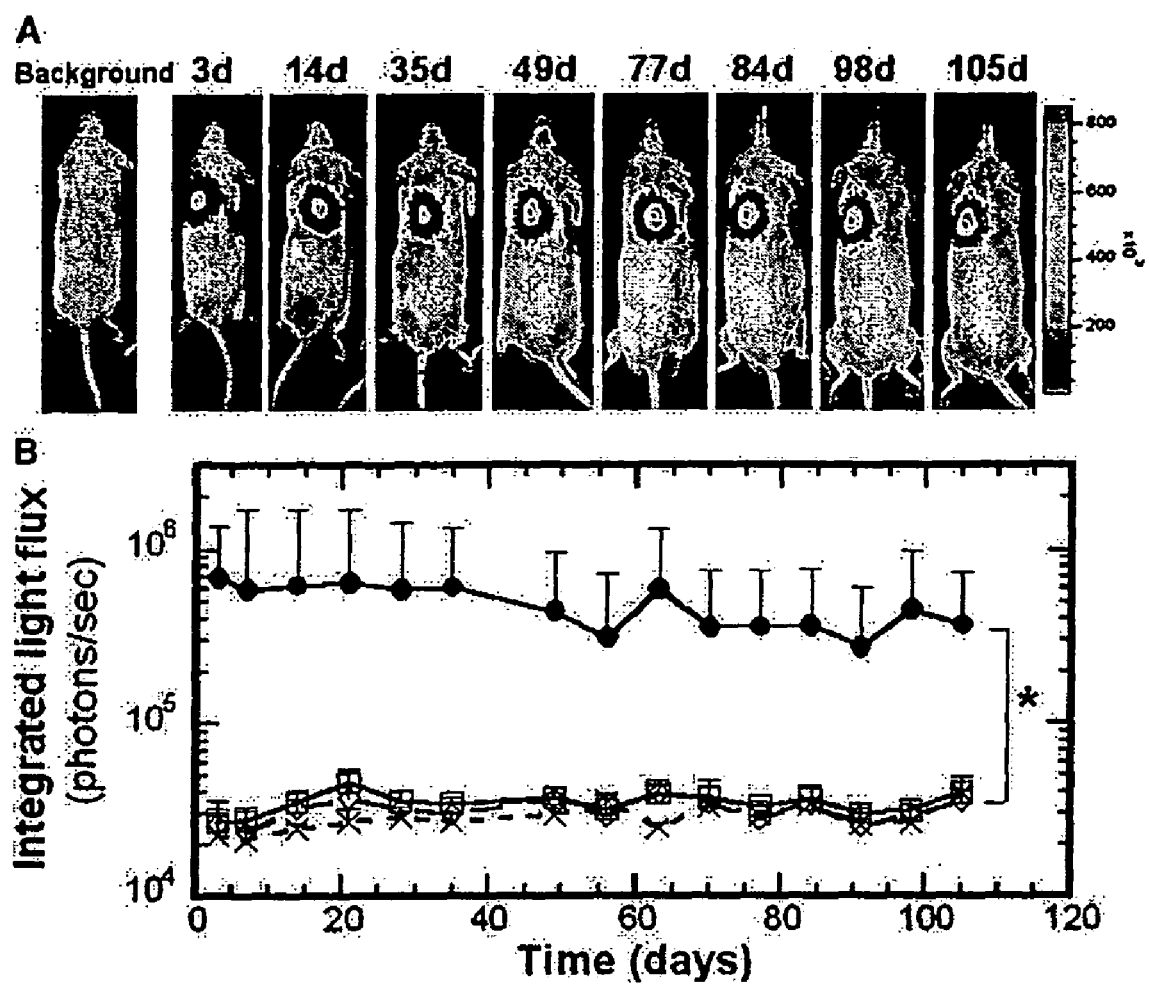
FIG. 5: (A) Bioluminescence imaging of mouse with subcutaneous implant of porous scaffolds loaded with 800 µg of naked DNA encoding for luciferase (pLuc) up to 105 days.

Scaffolds formed by wet granulation and subsequent gas foaming induced transgene expression in vivo, while the standard mixing process produced inconsistent expression. Initial studies employed scaffolds fabricated using either the standard or the wet granulation mixing procedures, with 500 Ag of pLuc input to the process. For scaffolds fabricated by the standard process, we observed luciferin-induced light emission in vivo for 43.5% of the scaffolds (10 of 23), with light emission persisting for 3 to 7 days (data not shown). The scaffold dimensions were not maintained following implantation, suggesting that the pore structure was collapsing. For scaffolds fabricated with wet granulation and subsequent gas foaming, the scaffold dimensions after 21-day implantation were similar to those of the initial construct, indicating that the scaffolds had sufficient mechanical integrity to resist the compressive or contractile forces in vivo. Note that relative to previous reports of plasmid-releasing scaffolds (Shea, L. D., Smiley, E., Bonadio, J., and Mooney, D. J. (1999), Nat. Biotechnol. 17: 551-554), these scaffolds were fabricated from a blended mixture of low- and high-molecular-weight polymer, which combined with wet granulation likely contributed to the greater mechanical stability. We observed cellular infiltration throughout the scaffold interior (data not shown), indicating that the pores were interconnected. For plasmid-loaded scaffolds, we obtained light emission in 89% of the animals (8 of 9), with levels at day 3 that were significantly above background or empty scaffold controls ($P<0.05$). Light emission was visualized at subsequent time points; however, the levels were not significantly above those of controls ($P>0.05$). Increasing the plasmid loading in scaffold resulted in sustained transgene expression in vivo for at least 105 days (FIG. 5). For scaffolds fabricated with 800 µg plasmid input to the process, we observed light emission directly over the implant in all samples (7 of 7, FIG. 5A). The light emission levels were significantly greater than those of the control conditions (FIG. 5B, <0.05). Control conditions included scaffolds without DNA, or with plasmid lacking the luciferase cDNA, which produced light emission equivalent to background (FIG. 5B). For time points after 105 days, measurements of light emission for the pLuc-loaded scaffolds were not significantly different from those of the control conditions (P≧0.05, not shown). The population averages are not significantly different at these later time points, as half of the samples decreased to background levels of light emission. The remaining samples, however, continued to have luciferin-induced light emission above background, with one sample having consistently elevated levels through 189 days.

Transfected Cell Distribution

Transfected cells were initially localized to the scaffold periphery, while at later times these cells were observed throughout the pores of the scaffold. The stability of these scaffolds relative to previous reports (Shea, L. D., Smiley, E., Bonadio, J., and Mooney, D. J. (1999). Nat. Biotechnol. 17: 551-554) allowed immunohistochemistry to be performed more effectively for tissue within the pores of the scaffold. At 3 days postimplantation, cells had not effectively penetrated into the pores of the scaffold. Luciferase-positive cells were found at the periphery of the scaffold and in the tissue immediately adjacent to the scaffold. Note that the interior of the scaffold could not be visualized, which resulted from difficulties in sectioning due to the limited tissue within the scaffold. At 17 and 126 days postimplantation, luciferase-positive cells were primarily located within the scaffold interior. At 17 days, we observed most positively stained cells immediately adjacent to the polymer and not within the tissue that filled the pores. At 126 days postimplantation, however, luciferase-positive cells were distributed within the pore interior and adjacent to the polymer. Immunohistochemical staining for proliferating cell nuclear antigen (PCNA) demonstrated positively stained cells within the scaffold interior, which appeared sporadically within the pores and adjacent to the polymer (data not shown). The pattern of PCNA staining did not correspond directly to the pattern of luciferase staining.

Blood Vessel Formation

Scaffold-based delivery of pVEGF to promote vascular ingrowth, which is an important process for successful tissue engraftment, was examined. At 3 weeks postimplantation, we observed visually large numbers of blood vessels on the pVEGF-loaded scaffolds, with fewer vessels found surrounding pLuc-loaded scaffolds (FIG. 23a and b). The density of positively stained blood vessels at 3 weeks was significantly greater for scaffolds releasing pVEGF (102.7±37.3/mm2) than pLuc (63.5±27.4/mm2) (P<0.001). Additionally, we observed larger blood vessels with the scaffolds releasing pVEGF compared to pLuc (P<0.001). The average cross-sectional area for the blood vessels was equal to 532.2±742.4 and 225.2±318.8 μm2 for pVEGF and pLuc, respectively.

TABLE 3

BBB Scoring Method

| BBB scores | | Comments |
| --- | --- | --- |
| 0 | No observable hindlimb (HL) movement | None |
| 1 | Slight movement on one or two HL joints | Slight 50% of joint range |
| 2 | Extensive movement of one HL joint and slight movement of the other joint | Extensive 50% of joint range |
| 3 | Extensive movement of two HL joints | Two joints = usually hip & knee |
| 4 | Slight movement of three HL joints | Three joints = hip, knee & ankle |
| 5 | Slight movement of two HL joints & extensive movement of third HL joint | |
| 6 | Extensive movement of two joints HL joints & slight movement of third HL joint | Third joint = usually the ankle |
| 7 | Extensive movement of all three HL joints | |
| 8 | Sweeping with no weight support or Plantar placement with no weight support | Sweeping = rhythmic 3 joint movement |
| 9 | Plantar placement with weight support OR Dorsal stepping with weight support | Weight support = HL extensor contraction with elevation of hindquarters in stance |
| 10 | Occasional weight supported steps with no forelimb-hindlimb (FL-HL) coordination | Occasional = >5% & 50% Steps = plantar steps with weight support |
| 11 | Frequent to consistent steps (FCS) with no coordination | Frequent = 51-94% of the time Consistent = 95-100% of the time |
| 12 | FCS with occasional coordination | 6-50% bouts of locomotion coordinated |
| 13 | FCS with frequent coordination | 51-95% bouts of locomotion coordinated |
| 14 | Consistent coordinated steps (CCS) & paw rotated on placement & liftoff OR Frequent steps, consistent coordination With occasional dorsal steps | Rotated = internal or external rotation |
| 15 | CCS & no or occasional toe clearance & parallel paw position on initial placement | Parallel = paw placement to body Toe clearance = steps without toe drag |
| 16 | CCS & frequent toe clearance | Frequent toe clearance 50% no toe drag |
| 17 | CCS & parallel paw on placement and liftoff | |
| 18 | CCS & consistent toe clearance | Consistent toe clearance 4 toe drags |
| 19 | CCS & parallel paw on placement and liftoff Tail down part or all the time | Tail down = touches ground when walking |
| 20 | CCS & parallel paw on placement and liftoff Tail consistently up, trunk unstable | Trunk instability = lateral weight shifts, waddling, lurching |
| 21 | CCS, consistent toe clearance, parallel paws, tail consistent up, consistent trunk stability | Consistent trunk stability no lurching |

What is claimed is:

1. A scaffold for propagation of tissue, comprising a porous polymer matrix containing pores formed by gas foaming and pores formed by leaching out of a particulate from the polymer, wherein the polymer is mixed with a porogen by wet granulation prior to gas foaming and prior to molding of the scaffold, wherein the polymer matrix is PLG or PLGA and exhibits an elastic modulus of about 50 to about 500 kPa.

2. A scaffold for propagation of tissue, comprising a porous polymer matrix containing pores formed by gas foaming and pores formed by leaching out of a particulate from the polymer, wherein the polymer is mixed with a porogen by wet granulation prior to gas foaming and prior to molding of the scaffold, wherein the polymer matrix exhibits an elastic modulus of about 110 to about 320 kPa.

3. A nerve guidance channel constructed of a biodegradable, biocompatible polymer matrix containing pores formed by gas foaming and pores formed by leaching out of a particulate from the polymer, and optionally a section of impermeable polymer integrally connected, wherein the polymer is mixed with a porogen by wet granulation prior to gas foaming and prior to molding of the nerve guidance channel, having an inner diameter equal to about 0.8 to 2.35 mm and an outer diameter of about 1.6 mm to 3.15 mm.

* * * * *

SEQUENCE LISTING

<160> NUMBER OF SEQ ID NOS: 12

<210> SEQ ID NO 1
<211> LENGTH: 257

```
<212> TYPE: PRT
<213> ORGANISM: Homo sapiens

<400> SEQUENCE: 1

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 2
<211> LENGTH: 247
<212> TYPE: PRT
<213> ORGANISM: Homo sapiens

<400> SEQUENCE: 2

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
50                  55                  60

His Val Ile Glu Glu Leu Leu Asp Glu Asp His Lys Val Arg Pro Asn
65                  70                  75                  80

Glu Glu Asn Asn Lys Asp Ala Asp Leu Tyr Thr Ser Arg Val Met Leu
```

```
                    85                  90                  95
Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Met Val Leu Arg
            115                 120                 125

His Ser Asp Pro Ala Arg Arg Gly Glu Leu Ser Val Cys Asp Ser Ile
        130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 3
<211> LENGTH: 215
<212> TYPE: PRT
<213> ORGANISM: Homo sapiens

<400> SEQUENCE: 3

Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
             35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205
```

```
Arg Cys Asp Lys Pro Arg Arg
    210             215
```

<210> SEQ ID NO 4
<211> LENGTH: 241
<212> TYPE: PRT
<213> ORGANISM: Homo sapiens

<400> SEQUENCE: 4

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala
```

<210> SEQ ID NO 5
<211> LENGTH: 133
<212> TYPE: PRT
<213> ORGANISM: Homo sapiens

<400> SEQUENCE: 5

```
Met Gly Cys Arg Gly Cys Leu Pro Gly Ala Ala Pro His Arg Val Arg
1               5                   10                  15

Leu Pro Ala Ala Asn Pro Glu Asn Ser Arg Gly Lys Gly Arg Arg Gly
            20                  25                  30

Gln Arg Gly Lys Asn Arg Gly Cys Val Leu Thr Ala Ile His Leu Asn
        35                  40                  45

Val Thr Asp Leu Gly Leu Gly Tyr Glu Thr Lys Glu Glu Leu Ile Phe
    50                  55                  60

Arg Tyr Cys Ser Gly Ser Cys Asp Ala Ala Glu Thr Thr Tyr Asp Lys
```

```
                65                  70                  75                  80
Ile Leu Lys Asn Leu Ser Arg Asn Arg Arg Leu Val Ser Asp Lys Val
                    85                  90                  95

Gly Gln Ala Cys Cys Arg Pro Ile Ala Phe Asp Asp Asp Leu Ser Phe
                100                 105                 110

Leu Asp Asp Asn Leu Val Tyr His Ile Leu Arg Lys His Ser Ala Lys
            115                 120                 125

Arg Cys Gly Cys Ile
        130

<210> SEQ ID NO 6
<211> LENGTH: 119
<212> TYPE: PRT
<213> ORGANISM: Homo sapiens

<400> SEQUENCE: 6

Tyr Ala Glu His Lys Ser His Arg Gly Glu Val Ser Val Cys Asp Ser
  1               5                  10                  15

Glu Ser Leu Trp Val Thr Asp Lys Ser Ser Ala Ile Asp Ile Arg Gly
                20                  25                  30

His Gln Val Thr Val Leu Gly Glu Ile Lys Thr Gln Asn Ser Pro Val
            35                  40                  45

Lys Gln Tyr Phe Tyr Glu Thr Arg Cys Lys Glu Ala Arg Pro Val Lys
        50                  55                  60

Asn Gly Cys Arg Gly Ile Asp Asp Lys His Trp Asn Ser Gln Cys Lys
 65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
                100                 105                 110

Ser Arg Lys Ile Gly Arg Thr
            115

<210> SEQ ID NO 7
<211> LENGTH: 155
<212> TYPE: PRT
<213> ORGANISM: Homo sapiens

<400> SEQUENCE: 7

Met Ala Glu Gly Glu Ile Thr Thr Phe Thr Ala Leu Thr Glu Lys Phe
  1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
```

```
                130                 135                 140
Ile Leu Phe Leu Pro Leu Pro Val Ser Ser Asp
145                 150                 155

<210> SEQ ID NO 8
<211> LENGTH: 288
<212> TYPE: PRT
<213> ORGANISM: Homo sapiens

<400> SEQUENCE: 8

Met Val Gly Val Gly Gly Asp Val Glu Asp Val Thr Pro Arg Pro
 1               5                  10                  15

Gly Gly Cys Gln Ile Ser Gly Arg Ala Ala Arg Gly Cys Asn Gly Ile
                20                  25                  30

Pro Gly Ala Ala Ala Trp Glu Ala Leu Pro Arg Arg Ala Pro Arg
            35                  40                  45

Arg His Pro Ser Val Asn Pro Arg Ser Arg Ala Ala Gly Ser Pro Arg
         50                  55                  60

Thr Arg Gly Arg Arg Thr Glu Glu Arg Pro Ser Gly Ser Arg Leu Gly
 65                  70                  75                  80

Asp Arg Gly Arg Gly Arg Ala Leu Pro Gly Gly Arg Leu Gly Gly Arg
                 85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
        130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
                180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
        210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 9
<211> LENGTH: 114
<212> TYPE: PRT
<213> ORGANISM: Homo sapiens

<400> SEQUENCE: 9

Met Gly Asp Arg Gly Arg Gly Arg Ala Leu Pro Gly Gly Arg Leu Gly
 1               5                  10                  15

Gly Arg Gly Arg Gly Arg Ala Pro Glu Arg Val Gly Gly Arg Gly Arg
```

-continued

```
                20                  25                  30
Gly Arg Gly Thr Ala Ala Pro Arg Ala Ala Pro Ala Ala Arg Gly Ser
            35                  40                  45

Arg Pro Gly Pro Ala Gly Thr Met Ala Ala Gly Ser Ile Thr Thr Leu
 50                      55                  60

Pro Ala Leu Pro Glu Asp Gly Ser Gly Ala Phe Pro Pro Gly His
 65              70                  75                  80

Phe Lys Asp Pro Lys Arg Leu Tyr Cys Lys Asn Gly Gly Phe Phe Leu
                 85                  90                  95

Arg Ile His Pro Asp Gly Arg Val Asp Gly Val Arg Glu Lys Ser Asp
            100                 105                 110

Pro His
```

<210> SEQ ID NO 10
<211> LENGTH: 300
<212> TYPE: PRT
<213> ORGANISM: Homo sapiens

<400> SEQUENCE: 10

```
Met Gln Ala Leu Val Leu Leu Leu Cys Ile Gly Ala Leu Leu Gly His
 1               5                  10                  15

Ser Ser Cys Gln Asn Pro Ala Ser Pro Pro Glu Glu Gly Ser Pro Asp
                20                  25                  30

Pro Asp Ser Thr Gly Ala Leu Val Glu Glu Asp Pro Phe Phe Lys
                35                  40                  45

Val Pro Val Asn Lys Leu Ala Ala Val Ser Asn Phe Gly Tyr Asp
             50                  55                  60

Leu Tyr Arg Val Arg Ser Ser Met Ser Pro Thr Thr Asn Val Leu Leu
 65              70                  75                  80

Ser Pro Leu Ser Val Ala Thr Ala Leu Ser Ala Leu Ser Leu Gly Ala
                 85                  90                  95

Asp Glu Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
 130                 135                 140

Glu Lys Lys Leu Arg Ile Lys Ser Ser Phe Val Ala Pro Leu Glu Lys
 145                 150                 155                 160

Ser Tyr Gly Thr Arg Pro Arg Val Leu Thr Gly Asn Pro Arg Leu Asp
                 165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
                195                 200                 205

Gly Val Ala His Phe Lys Gly Gln Trp Val Thr Lys Phe Asp Ser Arg
 210                 215                 220

Lys Thr Ser Leu Glu Asp Phe Tyr Leu Asp Glu Arg Thr Val Arg
 225                 230                 235                 240

Val Pro Met Met Ser Asp Pro Lys Ala Val Leu Arg Tyr Gly Leu Asp
                 245                 250                 255

Ser Asp Leu Ser Cys Lys Ile Ala Gln Leu Pro Leu Thr Gly Ser Met
                 260                 265                 270

Ser Ile Ile Phe Phe Leu Pro Leu Lys Val Thr Gln Asn Leu Thr Leu
```

```
              275                 280                 285
Ile Glu Glu Ser Leu Thr Ser Glu Phe Ile His Asp
    290                 295                 300

<210> SEQ ID NO 11
<211> LENGTH: 497
<212> TYPE: PRT
<213> ORGANISM: Homo sapiens

<400> SEQUENCE: 11

Met Thr Val Phe Leu Ser Phe Ala Phe Leu Ala Ala Ile Leu Thr His
  1               5                  10                  15

Ile Gly Cys Ser Asn Gln Arg Arg Ser Pro Glu Asn Ser Gly Arg Arg
                 20                  25                  30

Tyr Asn Arg Ile Gln His Gly Gln Cys Ala Tyr Thr Phe Ile Leu Pro
             35                  40                  45

Glu His Asp Gly Asn Cys Arg Glu Ser Thr Thr Asp Gln Tyr Asn Thr
         50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Val Leu Leu Lys
            260                 265                 270

Gly Gly Lys Arg Glu Glu Glu Lys Pro Phe Arg Asp Cys Ala Asp Val
        275                 280                 285

Tyr Gln Ala Gly Phe Asn Lys Ser Gly Ile Tyr Thr Ile Tyr Ile Asn
    290                 295                 300

Asn Met Pro Glu Pro Lys Lys Val Phe Cys Asn Met Asp Val Asn Gly
305                 310                 315                 320

Gly Gly Trp Thr Val Ile Gln His Arg Glu Asp Gly Ser Leu Asp Phe
                325                 330                 335

Gln Arg Gly Trp Lys Glu Tyr Lys Met Gly Phe Gly Asn Pro Ser Gly
            340                 345                 350
```

-continued

```
Glu Tyr Trp Leu Gly Asn Glu Phe Ile Phe Ala Ile Thr Ser Gln Arg
        355                 360                 365

Gln Tyr Met Leu Arg Ile Glu Leu Met Asp Trp Glu Gly Asn Arg Ala
        370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
                405                 410                 415

Leu Ile Leu His Gly Ala Asp Phe Ser Thr Lys Asp Ala Asp Asn Asp
                420                 425                 430

Asn Cys Met Cys Lys Cys Ala Leu Met Leu Thr Gly Gly Trp Trp Phe
        435                 440                 445

Asp Ala Cys Gly Pro Ser Asn Leu Asn Gly Met Phe Tyr Thr Ala Gly
        450                 455                 460

Gln Asn His Gly Lys Leu Asn Gly Ile Lys Trp His Tyr Phe Lys Gly
465                 470                 475                 480

Pro Ser Tyr Ser Leu Arg Ser Thr Thr Met Met Ile Arg Pro Leu Asp
                485                 490                 495

Phe

<210> SEQ ID NO 12
<211> LENGTH: 190
<212> TYPE: PRT
<213> ORGANISM: Homo sapiens

<400> SEQUENCE: 12

Met Gly Val His Glu Cys Pro Ala Trp Leu Trp Leu Leu Leu Ser Leu
  1               5                  10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr
                180                 185                 190
```